United States Patent
Jin et al.

(10) Patent No.: US 11,142,752 B2
(45) Date of Patent: Oct. 12, 2021

(54) PULLULANASE MUTANT

(71) Applicant: Jiangnan University, Wuxi (CN)

(72) Inventors: Zhengyu Jin, Wuxi (CN); Yuxiang Bai, Wuxi (CN); Xiaoxiao Li, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 16/288,804

(22) Filed: Feb. 28, 2019

(65) Prior Publication Data

US 2019/0270976 A1 Sep. 5, 2019

Related U.S. Application Data

(63) Continuation of application No. PCT/CN2018/094612, filed on Jul. 5, 2018.

(30) Foreign Application Priority Data

Mar. 1, 2018 (CN) .......................... 201810170134.6

(51) Int. Cl.
*C12N 9/24* (2006.01)

(52) U.S. Cl.
CPC .... *C12N 9/2402* (2013.01); *C12Y 302/01041* (2013.01)

(58) Field of Classification Search
None
See application file for complete search history.

(56) References Cited

U.S. PATENT DOCUMENTS 10,167,482 B2 * 1/2019 Coffin ................ C12N 15/8271

FOREIGN PATENT DOCUMENTS

| GN | 105960457 A | 9/2016 |
| WO | 2017014974 A1 | 1/2017 |

OTHER PUBLICATIONS

Yu B et al., Investigation of the Interactions between the Hydrophobic Cavities of Cyclodextrins and Pullulanase, Molecules, Apr. 7, 2011, vol. 16, p. 3010-3017.

Iwamoto H. et al., Interaction between Pullulanase from Ktebsielta pneumoniae and Cyclodextrins. J. Biochem. Dec. 31, 1993, vol. 113, pp. 93-96.

Yamashita M. et al., Random Mutagnesis of Pullulanase from Klebsiella aerogenes for Studies of the Structure and Function of the Enzyme. J. Biochem. Dec. 31, 1994, vol. 116, pp. 1233-1240.

* cited by examiner

*Primary Examiner* — Hope A Robinson

(74) *Attorney, Agent, or Firm* — IPro, PLLC

(57) ABSTRACT

The disclosure herein relates to a method for reducing the inhibitory effect of a cyclodextrin on a pullulanase and belongs to the technical field of gene engineering, enzyme engineering or food science. The method of the disclosure prepares a pullulanase mutant by reasonably mutating the key amino acid of the pullulanase interactive with the cyclodextrin to reduce the inhibitory effect of the cyclodextrin on the pullulanase, thereby improving the hydrolysis activity of the pullulanase. The disclosure finds the interactive sites of the pullulanase and the cyclodextrin based on analysis of crystal structures of enzymes and inhibitors and sequence comparison of enzymes from different sources, and utilizes site-directed mutation to obtain the pullulanase mutant having reduced sensibility to the cyclodextrin, thereby improving the utilization ratio of the starch raw material and the yield of the cyclodextrin.

5 Claims, 4 Drawing Sheets

Specification includes a Sequence Listing.

PULLULANASE MUTANT

The disclosure is a continuation of PCT/CN2018/094612 with a filing date of Jul. 5, 2018, and CN 2018101701346 with a filing date of Mar. 1, 2018, all of which are enclosed herein in it entirety.

TECHNICAL FIELD

The disclosure herein relates to a method for reducing the inhibitory effect of a cyclodextrin on a pullulanase and belongs to the technical field of gene engineering, enzyme engineering or food science.

BACKGROUND

Pullulanase (EC 3.2.1.41) specifically hydrolyzes α-1,6 glycosidic bonds in pullulan, soluble starch, amylopectin and corresponding oligosaccharides to generate a short linear dextrin. Combination of the pullulanase and other amylases can greatly improve the utilization ratio of the starch raw materials, so that the pullulanase is widely applied to the starch industry.

In the starch sugar industry, the pullulanase has the function of hydrolyzing α-1,6 glycosidic bonds, so that the pullulanase has wide application prospects, can be used for preparing amylose, maltose and branched cyclodextrin, and can be combined with CGTase to produce the cyclodextrin. In the production process of the cyclodextrin, by taking production of α-CD as an example, because α-CGTase can not hydrolyze α-1,6 bonds in starch substrates, when α-CGTase is used alone to produce α-CD, the conversion rate is only 40%-60%. The addition of the pullulanase can significantly increase the conversion rate of the cyclodextrin, but the pullulanase is easily inhibited by the cyclodextrin, so that the debranching reaction and the cyclization reaction need to be performed separately, resulting in problems such as long production cycle and resource waste. In order to shorten the production cycle, increase the utilization ratio of the raw material starch and increase the yield of the cyclodextrin, a one-pot method of compounding the pullulanase and cyclodextrin glycosyltransferase is adopted to produce the cyclodextrin, and therefore, reduction of inhibition on the pullulanase by the cyclodextrin becomes an urgent problem to be solved.

Marshall J J, Iwamoto H, Iwamoto H et al. study the inhibitory effect of the cyclodextrin on the pullulanase in terms of enzyme activity, reaction kinetics and the like, and confirm that the cyclodextrin is a competitive inhibitor of the pullulanase. Yu Bo et al. further study the inhibitory effect of the cyclodextrin on the pullulanase, and study the influence of the cyclodextrin on the endogenous fluorescence and the secondary structure of the pullulanase on the basis of conventional characterization of enzymatic properties, thereby proving that the inclusion effect between a hydrophobic cavity of the cyclodextrin and an aromatic amino acid of the pullulanase is the intrinsic driving force of the cyclodextrin for inhibition of pullulanase activity. Related studies at home and abroad only focus on the interaction between the cyclodextrin and the pullulanase and do not propose specific and effective solutions.

The inventors preliminarily analyze and compare the sequences of the pullulanase from different sources, and the crystal structure (PDB:2E8Z) combining the pullulanase (NCBI accession number: AF008220.1) derived from *Bacillus subtilis* str. 168 and the cyclodextrin is already published, so that the pullulanase derived from *Bacillus subtilis* is selected as a template for experimental design. After characterization of the wild type pullulanase and the mutant, the disclosure finds that the mutant can significantly reduce the inhibitory effect of the product cyclodextrin. The reduction of the inhibitory effect is favorable for improving the utilization ratio of the starch raw material, increasing the yield of the cyclodextrin, and providing greater industrial application value for cyclodextrin production.

SUMMARY

In view of the above problems in the prior art, the disclosure provides a method for reducing the inhibitory effect of the cyclodextrin on the pullulanase. The disclosure finds the interactive sites of the pullulanase and the cyclodextrin based on analysis of crystal structures of enzymes and inhibitors and sequence comparison of enzymes from different sources, and utilizes site-directed mutation to obtain a pullulanase mutant having reduced sensibility to the cyclodextrin, thereby improving the utilization ratio of the starch raw material and the yield of the cyclodextrin.

The disclosure is directed to a pullulanase which is reduced in inhibitory effect of the cyclodextrin. The disclosure prepares a pullulanase mutant by reasonably mutating the key amino acid of the pullulanase interactive with the cyclodextrin to reduce the inhibitory effect of the cyclodextrin on the pullulanase, thereby improving the hydrolysis activity of the pullulanase. The key amino acid is phenylalanine.

The amino acid sequence of the pullulanase comprises an amino acid obtained by mutating the last position F (phenylalanine) in FNDXXRDXXXGXXF (as shown in SEQ ID NO: 1) contained in a parent amino acid sequence based on the parent amino acid sequence, wherein X can be any naturally occurring amino acid.

In one example, the parent amino acid sequence is an amino acid sequence of the pullulanase derived from any one of *Bacillus subtilis*, *Bacillus vireti*, *Bacillus atrophaeus*, *Geobacillus stearothermophilus*, *Bacillus mojavensis*, *Thermotoga maritima*, [*Brevibacterium*] *halotolerans*, *Thermus* sp. IM6501, *Bacillus cereus* FRI-35, *Bacillus halotolerans*, *Alteromonas mediterranea*, *Klebsiella pneumoniae*, *Thermotoga maritima*, *Escherichia coli*, *Enterobacter aerogenes*, *Bacillus tequilensis*, *Bacillus intestinalis*, *Bacillales*, *Bacillus licheniformis* and *Bacillus halotolerans*.

In one example, the parent amino acid sequence is any one of the following amino acid sequences with accession numbers on NCBI: WP_003229246.1 (*Bacillus subtilis*)(as shown in SEQ ID NO: 17), WP_024026701.1 (*Bacillus vireti*)(as shown in SEQ ID NO: 18), WP_010789532.1 (*Bacillus atrophaeus*)(as shown in SEQ ID NO: 19), KZE96788.1 (*Geobacillus stearothermophilus*)(as shown in SEQ ID NO: 20), WP_032731297.1 (*Bacillus mojavensis*) as shown in SEQ ID NO: 21), CAA04522.1 (*Thermotoga maritima*)(as shown in SEQ ID NO: 22), OEC77647.1 ([*Brevibacterium*] *halotolerans*)(as shown in SEQ ID NO: 23), AAC15073.1 (*Thermus* sp. IM6501)(as shown in SEQ ID NO: 24), AFQ12130.1 (*Bacillus cereus* FRI-35)(as shown in SEQ ID NO: 25 and WP_106020274.1 (*Bacillus halotolerans*)(as shown in SEQ ID NO: 26).

In one example, the amino acid sequence of the pullulanase comprises any segment of the following amino acid sequences:

(1) an amino acid sequence obtained by mutating the amino acid phenylalanine at the position 476 of the amino acid sequence of the pullulanase derived from *Bacillus subtilis* str. 168 (as shown in SEQ ID NO: 17);

(2) an amino acid sequence obtained by mutating the amino acid phenylalanine at the position 476 of the amino acid sequence of the pullulanase derived from *Bacillus vireti* (as shown in SEQ ID NO: 18);

(3) an amino acid sequence obtained by mutating the amino acid phenylalanine at the position 476 of the amino acid sequence of the pullulanase derived from *Bacillus atrophaeus* (as shown in SEQ ID NO: 19);

(4) an amino acid sequence obtained by mutating the amino acid phenylalanine at the position 481 of the amino acid sequence of the pullulanase derived from *Geobacillus stearothermophilus* (as shown in SEQ ID NO: 20);

(5) an amino acid sequence obtained by mutating the amino acid phenylalanine at the position 476 of the amino acid sequence of the pullulanase derived from *Bacillus mojavensis* as shown in SEQ ID NO: 21);

(6) an amino acid sequence obtained by mutating the amino acid phenylalanine at the position 601 of the amino acid sequence of the pullulanase derived from *Thermotoga maritima* (as shown in SEQ ID NO: 22);

(7) an amino acid sequence obtained by mutating the amino acid phenylalanine at the position 478 of the amino acid sequence of the pullulanase derived from [*Brevibacterium*] *halotolerans* (as shown in SEQ ID NO: 23);

(8) an amino acid sequence obtained by mutating the amino acid phenylalanine at the position 481 of the amino acid sequence of the pullulanase derived from *Thermus* sp. IM6501 (as shown in SEQ ID NO: 24);

(9) an amino acid sequence obtained by mutating the amino acid phenylalanine at the position 613 of the amino acid sequence of the pullulanase derived from *Bacillus cereus* FRI-35 (as shown in SEQ ID NO: 25); and

(10) an amino acid sequence obtained by mutating the amino acid phenylalanine at the position 476 of the amino acid sequence of the pullulanase derived from *Bacillus halotolerans* (as shown in SEQ ID NO: 26).

In one example, the parent amino acid sequence is an amino acid sequence of the pullulanase derived from *Bacillus subtilis* str. 168, and the sequence is shown in SEQ ID NO: 2.

In one example, the cyclodextrin is one or more of α-CD, β-CD and γ-CD.

In one example, the mutated amino acid phenylalanine is mutated into any one of the following amino acids: glycine, alanine, leucine, isoleucine, valine, proline, methionine, serine, glutamine, threonine, cysteine, aspartic acid, asparagine, glutamic acid, lysine, arginine or histidine.

The disclosure is also directed to a nucleotide encoding the pullulanase.

The disclosure is further directed to a vector or cell containing the nucleotide.

In one example, the vector can be one of PMC series, pET series or pGEX series plasmids.

In one example, the cell can be a microbial cell constructed by taking gram-negative bacteria, gram-positive bacteria or fungi as host bacteria.

In one example, the host bacteria can be *Escherichia coli*, *Bacillus subtilis* or *Saccharomyces*.

The disclosure is further directed to a method for reducing the inhibitory effect of the cyclodextrin on the pullulanase. The method prepares a pullulanase mutant by reasonably mutating the key amino acid of the pullulanase interactive with the cyclodextrin to reduce the inhibitory effect of the cyclodextrin on the pullulanase, thereby improving the hydrolysis activity of the pullulanase.

The method mutates the parent pullulanase; and the amino acid sequence of the mutated pullulanase comprises an amino acid obtained by mutating the last position F (phenylalanine) in FNDXXRDXXXGXXF contained in the parent amino acid sequence based on the parent amino acid sequence, wherein X can be any naturally occurring amino acid.

In one example, the mutation comprises the following specific processes:

(1) taking pullulanase genes as a template, selecting plasmids, constructing an expression vector, and preparing plasmids carrying the pullulanase genes, wherein the plasmids are selected from one of PMC series plasmids, pET series plasmids or pGEX series plasmids;

(2) analyzing a crystal structure to determine a key amino acid site for combination of the pullulanase and the cyclodextrin;

(3) designing a mutated primer of the key amino acid, and performing mutation by taking the plasmids carrying the pullulanase genes as a template to prepare mutated plasmids; and (4) transferring the mutated plasmids into the host bacteria, performing positive monoclonal fermentation culture to obtain a pullulanase mutant crude enzyme, and performing separation and purification to obtain a pullulanase mutant purified enzyme.

In one example, the method of separation and purification in step (4) is affinity chromatography, hydrophobic chromatography, ultrafiltration chromatography or gel filtration chromatography.

The disclosure has the following beneficial technical effects:

According to sequence comparison of the pullulanase from different sources, the pullulanase with the known crystal structure is taken as a template, and the crystal structure is analyzed to obtain an amino acid related to the inhibitory effect, wherein the key amino acid is highly conserved. Based on the above, the expression vector is constructed, the mutated primer is designed, the site-directed mutation is utilized to obtain the pullulanase mutant, and the inhibitory effect of the cyclodextrin on the mutant is studied.

DETAILED DESCRIPTION

Figure 1:
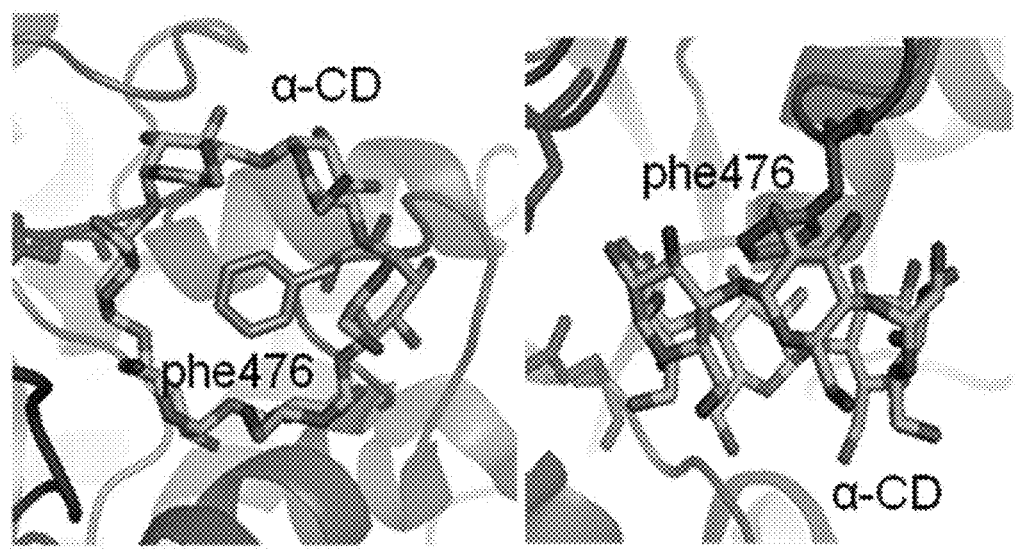
FIG. 1 is a partial schematic diagram of *Bacillus subtilis* pullulanase and cyclodextrin crystal structure.

1. Nickel Affinity Chromatography Comprises the Following Steps:

(1) balancing: balancing a nickel column with 20 mM Tris-HCl, 500 mM NaCl and a buffer solution of which the pH value is 7.5;

(2) sample loading: loading a pretreated sample at a flow rate of 1 mL/min;

(3) cleaning: cleaning impure protein with 20 mM Tris-HCl, 500 mM NaCl and the buffer solution of which the pH value is 7.5; and (4) elution: eluting target protein with 20 mM Tris-HCl, 500 mM NaCl, 300 mM imidazole and the buffer solution of which the pH value is 7.5, enabling the detection wavelength to be 280 nm, and collecting eluent with pullulanase activity, thereby obtaining the purified enzyme of the mutant F476G.

2. Measurement of Enzyme Activity of the Pullulanase:

A 3,5-dinitrosalicylic acid (DNS) method is adopted. The pullulanase catalyzes the hydrolysis of pullulan to produce reducing sugar under certain conditions, 3,5-dinitrosalicylic acid and the reducing sugar are reduced under thermal conditions to produce a brown-red amino complex, the color depth is directly proportional to the amount of the reducing sugar within a certain range, and the measurement can be performed at the wavelength of 540 nm so as to calculate the enzyme activity. Enzyme activity unit definition: the amount of the enzyme that catalyzes the production of the reducing sugar equivalent to 1 μmol of glucose reducing power per minute is defined as one activity unit.

3. Measurement of the Enzyme Activity Comprises the Following Steps:

A. preheating: putting 1 mL of a 1% pullulan solution of which the pH value is 6.0 and 0.1 mL of a buffer solution of which the pH value is 6.0 in a centrifuge tube, and performing thermal insulation for 10 min on a water bath of 40° C.;

B. reaction: adding 0.1 mL (10 U) of an enzyme solution, performing shaking and mixing uniformly, performing accurate timing for 30 min, adding 1.5 mL of DNS for stopping reaction, performing treatment in a boiling water bath for 10 min, and performing instant cooling; and C. measurement: measuring the light absorption value under the condition of 540 nm, and calculating the activity.

Reduction of the Inhibitory Effect of Enzyme Activity Characterization:

A. preheating: putting 1 mL of the 1% pullulan solution of which the pH value is 6.0 and 0.1 mL of 10 mM cyclodextrin in the centrifuge tube, and performing thermal insulation for 10 min on the water bath of 40° C.;

B. reaction: adding 0.1 mL (10 U) of the enzyme solution, performing shaking and mixing uniformly, performing accurate timing for 30 min, adding 1.5 mL of DNS for stopping reaction, performing treatment in the boiling water bath for 10 min, and performing instant cooling; and C. measurement: measuring the light absorption value under the condition of 540 nm, and calculating the activity.

The disclosure is specifically described below in conjunction with accompanying drawings and examples.

Example 1

A process for reasonable mutation and mutation effect analysis of the key amino acid of the pullulanase comprises the following steps:

1. Finding of the Key Amino Acid Related to the Inhibitory Effect:

The crystal structure of the pullulanase derived from *Bacillus subtilis* is analyzed, and the key amino acid F476 related to the inhibitory effect is found, wherein the amino acid has an inclusion relationship with the cyclodextrin structurally; and the gene sequences of the pullulanase from different sources are compared to find that the key amino acid is highly conserved in the pullulanase sequence.

FIG. 1 is a partial schematic diagram of the *Bacillus subtilis* pullulanase and cyclodextrin compound crystal structure. Seen from the figure, a similar inclusion effect exists between the phenylalanine at the position 476 in the pullulanase and the cavity of the cyclodextrin, and the inclusion effect is based on the hydrophobic interaction between the benzene ring of the phenylalanine and the hydrophobic cavity of the cyclodextrin.

2. Acquisition of a Parent Amino Acid Sequence/Nucleotide Sequence (1) The pullulanase (PDB:2E8Z) derived from *Bacillus subtilis* str. 168 in a crystal structure in which the cyclodextrin interacts with the pullulanase is taken as a template, wherein the accession number of the pullulanase on NCBI is CAB14971.2 (SEQ ID NO:2); and a pullulanase gene sequence AmyX is synthesized by adopting a chemical total synthesis method. The plasmids used for constructing an *Escherichia coli* expression vector are pET20b (+) with a T7 promoter.

(2) NcoI and BamI double-enzyme digestion are respectively performed on the pET20b(+) plasmids and the plasmids containing the AmyX gene, the enzyme digestion product is recovered by tapping, then connection is performed with T4 ligase, the connecting product is transformed to *E. coli* DH5α competent cells, culture is performed for 8-12 h at 37° C., transformants are picked into a liquid LB culture medium containing 100 μg/mL ampicillin for shaking culture, the plasmids are extracted, and enzyme digestion verification is performed to obtain an AmyX/Pet20b(+) expression vector.

(3) The plasmids AmyX/Pet20b(+) are transformed into *E. coli* BL21(DE3) host bacteria, an LB panel containing ampicillin (100 mg/mL) is coated with the plasmids, and culture is performed for 8 h at 37° C. to obtain AmyX/Pet20b(+)/BL21(DE3); and a single colony is picked into the liquid LB culture medium, overnight culture is performed at 37° C., and a strain is performed with glycerol.

Figure 2:
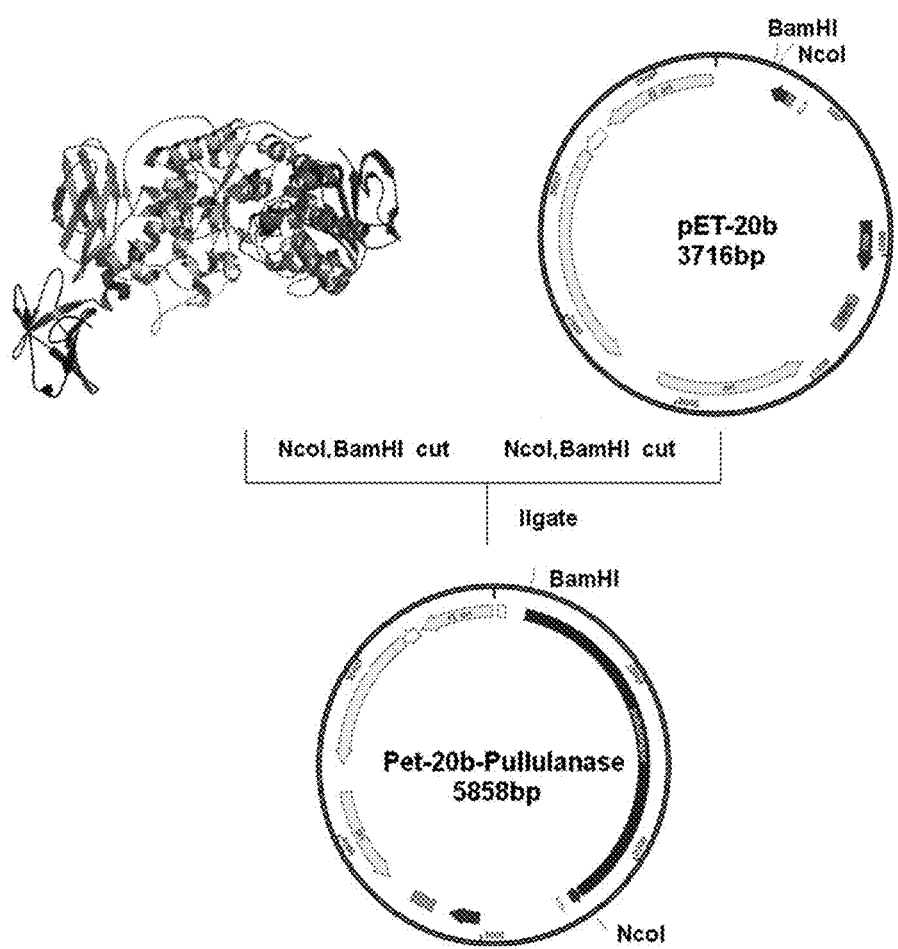
FIG. 2 is a schematic diagram of a plasmid construction process.

FIG. 2 is a schematic diagram of the plasmid construction process. pET-20b(+) plasmids are selected, BamHI and NcoI enzyme digestion sites are selected, and the pullulanase is connected to the plasmids to construct the AmyX/pET-20b (+) expression vector.

3. Construction, Expression and Purification of the Pullulanase Mutant (1) A mutated primer is designed, and the phenylalanine (F) at the position 476 is mutated into glycine (G), wherein mutated primers are as shown in table 1 below:

TABLE 1

F476G-For 5'-cgctgtaaaagggaacaccggtcaccttaaggcaacaggg-3' Shown in SEQ ID NO: 3

F476G-Rev 5'-ccctgttgccttaaggtgaccggtgttccctttttacagcg-3' Shown in SEQ ID NO: 4

Note:
Underlines represent mutated basic groups.

Site-directed mutation is performed by utilizing PCR, wherein a PCR reaction system comprises 10 μL of 5×Primer STAR GXL Buffer, 4 μL of dNTPMixture (2.5 mM), 1.5 μL of a forward primer F476G-For (10 μM), 1.5 μL of a reverse primer F476G-Rev (10 μM), 1 μL of template DNA (10 ng/μL) and 1 μL of Prime STAR GXL DNA Polymerase (1.25μ/μL); double distilled water is added to 50 μL; and PCR amplification conditions are as follows: predegeneration is performed for 3 min at 98° C., then 30 cycles (98° C. 20 s, 60° C. 30 s, 68° C. 6 min) are performed, and extension is continued for 10 min at 68° C.

The PCR product is digested through Dpn I (Thermo Fisher), the digestion product is transformed into *Escherichia coli* DH5α competent cells, overnight culture is performed on the competent cells in an LB solid culture medium (containing 100 μg/mL ampicillin), a single colony is picked into an LB liquid culture medium (containing 100 μg/mL ampicillin) to be cultured, plasmids are extracted, and correctly sequenced plasmids are transformed into expression host *Escherichia coli* BL21(DE3).

(2) A positive single colony transformed into expression host *Escherichia coli* BL21 (DE3) is picked into the LB liquid culture medium (containing 100 μg/mL) to be cultured for 8-12 h at 37° C. and 200 rpm, and inoculation is performed to a TB culture medium (containing 100 μg/mL ampicillin) under the inoculation volume of 5%; and culture is performed at 37° C. and 200 rpm until the OD is equal to 0.6, IPTG of which the final concentration is 0.2 mM is added, induced expression is performed for 96 h at 25° C. and 160 rpm, fermentation liquid is centrifuged at 10000 g for 10 min at 4° C., and the supernatant liquid is collected.

(3) Fermented supernatant liquid is centrifuged at 4000 g with a 10 kDa ultrafiltration centrifuge tube for 10 min, and preliminary concentration and separation are performed; and the concentrated fermentation liquid passes through a 0.22 μm filter membrane, and purification is performed by nickel affinity chromatography, wherein the whole purification process is performed under low temperature conditions.

4. Performance Analysis of the Pullulanase Mutant

Figure 3:
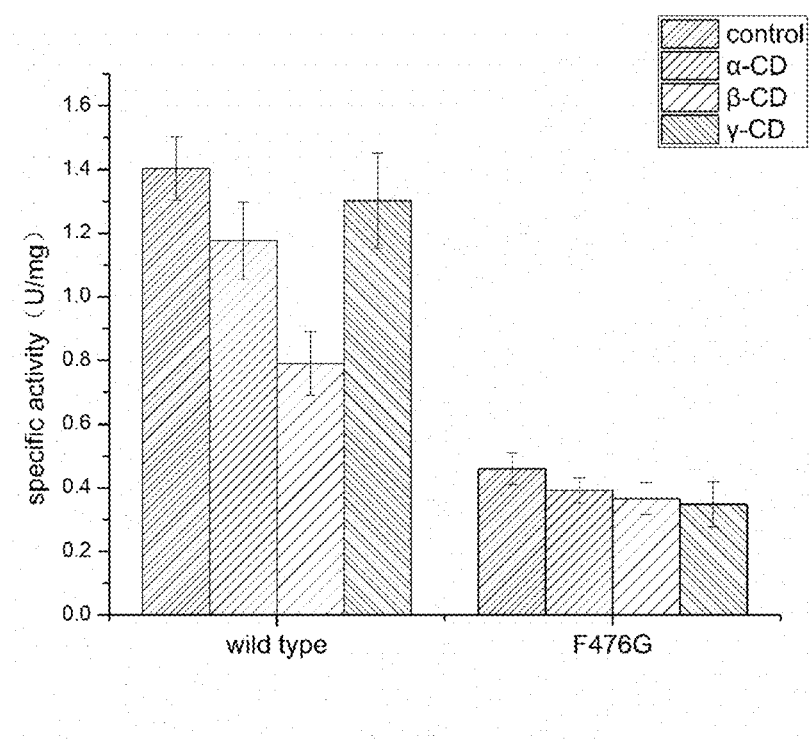
FIG. 3 is enzyme activity characterization of the inhibitory effect of a cyclodextrin on a wild type and a *Bacillus subtilis* pullulanase F476G mutant.

Inhibitory effects are compared, and experimental results are shown in FIG. 3. Comparison of a mutant F476G with a wild type pure enzyme finds that the inhibitory effects of three cyclodextrins on the pullulanase mutant are significantly lower than that of the wild type pullulanase, thereby achieving the purpose of reducing the inhibitory effect of the cyclodextrin on the pullulanase. When an inhibitor α-CD exists, the reduction rate of the specific enzyme activity of the wild type pure enzyme is 14.3%, and the reduction rate of the specific enzyme activity of the mutant F476G is 10.6%; when an inhibitor β-CD exists, the reduction rate of the specific enzyme activity of the wild type pure enzyme is 42.8%, and the reduction rate of the specific enzyme activity of the mutant F476G is 17.1%; and when an inhibitor γ-CD exists, the reduction rate of the specific enzyme activity of the wild type pure enzyme is 7.1%, and the reduction rate of the specific enzyme activity of the mutant F476G is 17.6%.

Example 2

The mutated primer is redesigned by adopting a method similar to example 1, the amino acid (F) at the position 476 is mutated into other amino acids based on the parent of the pullulanase derived from *Bacillus subtilis* str. 168, and expression and purification are performed.

Figure 4:
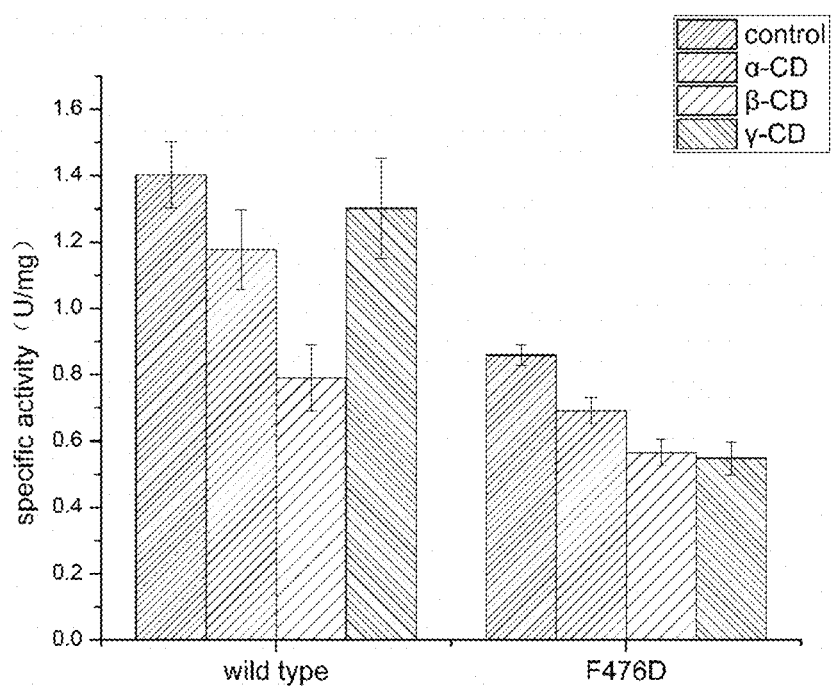
FIG. 4 is enzyme activity characterization of the inhibitory effect of the cyclodextrin on a wild type and a *Bacillus subtilis* pullulanase F476D mutant.

The mutated primer is designed, the phenylalanine (F) at the position 476 is mutated into aspartic acid (D), and a new mutant F476D is constructed, wherein mutated primers are shown in table 2 below:

Inhibitory effects of three cyclodextrins on the wild enzyme and the mutant F476D are compared and analyzed, and experimental results are shown in FIG. 4. Comparison of the mutant with the wild type pure enzyme finds that the inhibitory effects of three cyclodextrins on the pullulanase mutant are significantly lower than that of the wild type pullulanase, thereby achieving the purpose of reducing the inhibitory effect of the cyclodextrin on the pullulanase. When the inhibitor α-CD exists, the reduction rate of the specific enzyme activity of the wild type pure enzyme is 14.3%, and the reduction rate of the specific enzyme activity of the mutant F476D is 5.6%; when the inhibitor β-CD exists, the reduction rate of the specific enzyme activity of the wild type pure enzyme is 42.8%, and the reduction rate of the specific enzyme activity of the mutant F476D is 11.1%; and when the inhibitor γ-CD exists, the reduction rate of the specific enzyme activity of the wild type pure enzyme is 17.1%, and the reduction rate of the specific enzyme activity of the mutant F476D is 11.0%.

Based on the method similar to example 1, the inventors select the pullulanase (PDB:2E8Z) derived from *Bacillus subtilis* str. 168 as a template to mutate the amino acid at the position 476 and also construct mutants F476I, F476M, F476V, F476C and F476A, and the results are shown in table 3.

TABLE 3

Inhibitory conditions of different mutants by cyclodextrin

| | Reduction rate of specific enzyme activity in existence of α-CD | Reduction rate of specific enzyme activity in existence of β-CD | Reduction rate of specific enzyme activity in existence of γ-CD |
|---|---|---|---|
| Wild enzyme | 14.3% | 42.8% | 17.1% |
| Mutant F476I | 8.2% | 21.7% | 15.2% |
| Mutant F476M | 6.5% | 20.6% | 16.1% |
| Mutant F476V | 7.2% | 16.7% | 12.3% |
| Mutant F476C | 4.3% | 17.2% | 5.6% |
| Mutant F476A | 3.5% | 5.6% | 5.8% |

Example 3

The inventors compare the sequences of the pullulanase from 40 different sources and find that non-X amino acids (thickened amino acids) in FNDXXRDXXXGXXF in the sequence (shown in SEQ ID NO:1, wherein X can be any naturally occurring amino acid) are highly conserved, wherein the last position F (phenylalanine) in FNDXXRDXXXGXXF corresponds to the phenylalanine at

TABLE 2

F476D-For 5'-ccctgttgccttaaggt<u>gat</u>cggtgttcccttttacagcg-3' Shown in SEQ ID NO: 5

F476D-Rev 5'-cgctgtaaaagggaacaccg<u>atc</u>accttaaggcaacaggg-3' Shown in SEQ ID NO: 6

Note:
Underlines represent mutated basic groups.

the position 476 of the amino acid sequence of the pullulanase derived from Bacillus subtilis str. 168.

The accession numbers of the sequences of the pullulanase from 40 different sources on NCBI are respectively: WP_003229246.1 (*Bacillus subtilis*)(as shown in SEQ ID NO: 17), WP_024026701.1 (*Bacillus vireti*)(as shown in SEQ ID NO: 18), WP_010789532.1 (*Bacillus atrophaeus*)(as shown in SEQ ID NO: 19), KZE96788.1 (*Geobacillus stearothermophilus*) as shown in SEQ ID NO: 20), WP_032731297.1 (*Bacillus mojavensis*)(as shown in SEQ ID NO: 21), CAA04522.1 (*Thermotoga maritima*)(as shown in SEQ ID NO: 22), OEC77647.1 ([*Brevibacterium*] *halotolerans*)(as shown in SEQ ID NO: 23), AAC15073.1 (*Thermus* sp. IM6501)(as shown in SEQ ID NO: 24), AFQ12130.1 (*Bacillus cereus* FRI-35)(as shown in SEQ ID NO: 25), WP_106020274.1 (*Bacillus halotolerans*)(as shown in SEQ ID NO: 26), AMJ80567.1 (*Alteromonas mediterranea*) as shown in SEQ ID NO: 27), AFU74026.1 (*Klebsiella pneumoniae*)(as shown in SEQ ID NO: 28), CAA04522.1 (*Thermotoga maritima* MSB8)(as shown in SEQ ID NO: 29), OWC08995.1 (*Escherichia coli*)(as shown in SEQ ID NO: 30), AAA25124.1 (*Enterobacter aerogenes*) as shown in SEQ ID NO: 31), WP_010789532.1 (*Bacillus atrophaeus*)(as shown in SEQ ID NO: 32), WP_032731297.1 (*Bacillus mojavensis*)(as shown in SEQ ID NO: 33), WP_095714534.1 (*Bacillus* sp. 7705b)(as shown in SEQ ID NO: 34), WP_024714639.1 (*Bacillus tequilensis*)(as shown in SEQ ID NO: 35), WP_079288107.1 (*Bacillus intestinalis*)(as shown in SEQ ID NO: 36), WP_014114809.1 (*Bacillales*)(as shown in SEQ ID NO: 37), KF103882.1 (*Bacillus* sp. BSC154) as shown in SEQ ID NO: 38), WP_075747083.1 (*Bacillus licheniformis*)(as shown in SEQ ID NO: 39), WP_069840139.1 (*Bacillus* sp. F56)(as shown in SEQ ID NO: 40), WP_014665024.1 (*Bacillus* sp. JS)(as shown in SEQ ID NO: 41), WP_071577010.1 (*Bacillus* sp. FMQ74)(as shown in SEQ ID NO: 41, WP_103749897.1 (*Bacillus* sp. MBGLi97)(as shown in SEQ ID NO: 43), WP_095432444.1 (*Bacillus* sp. X2 (2017))(as shown in SEQ ID NO: 44), OTQ82147.1 (*Bacillus subtilis* subsp. *subtilis*)(as shown in SEQ ID NO: 45), WP_046160744.1 (*Bacillus* sp. CMAA 1185)(as shown in SEQ ID NO: 46), WP_103803268.1 (*Bacillus* sp. Ru63)(as shown in SEQ ID NO: 47), WP_059291821.1 (*Bacillus halotolerans*)(as shown in SEQ ID NO: 48), WP_059335607.1 (*Bacillus halotolerans*)(as shown in SEQ ID NO: 49), WP_069150087.1 (*Bacillus subtilis*) as shown in SEQ ID NO: 50), KFF55698.1 (*Bacillus subtilis*)(as shown in SEQ ID NO: 51), PTU26911.1 (*Bacillus subtilis*)(as shown in SEQ ID NO: 52), WP_061670344.1 (*Bacillus atrophaeus*) as shown in SEQ ID NO: 53), WP_106293419.1 (*Bacillus halotolerans*)(as shown in SEQ ID NO: 54), WP_099043342.1 (*Bacillus halotolerans*) (as shown in SEQ ID NO: 55) and WP_103748328.1 (*Bacillus subtilis*)(as shown in SEQ ID NO: 56).

Specific amino acid fragments (FNDXXRDXXXGXXF) corresponding to the sequences of the pullulanase from 10 different sources are listed below:

TABLE 4

| Source strain | NCBI accession number | Sequence position | Specific amino acid fragment sequence | SEQ ID NO. |
| --- | --- | --- | --- | --- |
| Bacillus subtilis str. 168 | WP_003229246.1 | 463-476 | FNDMFRDAVKGNTF | 7 |
| Bacillus vireti | WP_024026701.1 | 463-476 | FNDKFRDTIKGSTF | 8 |
| Bacillus atrophaeus | WP_010789532.1 | 463-476 | FNDSFRDAVKGSTF | 9 |
| Geobacillus stearothermophilus | KZE96788.1 | 468-481 | FNDRFRDAVKGSTF | 10 |
| Bacillus mojavensis | WP_032731297.1 | 463-476 | FNDSFRDAVKGNTF | 11 |
| Thermotoga maritima MSB8 | CAA04522.1 | 588-601 | FNDEFRDAIRGSVF | 12 |
| [Brevibacterium] halotolerans | OEC77647.1 | 465-478 | FNDSFRDAVKGNTF | 13 |
| Thermus sp. IM6501 | AAC15073.1 | 468-481 | FNDRFRDAVKGSTF | 14 |
| Bacillus cereus FRI-35 | AFQ12130.1 | 600-613 | FNDNIRDGLKGSVF | 15 |
| Bacillus halotolerans | WP_106020274.1 | 463-476 | FNDSFRDAVKGNTF | 16 |

Comparison shows that the site corresponding to the phenylalanine at the position 476 of the pullulanase (PDB: 2E8Z) of *Bacillus subtilis* str. 168 used in the disclosure is highly conserved in the pullulanase from different sources.

On the basis, the phenylalanine at the position 481 of the *Geobacillus stearothermophilus*, the phenylalanine at the position 478 of the [*Brevibacterium*] *halotolerans* and the phenylalanine at the position 476 of the *Bacillus halotolerans* are mutated, obtained mutants and the mutation effects are shown in the table below. The key amino acid site is applicable to the pullulanase from different sources.

TABLE 5

| Source strain | | Reduction rate of specific enzyme activity in existence of α-CD | Reduction rate of specific enzyme activity in existence of β-CD | Reduction rate of specific enzyme activity in existence of γ-CD |
|---|---|---|---|---|
| *Geobacillus stearothermophilus* | Wild enzyme | 16.9% | 51.2% | 7.7% |
| | F481A | 7.1% | 21.5% | 7.1% |
| | F481G | 5.2% | 18.2% | 6.9% |
| [*Brevibacterium*] *halotolerans* | Wild enzyme | 15.3% | 47.2% | 6.1% |
| | F478M | 10.1% | 23.1% | 5.5% |
| | F478G | 6.2% | 16.5% | 4.7% |
| *Bacillus halotolerans* | Wild enzyme | 17.2% | 35.9% | 6.7% |
| | F476A | 15.2% | 12.5% | 5.5% |
| | F476S | 10.7% | 15.2% | 6.1% |

What is claimed is:

1. A pullulanase mutant, wherein the pullulanase mutant comprises a mutation of a phenylalanine (F) at the last position in FNDXXRDXXXGXXF (SEQ ID NO: 1), wherein FNDXXRDXXXGXXF (SEQ ID NO: 1) is a part of a parent pullulanase amino acid sequence, wherein X is any naturally occurring amino acid; wherein an inhibitory effect of a cyclodextrin on the pullulanase mutant is significantly reduced relative to an inhibitory effect on the parent pullulanase, and wherein the cyclodextrin is one or more of α-CD, β-CD and γ-CD, with a reduction rate of 5.6 for the β-CD.

2. The pullulanase mutant of claim 1, wherein the parent pullulanase is obtained from a microorganism selected from the group consisting of: *Bacillus subtilis, Bacillus vireti, Bacillus atrophaeus; Geobacillus stearothermophilus, Bacillus mojavensis, Thermotoga maritima, Brevibacterium halotolerans, Thermus* sp. IM6501, *Bacillus cereus* FRI-35, *Bacillus halotolerans, Alteromonas mediterranea, Klebsiella pneumonia, Thermotoga maritima, Escherichia coli, Enterobacter aerogenes, Bacillus teguilensis, Bacillus intestinalis, Bacillus licheniformis* and *Bacillus halotolerans*.

3. The pullulanase mutant of claim 1, wherein the amino acid sequence of the pullulanase mutant comprises any one of the following:
   (1) a mutation of phenylalanine at the last position in FNDXXRDXXXGXXF (SEQ ID NO: 1) which is position 476 relative to a parent amino acid sequence of a parent pullulanase (SEQ ID NO: 17) obtained from *Bacillus subtilis* str. 168;
   (2) a mutation of phenylalanine at the last position in FNDXXRDXXXGXXF (SEQ ID NO: 1) which is position 476 relative to a parent amino acid sequence of a parent pullulanase (SEQ ID NO: 18) obtained from *Bacillus vireti*;
   (3) a mutation of phenylalanine at the last position in FNDXXRDXXXGXXF (SEQ ID NO: 1) which is position 476 relative to a parent amino acid sequence of a parent pullulanase (SEQ ID NO: 19) obtained from *Bacillus atrophaeus*;
   (4) a mutation of phenylalanine at the last position in FNDXXRDXXXGXXF (SEQ ID NO: 1) which is position 481 relative to a parentamino acid sequence of a parent pullulanase (SEQ ID NO: 20) obtained from *Geobacillus stearothermophilus*;
   (5) a mutation of phenylalanine at the last position in FNDXXRDXXXGXXF (SEQ ID NO: 1) which is position 476 relative to a parent amino acid sequence of a parent pullulanase (SEQ ID NO: 21) obtained from *Bacillus mojavensis*;
   (6) a mutation of phenylalanine at the last position in FNDXXRDXXXGXXF (SEQ ID NO: 1) which is position 601 relative to a parent amino acid sequence of a parent pullulanase (SEQ ID NO: 22) obtained from *Thermotoga maritima*;
   (7) a mutation of phenylalanine at the last position in FNDXXRDXXXGXXF (SEQ ID NO: 1) which is position 478 relative to a parent amino acid sequence of a parent pullulanase (SEQ ID NO: 23) obtained from *Brevibacterium halotolerans*;
   (8) a mutation of phenylalanine at the last position in FNDXXRDXXXGXXF (SEQ ID NO: 1) which is position 481 relative to a parent amino acid sequence of a parent pullulanase (SEQ ID NO: 24) obtained from *Thermus* sp. IM6501;
   (9) a mutation of phenylalanine at the last position in FNDXXRDXXXGXXF (SEQ ID NO: 1) which is position 613 relative to a parent amino acid sequence of a parent pullulanase (SEQ ID NO: 25) obtained from *Bacillus cereus* FRI-35; and
   (10) a mutation of phenylalanine at the last position in FNDXXRDXXXGXXF (SEQ ID NO: 1) which is position 476 relative to a parent amino acid sequence of a parent pullulanase (SEQ ID NO: 26) obtained from *Bacillus halotolerans*.

4. The pullulanase mutant of claim 1, wherein the parent amino acid sequence is set forth in SEQ ID NO: 1.

5. The pullulanase mutant of claim 1, wherein the mutation of the phenylalanine comprises mutation from phenylalanine to any one of the following amino acids: glycine, alanine, leucine, isoleucine, valine, proline, methionine, serine, glutamine, threonine, cysteine, aspartic acid, asparagine, glutamic acid, lysine, arginine or histidine.

* * * * *

SEQUENCE LISTING

<160> NUMBER OF SEQ ID NOS: 56

<210> SEQ ID NO 1
<211> LENGTH: 13
<212> TYPE: PRT
<213> ORGANISM: Artificial sequence
<220> FEATURE:
<223> OTHER INFORMATION: Protein translated from synthetic DNA
<220> FEATURE:
<221> NAME/KEY: ACT_SITE
<222> LOCATION: (4)..(5)
<223> OTHER INFORMATION: Xaa can be any naturally occurring amino acid
<220> FEATURE:
<221> NAME/KEY: ACT_SITE
<222> LOCATION: (8)..(9)
<223> OTHER INFORMATION: Xaa can be any naturally occurring amino acid
<220> FEATURE:
<221> NAME/KEY: ACT_SITE
<222> LOCATION: (11)..(12)
<223> OTHER INFORMATION: Xaa can be any naturally occurring amino acid

<400> SEQUENCE: 1

Phe Asn Asp Xaa Xaa Arg Asp Xaa Xaa Gly Xaa Xaa Phe
1               5                   10

<210> SEQ ID NO 2
<211> LENGTH: 718
<212> TYPE: PRT
<213> ORGANISM: Bacillus subtilis

<400> SEQUENCE: 2

Met Val Ser Ile Arg Arg Ser Phe Glu Ala Tyr Val Asp Asp Met Asn
1               5                   10                  15

Ile Ile Thr Val Leu Ile Pro Ala Glu Gln Lys Glu Ile Met Thr Pro
                20                  25                  30

Pro Phe Arg Leu Glu Thr Glu Ile Thr Asp Phe Pro Leu Ala Val Arg
            35                  40                  45

Glu Glu Tyr Ser Leu Glu Ala Lys Tyr Lys Tyr Val Cys Val Ser Asp
        50                  55                  60

His Pro Val Thr Phe Gly Lys Ile His Cys Val Arg Ala Ser Ser Gly
65                  70                  75                  80

His Lys Thr Asp Leu Gln Ile Gly Ala Val Ile Arg Thr Ala Ala Phe
                85                  90                  95

Asp Asp Glu Phe Tyr Tyr Asp Gly Glu Leu Gly Ala Val Tyr Thr Ala
            100                 105                 110

```
Asp His Thr Val Phe Lys Val Trp Ala Pro Ala Ala Thr Ser Ala Ala
            115                 120                 125

Val Lys Leu Ser His Pro Asn Lys Ser Gly Arg Thr Phe Gln Met Thr
130                 135                 140

Arg Leu Glu Lys Gly Val Tyr Ala Val Thr Val Thr Gly Asp Leu His
145                 150                 155                 160

Gly Tyr Glu Tyr Leu Phe Cys Ile Cys Asn Asn Ser Glu Trp Met Glu
                165                 170                 175

Thr Val Asp Gln Tyr Ala Lys Ala Val Thr Val Asn Gly Glu Lys Gly
            180                 185                 190

Val Val Leu Arg Pro Asp Gln Met Lys Trp Thr Ala Pro Leu Lys Pro
            195                 200                 205

Phe Ser His Pro Val Asp Ala Val Ile Tyr Glu Thr His Leu Arg Asp
210                 215                 220

Phe Ser Ile His Glu Asn Ser Gly Met Ile Asn Lys Gly Lys Tyr Leu
225                 230                 235                 240

Ala Leu Thr Glu Thr Asp Thr Gln Thr Ala Asn Gly Ser Ser Ser Gly
                245                 250                 255

Leu Ala Tyr Val Lys Glu Leu Gly Val Thr His Val Glu Leu Leu Pro
            260                 265                 270

Val Asn Asp Phe Ala Gly Val Asp Glu Glu Lys Pro Leu Asp Ala Tyr
            275                 280                 285

Asn Trp Gly Tyr Asn Pro Leu His Phe Phe Ala Pro Glu Gly Ser Tyr
            290                 295                 300

Ala Ser Asn Pro His Asp Pro Gln Thr Arg Lys Thr Glu Leu Lys Gln
305                 310                 315                 320

Met Ile Asn Thr Leu His Gln His Gly Leu Arg Val Ile Leu Asp Val
                325                 330                 335

Val Phe Asn His Val Tyr Lys Arg Glu Asn Ser Pro Phe Glu Lys Thr
            340                 345                 350

Val Pro Gly Tyr Phe Phe Arg His Asp Glu Cys Gly Met Pro Ser Asn
            355                 360                 365

Gly Thr Gly Val Gly Asn Asp Ile Ala Ser Glu Arg Arg Met Ala Arg
370                 375                 380

Lys Phe Ile Ala Asp Cys Val Val Tyr Trp Leu Glu Glu Tyr Asn Val
385                 390                 395                 400

Asp Gly Phe Arg Phe Asp Leu Leu Gly Ile Leu Asp Ile Asp Thr Val
                405                 410                 415

Leu Tyr Met Lys Glu Lys Ala Thr Lys Ala Lys Pro Gly Ile Leu Leu
            420                 425                 430

Phe Gly Glu Gly Trp Asp Leu Ala Thr Pro Leu Pro His Glu Gln Lys
            435                 440                 445

Ala Ala Leu Ala Asn Ala Pro Arg Met Pro Gly Ile Gly Phe Phe Asn
450                 455                 460

Asp Met Phe Arg Asp Ala Val Lys Gly Asn Thr Phe His Leu Lys Ala
465                 470                 475                 480

Thr Gly Phe Ala Leu Gly Asn Gly Glu Ser Ala Gln Ala Val Met His
                485                 490                 495

Gly Ile Ala Gly Ser Ser Gly Trp Lys Ala Leu Ala Pro Ile Val Pro
            500                 505                 510

Glu Pro Ser Gln Ser Ile Asn Tyr Val Glu Ser His Asp Asn His Thr
            515                 520                 525

Phe Trp Asp Lys Met Ser Phe Ala Leu Pro Gln Glu Asn Asp Ser Arg
```

```
                530                 535                 540
Lys Arg Ser Arg Gln Arg Leu Ala Ala Ala Ile Ile Leu Leu Ala Gln
545                 550                 555                 560

Gly Val Pro Phe Ile His Ser Gly Gln Glu Phe Phe Arg Thr Lys Gln
                565                 570                 575

Gly Val Glu Asn Ser Tyr Gln Ser Ser Asp Ser Ile Asn Gln Leu Asp
                580                 585                 590

Trp Asp Arg Arg Glu Thr Phe Lys Glu Asp Val His Tyr Ile Arg Arg
                595                 600                 605

Leu Ile Ser Leu Arg Lys Ala His Pro Ala Phe Arg Leu Arg Ser Ala
                610                 615                 620

Ala Asp Ile Gln Arg His Leu Glu Cys Leu Thr Leu Lys Glu His Leu
625                 630                 635                 640

Ile Ala Tyr Arg Leu Tyr Asp Leu Asp Glu Val Asp Glu Trp Lys Asp
                645                 650                 655

Ile Ile Val Ile His His Ala Ser Pro Asp Ser Val Glu Trp Arg Leu
                660                 665                 670

Pro Asn Asp Ile Pro Tyr Arg Leu Leu Cys Asp Pro Ser Gly Phe Gln
                675                 680                 685

Glu Asp Pro Thr Glu Ile Lys Lys Thr Val Ala Val Asn Gly Ile Gly
690                 695                 700

Thr Val Ile Leu Tyr Leu Ala Ser Asp Leu Lys Ser Phe Ala
705                 710                 715

<210> SEQ ID NO 3
<211> LENGTH: 40
<212> TYPE: DNA
<213> ORGANISM: Artificial sequence
<220> FEATURE:
<223> OTHER INFORMATION: Synthetic DNA

<400> SEQUENCE: 3
cgctgtaaaa gggaacaccg gtcaccttaa ggcaacaggg                         40

<210> SEQ ID NO 4
<211> LENGTH: 40
<212> TYPE: DNA
<213> ORGANISM: Artificial sequence
<220> FEATURE:
<223> OTHER INFORMATION: Synthetic DNA

<400> SEQUENCE: 4
ccctgttgcc ttaaggtgac cggtgttccc ttttacagcg                         40

<210> SEQ ID NO 5
<211> LENGTH: 40
<212> TYPE: DNA
<213> ORGANISM: Artificial sequence
<220> FEATURE:
<223> OTHER INFORMATION: Synthetic DNA

<400> SEQUENCE: 5
ccctgttgcc ttaaggtgat cggtgttccc ttttacagcg                         40

<210> SEQ ID NO 6
<211> LENGTH: 40
<212> TYPE: DNA
<213> ORGANISM: Artificial sequence
<220> FEATURE:
<223> OTHER INFORMATION: Synthetic DNA
```

```
<400> SEQUENCE: 6
cgctgtaaaa gggaacaccg atcaccttaa ggcaacaggg                                  40

<210> SEQ ID NO 7
<211> LENGTH: 14
<212> TYPE: PRT
<213> ORGANISM: Artificial sequence
<220> FEATURE:
<223> OTHER INFORMATION: Protein translated from synthetic DNA

<400> SEQUENCE: 7

Phe Asn Asp Met Phe Arg Asp Ala Val Lys Gly Asn Thr Phe
1               5                   10

<210> SEQ ID NO 8
<211> LENGTH: 14
<212> TYPE: PRT
<213> ORGANISM: Artificial sequence
<220> FEATURE:
<223> OTHER INFORMATION: Protein translated from synthetic DNA

<400> SEQUENCE: 8

Phe Asn Asp Lys Phe Arg Asp Thr Ile Lys Gly Ser Thr Phe
1               5                   10

<210> SEQ ID NO 9
<211> LENGTH: 14
<212> TYPE: PRT
<213> ORGANISM: Artificial sequence
<220> FEATURE:
<223> OTHER INFORMATION: Protein translated from synthetic DNA

<400> SEQUENCE: 9

Phe Asn Asp Ser Phe Arg Asp Ala Val Lys Gly Ser Thr Phe
1               5                   10

<210> SEQ ID NO 10
<211> LENGTH: 14
<212> TYPE: PRT
<213> ORGANISM: Artificial sequence
<220> FEATURE:
<223> OTHER INFORMATION: Protein translated from synthetic DNA

<400> SEQUENCE: 10

Phe Asn Asp Arg Phe Arg Asp Ala Val Lys Gly Ser Thr Phe
1               5                   10

<210> SEQ ID NO 11
<211> LENGTH: 14
<212> TYPE: PRT
<213> ORGANISM: Artificial sequence
<220> FEATURE:
<223> OTHER INFORMATION: Protein translated from synthetic DNA

<400> SEQUENCE: 11

Phe Asn Asp Ser Phe Arg Asp Ala Val Lys Gly Asn Thr Phe
1               5                   10

<210> SEQ ID NO 12
<211> LENGTH: 14
<212> TYPE: PRT
<213> ORGANISM: Artificial sequence
<220> FEATURE:
<223> OTHER INFORMATION: Protein translated from synthetic DNA

<400> SEQUENCE: 12
```

```
Phe Asn Asp Glu Phe Arg Asp Ala Ile Arg Gly Ser Val Phe
1               5                   10
```

<210> SEQ ID NO 13
<211> LENGTH: 14
<212> TYPE: PRT
<213> ORGANISM: Artificial sequence
<220> FEATURE:
<223> OTHER INFORMATION: Protein translated from synthetic DNA

<400> SEQUENCE: 13

```
Phe Asn Asp Ser Phe Arg Asp Ala Val Lys Gly Asn Thr Phe
1               5                   10
```

<210> SEQ ID NO 14
<211> LENGTH: 14
<212> TYPE: PRT
<213> ORGANISM: Artificial sequence
<220> FEATURE:
<223> OTHER INFORMATION: Protein translated from synthetic DNA

<400> SEQUENCE: 14

```
Phe Asn Asp Arg Phe Arg Asp Ala Val Lys Gly Ser Thr Phe
1               5                   10
```

<210> SEQ ID NO 15
<211> LENGTH: 14
<212> TYPE: PRT
<213> ORGANISM: Artificial sequence
<220> FEATURE:
<223> OTHER INFORMATION: Protein translated from synthetic DNA

<400> SEQUENCE: 15

```
Phe Asn Asp Asn Ile Arg Asp Gly Leu Lys Gly Ser Val Phe
1               5                   10
```

<210> SEQ ID NO 16
<211> LENGTH: 14
<212> TYPE: PRT
<213> ORGANISM: Artificial sequence
<220> FEATURE:
<223> OTHER INFORMATION: Protein translated from synthetic DNA

<400> SEQUENCE: 16

```
Phe Asn Asp Ser Phe Arg Asp Ala Val Lys Gly Asn Thr Phe
1               5                   10
```

<210> SEQ ID NO 17
<211> LENGTH: 718
<212> TYPE: PRT
<213> ORGANISM: Bacillus subtilis

<400> SEQUENCE: 17

```
Met Val Ser Ile Arg Arg Ser Phe Glu Ala Tyr Val Asp Asp Met Asn
1               5                   10                  15

Ile Ile Thr Val Leu Ile Pro Ala Glu Gln Lys Glu Ile Met Thr Pro
            20                  25                  30

Pro Phe Arg Leu Glu Thr Glu Ile Thr Asp Phe Pro Leu Ala Val Arg
        35                  40                  45

Glu Glu Tyr Ser Leu Glu Ala Lys Tyr Lys Tyr Val Cys Val Ser Asp
    50                  55                  60

His Pro Val Thr Phe Gly Lys Ile His Cys Val Arg Ala Ser Ser Gly
65                  70                  75                  80

His Lys Thr Asp Leu Gln Ile Gly Ala Val Ile Arg Thr Ala Ala Phe
```

```
                    85                  90                  95
Asp Asp Glu Phe Tyr Tyr Asp Gly Glu Leu Gly Ala Val Tyr Thr Ala
                100                 105                 110
Asp His Thr Val Phe Lys Val Trp Ala Pro Ala Ala Thr Ser Ala Ala
                115                 120                 125
Val Lys Leu Ser His Pro Asn Lys Ser Gly Arg Thr Phe Gln Met Thr
                130                 135                 140
Arg Leu Glu Lys Gly Val Tyr Ala Val Thr Val Thr Gly Asp Leu His
145                 150                 155                 160
Gly Tyr Glu Tyr Leu Phe Cys Ile Cys Asn Asn Ser Glu Trp Met Glu
                165                 170                 175
Thr Val Asp Gln Tyr Ala Lys Ala Val Thr Val Asn Gly Glu Lys Gly
                180                 185                 190
Val Val Leu Arg Pro Asp Gln Met Lys Trp Thr Ala Pro Leu Lys Pro
                195                 200                 205
Phe Ser His Pro Val Asp Ala Val Ile Tyr Glu Thr His Leu Arg Asp
                210                 215                 220
Phe Ser Ile His Glu Asn Ser Gly Met Ile Asn Lys Gly Lys Tyr Leu
225                 230                 235                 240
Ala Leu Thr Glu Thr Asp Thr Gln Thr Ala Asn Gly Ser Ser Ser Gly
                245                 250                 255
Leu Ala Tyr Val Lys Glu Leu Gly Val Thr His Val Glu Leu Leu Pro
                260                 265                 270
Val Asn Asp Phe Ala Gly Val Asp Glu Glu Lys Pro Leu Asp Ala Tyr
                275                 280                 285
Asn Trp Gly Tyr Asn Pro Leu His Phe Phe Ala Pro Glu Gly Ser Tyr
                290                 295                 300
Ala Ser Asn Pro His Asp Pro Gln Thr Arg Lys Thr Glu Leu Lys Gln
305                 310                 315                 320
Met Ile Asn Thr Leu His Gln His Gly Leu Arg Val Ile Leu Asp Val
                325                 330                 335
Val Phe Asn His Val Tyr Lys Arg Glu Asn Ser Pro Phe Glu Lys Thr
                340                 345                 350
Val Pro Gly Tyr Phe Phe Arg His Asp Glu Cys Gly Met Pro Ser Asn
                355                 360                 365
Gly Thr Gly Val Gly Asn Asp Ile Ala Ser Glu Arg Arg Met Ala Arg
                370                 375                 380
Lys Phe Ile Ala Asp Cys Val Val Tyr Trp Leu Glu Glu Tyr Asn Val
385                 390                 395                 400
Asp Gly Phe Arg Phe Asp Leu Leu Gly Ile Leu Asp Ile Asp Thr Val
                405                 410                 415
Leu Tyr Met Lys Glu Lys Ala Thr Lys Ala Lys Pro Gly Ile Leu Leu
                420                 425                 430
Phe Gly Glu Gly Trp Asp Leu Ala Thr Pro Leu Pro His Glu Gln Lys
                435                 440                 445
Ala Ala Leu Ala Asn Ala Pro Arg Met Pro Gly Ile Gly Phe Phe Asn
                450                 455                 460
Asp Met Phe Arg Asp Ala Val Lys Gly Asn Thr Phe His Leu Lys Ala
465                 470                 475                 480
Thr Gly Phe Ala Leu Gly Asn Gly Glu Ser Ala Gln Ala Val Met His
                485                 490                 495
Gly Ile Ala Gly Ser Ser Gly Trp Lys Ala Leu Ala Pro Ile Val Pro
                500                 505                 510
```

```
Glu Pro Ser Gln Ser Ile Asn Tyr Val Glu Ser His Asp Asn His Thr
            515                 520                 525

Phe Trp Asp Lys Met Ser Phe Ala Leu Pro Gln Glu Asn Asp Ser Arg
    530                 535                 540

Lys Arg Ser Arg Gln Arg Leu Ala Ala Ile Ile Leu Leu Ala Gln
545                 550                 555                 560

Gly Val Pro Phe Ile His Ser Gly Gln Glu Phe Phe Arg Thr Lys Gln
                565                 570                 575

Gly Val Glu Asn Ser Tyr Gln Ser Ser Asp Ser Ile Asn Gln Leu Asp
            580                 585                 590

Trp Asp Arg Arg Glu Thr Phe Lys Glu Asp Val His Tyr Ile Arg Arg
            595                 600                 605

Leu Ile Ser Leu Arg Lys Ala His Pro Ala Phe Arg Leu Arg Ser Ala
        610                 615                 620

Ala Asp Ile Gln Arg His Leu Glu Cys Leu Thr Leu Lys Glu His Leu
625                 630                 635                 640

Ile Ala Tyr Arg Leu Tyr Asp Leu Asp Glu Val Asp Glu Trp Lys Asp
                645                 650                 655

Ile Ile Val Ile His His Ala Ser Pro Asp Ser Val Gly Trp Arg Leu
                660                 665                 670

Pro Asn Asp Ile Pro Tyr Arg Leu Leu Cys Asp Pro Ser Gly Phe Gln
            675                 680                 685

Glu Asp Pro Thr Glu Ile Lys Lys Thr Val Ala Val Asn Gly Ile Gly
        690                 695                 700

Thr Val Ile Leu Tyr Leu Ala Ser Asp Leu Lys Ser Phe Ala
705                 710                 715

<210> SEQ ID NO 18
<211> LENGTH: 708
<212> TYPE: PRT
<213> ORGANISM: Unknown
<220> FEATURE:
<223> OTHER INFORMATION: bacterial

<400> SEQUENCE: 18

Met Ile Ala Thr Asp Arg Asn Phe Leu Ala Tyr Leu Asp Glu Leu Thr
1               5                   10                  15

Ile Ile Thr Ile Leu Leu Pro Leu Ser Tyr His Gln Gly Val Ser Ala
            20                  25                  30

Ser Phe Tyr Leu Ile Asp His Ser Gly Lys Ser Pro Leu Ser Ile Leu
        35                  40                  45

Ser Ile Asn Gln Ile Glu Lys Asn Gln Lys Tyr Ile Cys Arg Leu Glu
50                  55                  60

Val Asp Ile Ser Phe Gly Lys Gln Tyr Trp Ile Met Asp Glu His Gly
65                  70                  75                  80

Gly Lys Thr Asp Leu Gln Ile Gly Ala Val Ile Arg Thr Glu Ser Phe
                85                  90                  95

Asp His Leu Phe Tyr Tyr Glu Gly Asn Asp Leu Gly Val Thr Tyr Asp
            100                 105                 110

Ala Asn Leu Thr Arg Phe Lys Leu Trp Ala Pro Thr Ala Thr Gln Val
        115                 120                 125

Lys Leu Lys Leu Phe Leu Pro Asn Ser His Phe Ser Glu Ile Ile Lys
130                 135                 140

Met Lys Arg Glu Asp Phe Gly Val Trp Ser Val Gly Ile Tyr Arg Glu
145                 150                 155                 160
```

-continued

Leu Glu Ser Phe Gln Tyr Arg Phe Leu Val Gln Val Asn Gln Glu Trp
                165                 170                 175

Arg Glu Ala Val Asp Pro Tyr Ala Lys Ala Val Thr Val Asn Gly Glu
            180                 185                 190

Lys Gly Val Ile Val Lys Leu Glu Lys Thr Arg Lys Thr Lys Pro Val
        195                 200                 205

Leu Pro Pro Ile Glu Ser Pro Val Asp Met Ile Ile Tyr Glu Thr His
    210                 215                 220

Ile Arg Asp Phe Thr Ile His Glu Asn Ser Gly Ile Ile Asp Lys Gly
225                 230                 235                 240

Leu Tyr Leu Gly Ala Gly Glu Leu Asn Thr Lys Gly Lys Gly Gly Gly
                245                 250                 255

Lys Thr Gly Leu Ser Tyr Val Lys Asp Leu Gly Ile Thr His Ile Glu
            260                 265                 270

Phe Leu Pro Phe Asn Asp Phe Ala Gly Ile Asp Glu Gln Glu Arg Asn
        275                 280                 285

Lys Ser Tyr Asn Trp Gly Tyr Asn Pro Leu His Phe Asn Ala Pro Glu
    290                 295                 300

Gly Ser Phe Ser Thr Asp Pro Leu Asn Pro Tyr Ala Arg Ile Ile Glu
305                 310                 315                 320

Leu Lys Gln Leu Ile Glu Lys Ile His Gln Ser Gly Leu Arg Val Ile
                325                 330                 335

Met Asp Ala Val Tyr Asn His Val Tyr Ile Arg Glu Thr Ser Ser Phe
            340                 345                 350

Glu Ser Ile Val Pro Gly Tyr Tyr Phe Arg His Asn Glu Met Gly Leu
        355                 360                 365

Pro Ser Asn Gly Thr Gly Val Gly Asn Asp Ile Ala Ser Glu Arg Lys
    370                 375                 380

Met Val Arg Lys Phe Ile Val Asp Ser Leu Arg Tyr Trp Gln Glu Glu
385                 390                 395                 400

Tyr Gly Ile Asp Gly Phe Arg Phe Asp Leu Met Gly Ile Leu Asp Val
                405                 410                 415

Thr Thr Ile Ser Glu Val Cys Glu Ser Leu Arg Gln Gly Thr Ile Leu
            420                 425                 430

Leu Gly Glu Gly Trp Asn Leu Asn Thr Pro Leu Pro Pro Glu Gln Lys
        435                 440                 445

Ala Met Ile Ala Asn His Ala Lys Ile Pro Arg Val Ala Met Phe Asn
    450                 455                 460

Asp Lys Phe Arg Asp Thr Ile Lys Gly Ser Thr Phe Asn Leu Phe Asp
465                 470                 475                 480

Lys Gly Phe Ala Leu Gly Asn Glu His His Ile Glu Thr Ala Leu Glu
                485                 490                 495

Val Ile Thr Gly Ser Ile Gly Phe Lys Lys His Glu Asn Arg Leu Phe
            500                 505                 510

Asn Glu Pro Tyr Gln Ser Val Asn Tyr Ile Glu Cys His Asp Asn His
        515                 520                 525

Thr Leu Trp Asp Lys Leu Leu Ser Cys Leu Pro Asp Ala Asn Asp Leu
    530                 535                 540

Thr Arg Met Lys Tyr His Arg Leu Ala Thr Gly Ile Val Leu Leu Ser
545                 550                 555                 560

Gln Gly Ile Pro Phe Leu His Ser Gly Gln Glu Phe Phe Arg Thr Lys
                565                 570                 575

```
Gln Gly Asp Gly Asn Ser Tyr Arg Ser Ser Asn Glu Ile Asn Gln Leu
            580                 585                 590

Asp Trp Asp Arg Lys Ser Glu Phe Ile Glu Asn Val Asn Tyr Leu Lys
        595                 600                 605

Gly Leu Ile Gln Ile Arg Lys Ser Phe Ser Cys Phe Arg Met Arg Thr
        610                 615                 620

Ala Gly Glu Ile Arg Ser Gln Ile Gln Pro Leu Ser Thr Ala Pro Pro
625                 630                 635                 640

Leu Leu Gly Cys Leu Leu Asn Lys Asp Ser Asn Glu Leu Ile Leu Leu
                645                 650                 655

Ile Asn Pro Ser Leu Lys Gln Gln Thr Val Ser Leu Pro Glu Gly Asp
            660                 665                 670

Trp Ser Ile Leu Ala Asp His Asp Tyr Ala Gly Ile Ser Ser Lys Ala
        675                 680                 685

Ala Thr Val Lys Glu Glu Leu Thr Ile Asp Ser Val Ser Leu Asn Val
690                 695                 700

Leu Leu Lys Lys
705

<210> SEQ ID NO 19
<211> LENGTH: 710
<212> TYPE: PRT
<213> ORGANISM: Bacillus atrophaeus

<400> SEQUENCE: 19

Met Val Cys Leu Asn Arg Lys Phe Glu Ala Tyr Leu Asp Glu Met Asp
1               5                   10                  15

Val Ile Thr Val Leu Ile Pro Ser Gly Lys Lys Glu Lys Tyr Thr Leu
            20                  25                  30

Pro Phe Val Leu Glu Thr Glu Ala Gly Asp Val Ser Leu Ser Ile Arg
        35                  40                  45

Ala Glu Cys His Ile Asp Gly Lys Tyr Lys Tyr Ile Leu Val Ser Glu
    50                  55                  60

His Pro Val Ser Leu Gly Lys Thr His Tyr Ile Arg Ala Ser Gly Gly
65                  70                  75                  80

Asp Lys Thr Asp Leu Gln Ile Gly Ala Val Ile Arg Thr Glu Ala Phe
                85                  90                  95

Asp Ser Gln Phe Tyr Phe Asp Gly Ala Leu Gly Ala Asp Tyr Thr Pro
            100                 105                 110

Ser Arg Thr Val Phe Lys Val Trp Ala Pro Thr Ala Thr Ala Thr Ala
        115                 120                 125

Val Lys Leu Thr His Pro Glu Gln Gln Gly Leu Val Leu Gln Met Thr
    130                 135                 140

Arg Gln Asp His Gly Val Phe Ala Ala Leu Val Asp Gly Asp Leu His
145                 150                 155                 160

Gly Tyr Glu Tyr Val Tyr Arg Ile Cys Asn Asn Leu Glu Trp Thr Glu
                165                 170                 175

Thr Val Asp Pro Tyr Ala Lys Ala Val Thr Ile Asn Gly Glu Lys Gly
            180                 185                 190

Val Val Leu Arg Pro Glu Asn Pro His Ile Thr Ser Gln Gly Ile Pro
        195                 200                 205

Phe Ser Asn Pro Ala Asp Ala Val Ile Tyr Glu Leu His Ile Arg Asp
    210                 215                 220

Phe Ser Ile His Glu Asn Ser Gly Met Lys Lys Lys Gly Gln Tyr Leu
225                 230                 235                 240
```

```
Ala Met Thr Glu Thr Asp Ala Lys Thr Gln Glu Gly Val Ser Ala Gly
            245                 250                 255
Leu Ser Tyr Leu Lys Glu Leu Gly Val Thr His Ile Glu Leu Leu Pro
            260                 265                 270
Val Asn Asp Phe Ala Gly Val Asp Glu Lys Asn Pro Leu Ala Ala Tyr
            275                 280                 285
Asn Trp Gly Tyr Asn Pro Leu His Phe Phe Ala Pro Glu Gly Ser Tyr
            290                 295                 300
Ser Ser Asp Pro Tyr Asn Pro Gln Val Arg Lys Ser Glu Leu Lys Glu
305                 310                 315                 320
Leu Ile Gln Thr Leu His Gln Asn Gly Leu Gln Val Ile Leu Asp Val
            325                 330                 335
Val Tyr Asn His Val Tyr Lys Arg Glu His Ser Pro Phe Glu Asn Thr
            340                 345                 350
Val Pro Gly Tyr Phe Phe Arg His Asp Ala Asp Gly Met Pro Ser Asn
            355                 360                 365
Gly Thr Gly Val Gly Asn Asp Ile Ala Ser Glu Arg Leu Met Ala Arg
            370                 375                 380
Lys Tyr Ile Ile Asp Cys Val His Trp Leu Lys Glu Tyr Asp Ala
385                 390                 395                 400
Asp Gly Phe Arg Phe Asp Leu Met Gly Ile Leu Asp Ile Asp Thr Ile
            405                 410                 415
Arg Gln Ile Arg Glu Arg Ala Leu Ala Val Lys Pro Gly Ile Leu Leu
            420                 425                 430
Phe Gly Glu Gly Trp Asn Leu Asp Thr Pro Ile Ser Asp Asp Lys Lys
            435                 440                 445
Ala Thr Leu Ala Asn Ala Phe Gln Leu Pro Gly Ile Gly Phe Phe Asn
            450                 455                 460
Asp Ser Phe Arg Asp Ala Val Lys Gly Ser Thr Phe Gln Arg Glu Ala
465                 470                 475                 480
Ala Gly Phe Ala Leu Gly Asn Gly Asp Gln Ile Asp Ala Val Ile His
            485                 490                 495
Gly Ile Thr Gly Ser Ala Gly Trp Lys Glu Thr Asp Pro Ile Val Gln
            500                 505                 510
Glu Pro Ser Gln Ser Val Asn Tyr Val Glu Ser His Asp Asn His Thr
            515                 520                 525
Phe Trp Asp Lys Met Gln Tyr Ala Leu Pro His Glu Thr Asp Ser Val
            530                 535                 540
Lys Arg Ser Arg Gln Lys Leu Ala Thr Ala Val Val Leu Leu Ala Gln
545                 550                 555                 560
Gly Ile Pro Phe Ile His Ser Gly Gln Glu Phe Phe Arg Thr Lys Gln
            565                 570                 575
Gly Asp Glu Asn Ser Tyr Gln Ser Gly Asp Ser Val Asn Arg Leu Asp
            580                 585                 590
Trp Thr Arg Arg Ser Glu Phe Arg Glu Asp Val Glu Tyr Val Arg Arg
            595                 600                 605
Leu Ile Glu Ile Arg Lys Ala His Pro Ala Phe Arg Leu Lys Arg Ala
            610                 615                 620
Ala Glu Val Val Arg His Leu Asp Phe Leu Glu Ala Arg Gly His Leu
625                 630                 635                 640
Ile Ala Tyr Arg Leu Phe Asp Leu Glu Ala Met Asp Glu Trp Lys Glu
            645                 650                 655
```

```
Ile Ile Ile Val His His Ser Ser Pro Asp Lys Ala Glu Met Met Leu
            660                 665                 670

Pro Ala Gly Lys Thr Tyr Arg Leu Leu Cys Asp Pro Ser Gly Phe Arg
            675                 680                 685

Glu Gln Pro Lys Glu Ile Lys Glu Glu Leu Ile Ile Glu Gly Ile Gly
            690                 695                 700

Thr Cys Ile Leu Tyr Ile
705                 710

<210> SEQ ID NO 20
<211> LENGTH: 726
<212> TYPE: PRT
<213> ORGANISM: Unknown
<220> FEATURE:
<223> OTHER INFORMATION: bacterial

<400> SEQUENCE: 20

Met Leu His Ile Ser Arg Thr Phe Ala Ala Tyr Leu Asp Glu Ile Asp
1               5                   10                  15

Gln Ile Thr Val Ile Val Pro Lys Ala Arg Cys Leu Asp Asn Met Glu
            20                  25                  30

Pro Phe Val Met Thr Ala Pro Ser Gly Glu Asp Ile Pro Leu Val Val
            35                  40                  45

Gln Gln Lys Glu Asp Leu Gly Asp Ala Val Lys Tyr Val Cys Arg Phe
    50                  55                  60

Ser Val Pro Phe Gln Ile Gly Glu Thr His Trp Ile Arg Ala Arg Ser
65                  70                  75                  80

Gly Glu Glu Ser Asp Val Gln Ile Gly Ala Val Val Arg Thr Ala Ala
                85                  90                  95

Phe Asp Asp Gln Phe Phe Tyr Asp Gly Lys Leu Gly Val Glu Tyr Ala
            100                 105                 110

Lys Glu Gln Thr Ile Phe Arg Val Trp Ala Pro Thr Ala Thr Ala Val
            115                 120                 125

Ser Val Lys Leu Val His Pro Asp His Gly Asp Val Arg Tyr Val Pro
    130                 135                 140

Leu Val Arg Gly Glu Arg Gly Val Trp Ser Val Ala Val Ser Gly Asp
145                 150                 155                 160

Trp Glu Arg Ala Arg Tyr Met Tyr Val Ala Cys Ile Asn Arg Val Trp
                165                 170                 175

Arg Glu Ala Val Asp Pro Tyr Ala Thr Ala Val Ser Val Asn Gly Glu
            180                 185                 190

His Gly Val Ile Val Asp Trp Glu Lys Thr Lys Leu Ala Lys Pro Ala
            195                 200                 205

Pro Pro Leu Pro Pro Cys Pro Ser Pro Thr Asp Ala Val Ile Tyr Glu
    210                 215                 220

Leu Ser Ile Arg Asp Phe Thr Ser His Pro Asp Ser Gly Ala Val Trp
225                 230                 235                 240

Lys Gly Lys Tyr Leu Gly Leu Thr Glu Glu His Thr Arg Gly Pro Asn
                245                 250                 255

Gly Thr Val Thr Gly Leu Ser Tyr Leu Lys Glu Leu Gly Val Thr His
            260                 265                 270

Val Gln Leu Met Pro Phe Ala Asp Phe Ala Gly Val Asp Glu Arg Asp
    275                 280                 285

Pro Gln Ala Ala Tyr Asn Trp Gly Tyr Asn Pro Leu His Leu Tyr Ala
    290                 295                 300
```

-continued

```
Pro Glu Gly Ser Tyr Ala Thr Asp Pro His Asp Pro Tyr Ala Arg Ile
305                 310                 315                 320

Val Glu Leu Lys Gln Ala Ile Arg Ala Leu Gln Glu Asn Gly Leu Arg
            325                 330                 335

Val Val Met Asp Ala Val Tyr Asn His Val Tyr Asp Arg Glu Gln Ser
            340                 345                 350

Pro Leu Glu Asn Leu Val Pro Gly Tyr Tyr Phe Arg Tyr Asp Ala Tyr
            355                 360                 365

Gly Arg Pro Ala Asn Gly Thr Gly Val Gly Asn Asp Ile Ala Ser Glu
            370                 375                 380

Arg Arg Met Ala Arg Arg Trp Ile Val Asp Ser Val Val Phe Trp Ala
385                 390                 395                 400

Lys Glu Tyr Gly Ile Asn Gly Phe Arg Phe Asp Leu Met Gly Val His
                405                 410                 415

Asp Ile Glu Thr Met Lys Ser Val Arg Asp Ala Leu Asp Ala Ile Asp
                420                 425                 430

Pro Ser Ile Leu Val Tyr Gly Glu Gly Trp Asp Leu Pro Thr Pro Leu
            435                 440                 445

Ala Pro Glu Gln Lys Ala Thr Met Ala Asn Ala Lys Arg Leu Pro Arg
450                 455                 460

Leu Ala Tyr Phe Asn Asp Arg Phe Arg Asp Ala Val Lys Gly Ser Thr
465                 470                 475                 480

Phe Tyr Leu Pro Asp Arg Gly Phe Ala Leu Gly Asp Ser Ala Gly Arg
                485                 490                 495

Glu Gln Val Lys Thr Ala Ile Ala Gly Ser Leu Gln Ala Phe Gly Gly
            500                 505                 510

Leu Phe Cys His Pro Leu Gln Ser Ile Asn Tyr Val Glu Cys His Asp
            515                 520                 525

Asn His Thr Phe Trp Asp Lys Met Glu Ala Ala Asn Gly His Glu Pro
530                 535                 540

Glu Trp Leu Arg Arg Lys Arg Gln Lys Leu Ala Thr Ala Ile Val Leu
545                 550                 555                 560

Leu Ala Gln Gly Ile Pro Phe Leu His Ser Gly Gln Glu Phe Tyr Arg
                565                 570                 575

Thr Lys Gly Gly Asp Glu Asn Ser Tyr Arg Ser Pro Asp Ala Val Asn
            580                 585                 590

Arg Leu Asp Trp Glu Arg Lys Ser Arg Tyr Glu Asp Val Arg Tyr
            595                 600                 605

Ile Gln Gly Leu Ile Ala Ile Arg Arg Ala His Gly Ala Phe Arg Leu
610                 615                 620

Ala Thr Glu Val Asp Val Gln Arg His Leu Thr Phe Leu Glu Pro Ile
625                 630                 635                 640

Pro Pro Ser Val Ile Ala Tyr Trp Leu Arg Asp Val Ala Leu Tyr Gly
                645                 650                 655

Leu Trp Thr Asp Ile Val Ile His His Asn Glu Glu Thr Gly Val
            660                 665                 670

Val Ile Ala Leu Pro Asp Asp Gly Glu Trp His Val Cys Asp Gly
            675                 680                 685

Glu Arg Ser Gly Thr Val Pro Leu Arg Gln Val Arg Arg Phe Leu Asp
            690                 695                 700

Ala Asp Gly Ile Gly Thr Trp Val Leu Val Lys Thr Gly Ala Ala Ala
705                 710                 715                 720

Asp Val Glu Asn Gly Lys
```

725

<210> SEQ ID NO 21
<211> LENGTH: 711
<212> TYPE: PRT
<213> ORGANISM: Unknown
<220> FEATURE:
<223> OTHER INFORMATION: bacterial

<400> SEQUENCE: 21

Met Val Ser Ile Gln Arg Arg Phe Glu Ala Tyr Ala Asp Glu Met Asn
1               5                   10                  15

Ile Ile Thr Val Leu Ile Pro Ala Asp Gln Lys Asp Thr Phe Thr Pro
            20                  25                  30

Pro Phe Gln Leu Glu Thr Asp Thr Gly Glu Ile Pro Leu Thr Val Ser
        35                  40                  45

Gln Glu Trp Lys Ile Glu Gly Lys Tyr Lys Tyr Val Cys Val Ala Glu
    50                  55                  60

Gln Pro Val Thr Phe Gly Lys Thr His Tyr Val Lys Ala Ser Gly Gly
65                  70                  75                  80

Gly Val Thr Asp Leu Gln Ile Gly Ala Val Ile Arg Thr Asp Pro Phe
                85                  90                  95

Asp Ala Ala Phe Tyr Tyr Asp Gly Glu Leu Gly Ala Val Tyr Thr Ser
            100                 105                 110

Asp Tyr Thr Glu Phe Lys Val Trp Ala Pro Ala Ala Thr Ser Ala Ala
        115                 120                 125

Val Lys Leu Ser His Pro Glu Lys Ser Gly His Thr Phe Gln Met Thr
    130                 135                 140

Arg Met Glu Asn Gly Val Tyr Ala Val Thr Val Val Gly Asp Leu His
145                 150                 155                 160

Gly Tyr Glu Tyr Val Tyr Trp Ile Cys Asn Asn Leu Glu Trp Thr Glu
                165                 170                 175

Thr Val Asp Pro Tyr Ala Lys Ala Val Thr Val Asn Gly Glu Lys Gly
            180                 185                 190

Val Val Leu Arg Pro Asp Gln Ala Asn Ser Ala Pro Ser Leu Thr Pro
        195                 200                 205

Phe Ser Asp Pro Val Asp Ala Ile Ile Tyr Glu Met His Val Arg Asp
    210                 215                 220

Phe Ser Ile His Glu Asn Ser Gly Met Lys Asn Lys Gly Lys Tyr Ala
225                 230                 235                 240

Ala Leu Ala Glu Thr Gly Thr Gln Thr Lys Asn Gly Ser Ser Thr Gly
                245                 250                 255

Leu Ser Tyr Leu Lys Glu Leu Gly Val Thr His Ile Glu Leu Leu Pro
            260                 265                 270

Val Asn Asp Tyr Ala Gly Val Asn Glu Glu Thr Pro Leu Ala Ala Tyr
        275                 280                 285

Asn Trp Gly Tyr Asn Pro Leu His Phe Phe Ala Pro Glu Gly Ser Tyr
    290                 295                 300

Ala Ser Asn Pro His Asp Pro Gln Thr Arg Asn Lys Glu Val Lys Gln
305                 310                 315                 320

Met Ile His Thr Leu His Arg His Gly Leu Arg Val Ile Leu Asp Val
                325                 330                 335

Val Tyr Asn His Val Tyr Gln Arg Glu His Ser Pro Phe Glu Lys Thr
            340                 345                 350

Val Pro Gly Tyr Phe Phe Arg His Asp Gln Phe Gly Met Pro Ser Asn

-continued

```
                355                 360                 365
Gly Thr Gly Val Gly Asn Asp Ile Ala Ser Glu Arg Arg Met Ala Arg
            370                 375                 380

Lys Phe Ile Thr Asp Cys Val Leu Tyr Trp Leu Lys Glu Tyr Asp Val
385                 390                 395                 400

Asp Gly Phe Arg Phe Asp Leu Leu Gly Ile Leu Asp Ile Glu Thr Val
                405                 410                 415

Leu His Ile Lys Glu Lys Ala Phe Glu Val Lys Pro Gly Ile Leu Leu
            420                 425                 430

Phe Gly Glu Gly Trp Asp Leu Ala Thr Pro Leu Pro Asp Gln Lys
                435                 440                 445

Ala Thr Leu Ala Asn Ala Ser Lys Met Pro Gly Val Gly Phe Phe Asn
            450                 455                 460

Asp Ser Phe Arg Asp Ala Val Lys Gly Asn Thr Phe Gln Ile Ala Ala
465                 470                 475                 480

Ala Gly Phe Ala Leu Gly Asn Gly Glu Lys Ala Glu Thr Val Met His
                485                 490                 495

Gly Ile Ala Gly Ser Ser Gly Trp Lys Glu Thr Ala Pro Leu Val Ser
            500                 505                 510

Ala Pro Ser Gln Ser Ile Asn Tyr Val Glu Ser His Asp Asn His Thr
515                 520                 525

Phe Trp Asp Lys Met Ser Leu Ala Leu Pro Gln Glu Ser Asp Ser Arg
            530                 535                 540

Lys Arg Ser Arg Gln Lys Leu Ala Thr Ala Ile Ile Leu Leu Ala Gln
545                 550                 555                 560

Gly Val Pro Phe Ile His Ser Gly Gln Glu Phe Arg Thr Lys Gln
                565                 570                 575

Gly Val Glu Asn Ser Tyr Gln Ser Ser Asp Ser Ile Asn Gln Leu Asp
            580                 585                 590

Trp Ser Arg Arg Glu Thr Phe Met Gln Asp Ala Asp Tyr Val Arg Lys
                595                 600                 605

Leu Ile Ser Leu Arg Lys Ala His Pro Ala Phe Arg Leu Thr Ser Ser
610                 615                 620

Ala Asp Ile Gln Arg Ser Leu Glu Cys Leu Ala Leu Lys Glu His Leu
625                 630                 635                 640

Ile Val Tyr Arg Leu Phe Gly Leu Gly Ala Ile Asp Glu Trp Glu Glu
                645                 650                 655

Ile Ile Val Ile His His Ala Ser Pro Asp Ser Val Ile Trp Gln Leu
            660                 665                 670

Pro Lys Asp Lys Ala Tyr Arg Leu Leu Cys Asp Thr Asp Gly Phe Cys
            675                 680                 685

Ala Asp Pro Gly Glu Ile Lys Lys Ala Val Ala Val Asn Gly Ile Gly
            690                 695                 700

Thr Val Ile Leu Tyr Leu Ala
705                 710
```

<210> SEQ ID NO 22
<211> LENGTH: 843
<212> TYPE: PRT
<213> ORGANISM: Thermotoga maritima

<400> SEQUENCE: 22

```
Met Lys Thr Lys Leu Trp Leu Leu Leu Val Leu Leu Leu Ser Ala Leu
1               5                   10                  15
```

-continued

```
Ile Phe Ser Glu Thr Thr Ile Val Val His Tyr His Arg Tyr Asp Gly
             20                  25                  30
Lys Tyr Asp Gly Trp Asn Leu Trp Ile Trp Pro Val Glu Pro Val Ser
         35                  40                  45
Gln Glu Gly Lys Ala Tyr Gln Phe Thr Gly Glu Asp Asp Phe Gly Lys
     50                  55                  60
Val Ala Val Val Lys Leu Pro Met Asp Leu Thr Lys Val Gly Ile Ile
 65                  70                  75                  80
Val Arg Leu Asn Glu Trp Gln Ala Lys Asp Val Ala Lys Asp Arg Phe
                 85                  90                  95
Ile Glu Ile Lys Asp Gly Lys Ala Glu Val Trp Ile Leu Gln Gly Val
            100                 105                 110
Glu Glu Ile Phe Tyr Glu Lys Pro Asp Thr Ser Pro Arg Ile Phe Phe
        115                 120                 125
Ala Gln Ala Arg Ser Asn Lys Val Ile Glu Ala Phe Leu Thr Asn Pro
    130                 135                 140
Val Asp Thr Lys Lys Glu Leu Phe Lys Val Thr Val Asp Gly Lys
145                 150                 155                 160
Glu Ile Pro Val Ser Arg Val Glu Lys Ala Asp Pro Thr Asp Ile Asp
                165                 170                 175
Val Thr Asn Tyr Val Arg Ile Val Leu Ser Glu Ser Leu Lys Glu Glu
            180                 185                 190
Asp Leu Arg Lys Asp Val Glu Leu Ile Ile Glu Gly Tyr Lys Pro Ala
        195                 200                 205
Arg Val Ile Met Met Glu Ile Leu Asp Asp Tyr Tyr Tyr Asp Gly Glu
    210                 215                 220
Leu Gly Ala Val Tyr Ser Pro Glu Lys Thr Ile Phe Arg Val Trp Ser
225                 230                 235                 240
Pro Val Ser Lys Trp Val Lys Val Leu Leu Phe Lys Asn Gly Glu Asp
                245                 250                 255
Thr Glu Pro Tyr Gln Val Val Asn Met Glu Tyr Lys Gly Asn Gly Val
            260                 265                 270
Trp Glu Ala Val Val Glu Gly Asp Leu Asp Gly Val Phe Tyr Leu Tyr
        275                 280                 285
Gln Leu Glu Asn Tyr Gly Lys Ile Arg Thr Thr Val Asp Pro Tyr Ser
    290                 295                 300
Lys Ala Val Tyr Ala Asn Ser Lys Lys Ser Ala Val Val Asn Leu Ala
305                 310                 315                 320
Arg Thr Asn Pro Glu Gly Trp Glu Asn Asp Arg Gly Pro Lys Ile Glu
                325                 330                 335
Gly Tyr Glu Asp Ala Ile Ile Tyr Glu Ile His Ile Ala Asp Ile Thr
            340                 345                 350
Gly Leu Glu Asn Ser Gly Val Lys Asn Lys Gly Leu Tyr Leu Gly Leu
        355                 360                 365
Thr Glu Glu Asn Thr Lys Gly Pro Gly Val Thr Thr Gly Leu Ser
    370                 375                 380
His Leu Val Glu Leu Gly Val Thr His Val His Ile Leu Pro Phe Phe
385                 390                 395                 400
Asp Phe Tyr Thr Gly Asp Glu Leu Asp Lys Asp Phe Glu Lys Tyr Tyr
                405                 410                 415
Asn Trp Gly Tyr Asp Pro Tyr Leu Phe Met Val Pro Glu Gly Arg Tyr
            420                 425                 430
Ser Thr Asp Pro Lys Asn Pro His Thr Arg Ile Arg Glu Val Lys Glu
```

```
            435                 440                 445
Met Val Lys Ala Leu His Lys His Gly Ile Gly Val Ile Met Asp Met
450                 455                 460

Val Phe Pro His Thr Tyr Gly Ile Gly Glu Leu Ser Ala Phe Asp Gln
465                 470                 475                 480

Thr Val Pro Tyr Tyr Phe Tyr Arg Ile Asp Lys Thr Gly Ala Tyr Leu
                485                 490                 495

Asn Glu Ser Gly Cys Gly Asn Val Ile Ala Ser Glu Arg Pro Met Met
                500                 505                 510

Arg Lys Phe Ile Val Asp Thr Val Thr Tyr Trp Val Lys Glu Tyr His
                515                 520                 525

Ile Asp Gly Phe Arg Phe Asp Gln Met Gly Leu Ile Asp Lys Lys Thr
                530                 535                 540

Met Leu Glu Val Glu Arg Ala Leu His Lys Ile Asp Pro Thr Ile Ile
545                 550                 555                 560

Leu Tyr Gly Glu Pro Trp Gly Gly Trp Gly Ala Pro Ile Arg Phe Gly
                565                 570                 575

Lys Ser Asp Val Ala Gly Thr His Val Ala Ala Phe Asn Asp Glu Phe
                580                 585                 590

Arg Asp Ala Ile Arg Gly Ser Val Phe Asn Pro Ser Val Lys Gly Phe
                595                 600                 605

Val Met Gly Gly Tyr Gly Lys Glu Thr Lys Ile Lys Arg Gly Val Val
                610                 615                 620

Gly Ser Ile Asn Tyr Asp Gly Lys Leu Ile Lys Ser Phe Ala Leu Asp
625                 630                 635                 640

Pro Glu Glu Thr Ile Asn Tyr Ala Ala Cys His Asp Asn His Thr Leu
                645                 650                 655

Trp Asp Lys Asn Tyr Leu Ala Ala Lys Ala Asp Lys Lys Lys Glu Trp
                660                 665                 670

Thr Glu Glu Glu Leu Lys Asn Ala Gln Lys Leu Ala Gly Ala Ile Leu
                675                 680                 685

Leu Thr Ser Gln Gly Val Pro Phe Leu His Gly Gly Gln Asp Phe Cys
690                 695                 700

Arg Thr Lys Asn Phe Asn Asp Asn Ser Tyr Asn Ala Pro Ile Ser Ile
705                 710                 715                 720

Asn Gly Phe Asp Tyr Glu Arg Lys Leu Gln Phe Ile Asp Val Phe Asn
                725                 730                 735

Tyr His Lys Gly Leu Ile Lys Leu Arg Lys Glu His Pro Ala Phe Arg
                740                 745                 750

Leu Lys Asn Ala Glu Glu Ile Lys Lys His Leu Glu Phe Leu Pro Gly
                755                 760                 765

Gly Arg Arg Ile Val Ala Phe Met Leu Lys Asp His Ala Gly Gly Asp
                770                 775                 780

Pro Trp Lys Asp Ile Val Val Ile Tyr Asn Gly Asn Leu Glu Lys Thr
785                 790                 795                 800

Thr Tyr Lys Leu Pro Glu Gly Lys Trp Asn Val Val Asn Ser Gln
                805                 810                 815

Lys Ala Gly Thr Glu Val Ile Glu Thr Val Glu Gly Thr Ile Glu Leu
                820                 825                 830

Asp Pro Leu Ser Ala Tyr Val Leu Tyr Arg Glu
                835                 840

<210> SEQ ID NO 23
```

<211> LENGTH: 709
<212> TYPE: PRT
<213> ORGANISM: Unknown
<220> FEATURE:
<223> OTHER INFORMATION: bacterial

<400> SEQUENCE: 23

```
Met Val Ser Ile Gln Arg Ser Phe Glu Ala Tyr Ala Asp Glu Met Asn
1               5                   10                  15

Ile Ile Thr Val Leu Ile Pro Ala Asp Gln Lys Asp Thr Phe Thr Pro
            20                  25                  30

Pro Phe Gln Leu Glu Thr Asp Thr Ala Glu Ile Pro Leu Thr Val Ser
        35                  40                  45

Gln Glu Trp Gln Ile Glu Gly Lys Cys Lys Tyr Val Cys Val Ala Glu
    50                  55                  60

Gln Pro Val Thr Phe Gly Lys Thr His His Val Lys Ala Ser Gly Gly
65                  70                  75                  80

Gly Lys Thr Asp Leu Gln Ile Gly Ala Val Val Arg Thr Asp Ala Phe
                85                  90                  95

Asp Ala Ala Phe Tyr Tyr Asp Gly Glu Leu Gly Ala Val Tyr Thr Ser
            100                 105                 110

Asp Tyr Thr Glu Phe Lys Val Trp Ala Pro Ala Thr Ser Ala Ala
        115                 120                 125

Val Lys Leu Ser His Pro Glu Lys Ser Gly His Thr Leu Gln Met Thr
    130                 135                 140

Arg Met Glu Asn Gly Val Tyr Ala Val Thr Val Ala Gly Asp Leu His
145                 150                 155                 160

Gly Tyr Glu Tyr Val Tyr Arg Ile Cys Asn Asn Leu Glu Trp Thr Glu
                165                 170                 175

Thr Val Asp Pro Tyr Ala Lys Ala Val Thr Val Asn Gly Glu Lys Gly
            180                 185                 190

Val Val Leu Arg Pro Asp Gln Ala Asn Ser Ala Pro Ser Leu Ala Pro
        195                 200                 205

Phe Ser Asp Pro Val Asp Ala Ile Ile Tyr Glu Met His Ile Arg Asp
    210                 215                 220

Phe Ser Ile His Glu Asn Ser Gly Met Lys Asn Lys Gly Lys Tyr Ser
225                 230                 235                 240

Ala Leu Ala Glu Thr Asp Thr Lys Thr Lys Asn Gly Ser Ser Thr Gly
                245                 250                 255

Leu Ser Tyr Leu Lys Glu Leu Gly Val Thr His Ile Glu Leu Leu Pro
            260                 265                 270

Leu Asn Asp Tyr Ala Gly Val Asp Glu Glu Asn Pro Leu Ala Ala Tyr
        275                 280                 285

Asn Trp Gly Tyr Asn Pro Leu His Phe Ala Pro Glu Gly Ser Tyr
    290                 295                 300

Ala Ser Asn Pro His Asp Pro Gln Thr Arg Asn Thr Glu Val Lys Gln
305                 310                 315                 320

Met Ile His Thr Leu Gln Gln His Gly Leu Arg Val Ile Leu Asp Val
                325                 330                 335

Val Tyr Asn His Val Tyr Gln Arg Glu His Ser Pro Phe Glu Lys Thr
            340                 345                 350

Val Pro Gly Tyr Phe Phe Arg His Asp Gln Phe Gly Met Pro Ser Asn
        355                 360                 365

Gly Thr Gly Val Gly Asn Asp Ile Ala Ser Glu Arg Arg Met Ala Arg
    370                 375                 380
```

-continued

```
Lys Phe Ile Thr Asp Cys Val Met Tyr Trp Leu Lys Glu Tyr Asp Val
385                 390                 395                 400

Asp Gly Phe Arg Phe Asp Leu Leu Gly Ile Leu Asp Ile Glu Thr Val
            405                 410                 415

Leu His Met Lys Glu Lys Ala Ser Glu Val Lys Pro Gly Ile Leu Leu
        420                 425                 430

Phe Gly Glu Gly Trp Asp Leu Ala Thr Pro Leu Pro Glu Gln Lys
    435                 440                 445

Ala Thr Leu Ala Asn Ala Ser Lys Met Pro Gly Val Gly Phe Phe Asn
450                 455                 460

Asp Ser Phe Arg Asp Ala Val Lys Gly Asn Thr Phe His Ile Ala Ala
465                 470                 475                 480

Ala Gly Phe Ala Leu Gly Asn Gly Glu Gln Thr Glu Thr Val Met Arg
                485                 490                 495

Gly Ile Ala Gly Ser Ser Gly Trp Lys Glu Thr Ala Pro Leu Val Ser
            500                 505                 510

Ala Pro Ser Gln Ser Ile Asn Tyr Val Glu Ser His Asp Asn His Thr
        515                 520                 525

Phe Trp Asp Lys Met Ser Leu Ala Leu Pro Gln Glu Ser Glu Ser Arg
    530                 535                 540

Lys Arg Ser Arg Gln Lys Leu Ala Ser Ala Ile Ile Leu Leu Ala Gln
545                 550                 555                 560

Gly Val Pro Phe Ile His Ser Gly Gln Glu Phe Phe Arg Thr Lys Gln
                565                 570                 575

Gly Val Glu Asn Ser Tyr Gln Ser Ser Asp Ser Ile Asn Gln Leu Asp
            580                 585                 590

Trp Ser Arg Arg Glu Thr Phe Lys Gln Asp Val Asp Tyr Val Arg Arg
        595                 600                 605

Leu Ile Ser Leu Arg Lys Ala His Pro Ala Phe Arg Leu Thr Ser Ser
    610                 615                 620

Ala Asp Ile Gln Arg Cys Leu Glu Cys Leu Ala Leu Lys Glu His Leu
625                 630                 635                 640

Ile Val Tyr Arg Leu Phe Asn Leu Gly Ala Ile Asp Glu Trp Glu Glu
                645                 650                 655

Ile Ile Val Ile His His Ala Ser Pro Asp Ser Val Thr Trp Gln Leu
            660                 665                 670

Pro Lys Asp Lys Ala Tyr Arg Leu Leu Cys Asp Thr Asp Gly Phe Arg
        675                 680                 685

Ala Asp Pro Gly Glu Ile Lys Lys Ala Val Ala Val Asn Gly Ile Gly
    690                 695                 700

Thr Val Ile Leu Phe
705

<210> SEQ ID NO 24
<211> LENGTH: 718
<212> TYPE: PRT
<213> ORGANISM: Thermus sp.

<400> SEQUENCE: 24

Met Leu His Ile Ser Arg Thr Phe Ala Ala Tyr Leu Asp Glu Met Asp
1               5                   10                  15

Gln Ile Val Val Leu Ala Pro Lys Ser Leu Gly Phe Asp Gly Met Ala
            20                  25                  30

Pro Phe Thr Leu Val Ala Pro Ser Gly Glu Glu Ile Pro Leu Ser Val
```

```
                35                  40                  45
Gln His Val Glu Asp Val Gly Glu Thr Val Lys Tyr Val Cys Arg Phe
 50                  55                  60

Ala Ser Ala Phe Glu Phe Gly Ala Thr Tyr Trp Val Arg Ser Cys Arg
 65                  70                  75                  80

Gly Glu Glu Thr Asp Val Gln Ile Gly Ala Val Val Arg Thr Pro Ala
                 85                  90                  95

Phe Asp Asp Arg Phe Phe Tyr Asp Gly Pro Leu Gly Ala Glu Tyr Leu
                100                 105                 110

Lys Glu Gln Thr Val Phe Arg Val Trp Ala Pro Thr Ala Thr Ala Val
            115                 120                 125

Ser Val Lys Leu Val His Pro His Leu Asp Glu Ile Arg Cys Val Pro
130                 135                 140

Leu Val Arg Gly Glu Arg Gly Val Trp Ser Ala Val Pro Gly Asp
145                 150                 155                 160

Trp Glu Arg Ala Arg Tyr Thr Tyr Ile Ala Cys Ile Asn Arg Val Trp
                165                 170                 175

Arg Glu Ala Val Asp Pro Tyr Ala Thr Ala Val Ser Val Asn Gly Glu
            180                 185                 190

Phe Gly Val Val Ile Asp Trp Glu Lys Thr Lys Leu Ala Pro Pro Ser
            195                 200                 205

Leu Pro Leu Pro Pro Leu Cys Ser Pro Thr Asp Ala Ile Ile Tyr Glu
210                 215                 220

Leu Ser Ile Arg Asp Phe Thr Ser His Pro Asp Ser Gly Ala Val His
225                 230                 235                 240

Lys Gly Lys Tyr Leu Gly Leu Ala Glu Thr Asn Thr Ser Gly Pro Asn
                245                 250                 255

Gly Thr Ala Thr Gly Leu Ser Tyr Val Lys Glu Leu Gly Val Thr His
            260                 265                 270

Val Gln Leu Met Pro Phe Met Asp Phe Ala Gly Val Asp Glu Arg Asp
            275                 280                 285

Pro Gln Ala Ala Tyr Asn Trp Gly Tyr Asn Pro Leu His Leu Tyr Ala
290                 295                 300

Pro Glu Gly Ser Tyr Ala Thr Asp Pro Ala Asp Pro Tyr Ala Arg Ile
305                 310                 315                 320

Val Glu Leu Lys Gln Ala Ile His Thr Leu His Glu Asn Gly Leu Arg
                325                 330                 335

Val Val Met Asp Ala Val Tyr Asn His Val Tyr Asp Arg Glu Gln Ser
            340                 345                 350

Pro Leu Glu Lys Leu Val Pro Gly Tyr Tyr Phe Arg Tyr Asp Ala Tyr
            355                 360                 365

Gly Gln Pro Ala Asn Gly Thr Gly Val Gly Asn Asp Ile Ala Ser Glu
            370                 375                 380

Arg Arg Met Ala Arg Arg Trp Ile Val Asp Ser Val Val Phe Trp Ala
385                 390                 395                 400

Lys Glu Tyr Gly Ile Asp Gly Phe Arg Phe Asp Leu Met Gly Val His
                405                 410                 415

Asp Ile Glu Thr Met Lys Ala Val Arg Asp Ala Leu Asp Ala Ile Asp
            420                 425                 430

Pro Ser Ile Leu Val Tyr Gly Glu Gly Trp Asp Leu Pro Thr Pro Leu
            435                 440                 445

Pro Pro Glu Gln Lys Ala Thr Met Ala Asn Ala Lys Gln Leu Pro Arg
450                 455                 460
```

Phe Ala Tyr Phe Asn Asp Arg Phe Arg Asp Ala Val Lys Gly Ser Thr
465                 470                 475                 480

Phe His Leu Pro Asp Arg Gly Phe Ala Leu Gly Asn Pro Gly Gly Arg
            485                 490                 495

Glu Gln Val Lys Leu Ala Ile Ala Gly Ser Leu Arg Ala Leu Gly Gly
        500                 505                 510

Leu Phe Cys His Pro Arg Gln Ser Ile Asn Tyr Val Glu Cys His Asp
    515                 520                 525

Asn His Thr Phe Trp Asp Lys Met Glu Ala Ala Asn His Asp Glu Pro
530                 535                 540

Glu Trp Leu Arg Arg Lys Arg Gln Lys Leu Ala Thr Ala Ile Val Leu
545                 550                 555                 560

Leu Ala Gln Gly Ile Pro Phe Leu His Ser Gly Gln Glu Phe Tyr Arg
                565                 570                 575

Thr Lys Gly Gly Asp Gly Asn Ser Tyr Arg Ser Pro Asp Ala Val Asn
            580                 585                 590

Gln Leu Asp Trp Glu Arg Lys Ser Arg Tyr Glu Asp Val Arg Tyr
    595                 600                 605

Val Gln Gly Leu Ile Ala Leu Arg Arg Ala His Gly Ala Phe Arg Leu
610                 615                 620

Ala Thr Glu Ala Glu Val Leu Arg His Phe Thr Phe Leu Glu Pro Leu
625                 630                 635                 640

Pro Pro Ser Val Ile Ala Tyr Arg Leu His Asp Ala Ala Val Tyr Gly
                645                 650                 655

Pro Trp Glu Asp Ile Ile Val Val His His Asn Glu Glu Lys Glu Thr
            660                 665                 670

Ala Ile Ala Leu Pro Asp Glu Arg Glu Trp Ala Val Val Cys Asp Gly
        675                 680                 685

Gln Arg Cys Gly Thr Thr Pro Phe Gly Gln Ala Arg Gly Met Leu Arg
    690                 695                 700

Leu Asp Gly Ile Gly Thr Trp Val Leu Val His Pro Ala Gly
705                 710                 715

<210> SEQ ID NO 25
<211> LENGTH: 846
<212> TYPE: PRT
<213> ORGANISM: Bacillus cereus

<400> SEQUENCE: 25

Met Ile Lys Arg Leu Ile Asn Lys Ser Val Leu Leu Thr Ile Ile
1               5                   10                  15

Val Met Leu Ser Ser Val Phe Ser Phe Gln Ser Val Lys Ala Val Ser
            20                  25                  30

Asn Ser Lys Thr Thr Glu Val Ile Ile His Tyr Lys Glu Gln Ser Gly
        35                  40                  45

Asn Thr Lys Asp Trp Asn Leu Trp Ile Trp Gly Glu Asn Ala Asn Gly
    50                  55                  60

Asn Ser Tyr Glu Phe Thr Gly Glu Asp Glu Phe Gly Lys Tyr Ala Lys
65                  70                  75                  80

Ile Asn Ile Asp Gly Asp Tyr Asn Arg Val Gly Phe Ile Ile Arg Thr
                85                  90                  95

Asn Glu Trp Glu Lys Asp Gly Ser Asp Arg Trp Ile Glu Asn Ile Lys
            100                 105                 110

Asp Gly Arg Ala Glu Val Trp Ile Leu Ser Gly Asp Glu Lys Val Tyr

```
                115                 120                 125
Asn Ser Lys Pro Ser Ser Asp Leu Ser Ile Gln Lys Ala Thr Ile Asp
            130                 135                 140
Ser Phe His Glu Ile Thr Val Thr Thr Asn Val Pro Phe Asn Ile Arg
145                 150                 155                 160
Glu Lys Lys Ile Glu Met Glu Gly Ile Lys Ile Lys Ser Ile Ser Pro
                165                 170                 175
Tyr Asp Lys Asn Ser Gly Asp Ile Thr Asn Lys Phe Lys Ile Ile Thr
            180                 185                 190
Glu Gln Lys Ile Asp Leu Lys Gln Thr Tyr Lys Val Lys Ile Glu Asn
        195                 200                 205
Val Ala Asp Thr Asn Thr Glu Ile Gly Lys Val Ile Arg Ser Glu Glu
    210                 215                 220
Phe Asp His Ser Phe Tyr Tyr Gly Gly Asn Asp Leu Gly Asn Ile Tyr
225                 230                 235                 240
Thr Pro Gln His Thr Lys Phe Arg Val Trp Ala Pro Thr Ser Ser Glu
                245                 250                 255
Ala Lys Leu Val Thr Tyr Lys Lys Trp Asn Asp Lys Ile Gly Thr Glu
            260                 265                 270
Ile Asn Met Gln Gln Ser Glu Lys Gly Thr Trp Lys Ala Glu Leu Lys
        275                 280                 285
Gly Asn Gln Lys Gly Leu Tyr Tyr Thr Tyr Lys Val Lys Ile Gly Asp
    290                 295                 300
Lys Trp Ile Glu Ala Val Asp Pro Tyr Ala Arg Ala Ala Ser Val Asn
305                 310                 315                 320
Gly Asp Lys Gly Ala Val Val Asp Leu Glu Glu Thr Asn Pro Lys Lys
                325                 330                 335
Trp Lys Ala Asn Lys Lys Pro Lys Phe Lys Asn Pro Glu Asp Ala Ile
            340                 345                 350
Ile Tyr Glu Leu His Val Arg Asp Leu Ser Ile Gln Pro Glu Ser Gly
        355                 360                 365
Ile Lys Gln Lys Gly Lys Tyr Leu Gly Val Thr Glu Lys Gly Thr Lys
    370                 375                 380
Gly Pro Glu Gly Val Lys Thr Gly Leu Asp His Ile Lys Asp Leu Gly
385                 390                 395                 400
Val Thr His Val Gln Phe Leu Pro Ile Phe Asp Tyr Ala Ser Val Asn
                405                 410                 415
Glu Glu Asn Val Asn Glu Pro Gln Tyr Asn Trp Gly Tyr Asp Pro Lys
            420                 425                 430
Asn Phe Asn Val Pro Glu Gly Ser Tyr Ser Thr Asn Pro Tyr Glu Pro
        435                 440                 445
Thr Val Arg Ile Thr Glu Leu Lys Gln Met Ile Gln Thr Leu His Asp
    450                 455                 460
Asn Asn Leu Arg Val Val Met Asp Val Val Tyr Asn His Met Tyr Ser
465                 470                 475                 480
Ala Thr Glu Ser Asn Phe His Lys Leu Val Pro Gly Tyr Tyr Arg
                485                 490                 495
Tyr Asn Glu Asp Gly Thr Phe Ala Asn Gly Thr Gly Val Gly Asn Asp
            500                 505                 510
Thr Ala Ser Glu Arg Lys Met Met Arg Lys Phe Met Ile Asp Ser Val
        515                 520                 525
Thr Tyr Trp Ala Lys Glu Tyr Asn Leu Asp Gly Phe Arg Phe Asp Leu
    530                 535                 540
```

Met Gly Ile His Asp Tyr Glu Thr Met Asn Glu Ile Arg Lys Ala Val
545                 550                 555                 560

Asn Gln Ile Asp Pro Ser Ile Ile Leu His Gly Glu Gly Trp Asp Leu
            565                 570                 575

Asn Thr Pro Leu Ala Ala Glu Leu Lys Ala Asn Gln Lys Asn Ala Glu
            580                 585                 590

Lys Met Lys Gly Ile Ala His Phe Asn Asp Asn Ile Arg Asp Gly Leu
            595                 600                 605

Lys Gly Ser Val Phe Glu Glu Lys Glu Asn Gly Phe Ile Asn Gly Lys
        610                 615                 620

Glu Asn Met Glu Asp Arg Ile Lys Lys Gly Ile Thr Ala Gly Ile Asp
625                 630                 635                 640

Tyr Asp Thr Asn Ser Ser Thr Tyr Gln Asp Pro Glu Gln Val Leu Thr
                645                 650                 655

Tyr Val Glu Ala His Asp Asn His Thr Leu Trp Asp Lys Leu Glu Leu
            660                 665                 670

Thr Asn Pro Ser Asp Ser Glu Glu Val Arg Lys Gln Met His Lys Leu
            675                 680                 685

Ser Ser Ser Ile Leu Leu Thr Ser Gln Gly Ile Pro Phe Leu His Ala
        690                 695                 700

Gly Gln Glu Phe Met Arg Thr Lys Tyr Gly Asp His Asn Ser Tyr Lys
705                 710                 715                 720

Ser Pro Asp Ser Ile Asn Gln Met Asp Trp Leu Arg Arg Ala Thr Phe
                725                 730                 735

Asn Asn Glu Val Asp Tyr Met Lys Gly Leu Ile Glu Leu Arg Lys Lys
            740                 745                 750

Tyr Ser Ala Phe Arg Met Thr Ser Ala Glu Gln Ile Lys Thr His Val
        755                 760                 765

Ser Phe Ile Asp Ala Pro Lys Asn Thr Val Ala Tyr Thr Ile Glu Gly
770                 775                 780

Asn Lys Asn Glu Tyr Phe Thr Val Ala His Asn Ala Asn Arg Glu Ala
785                 790                 795                 800

Val Glu Ile Thr Leu Pro Ser Lys Gly Pro Trp Lys Val Leu Val Asp
                805                 810                 815

Gly Lys Gln Ala Gly Ser Lys Pro Leu Tyr Val Val His Asp Asn Lys
            820                 825                 830

Ile Lys Val Pro Ala Leu Ser Ser Phe Val Leu Lys Leu Lys
        835                 840                 845

<210> SEQ ID NO 26
<211> LENGTH: 718
<212> TYPE: PRT
<213> ORGANISM: Unknown
<220> FEATURE:
<223> OTHER INFORMATION: bacterial

<400> SEQUENCE: 26

Met Val Cys Ile Gln Arg Ser Phe Glu Ala Tyr Ala Asp Glu Met Asn
1               5                   10                  15

Ile Ile Thr Val Leu Ile Pro Ala Asp Gln Lys Asp Thr Phe Thr Pro
            20                  25                  30

Pro Phe Gln Leu Glu Thr Asp Thr Ala Glu Ile Pro Leu Thr Val Ser
        35                  40                  45

Gln Glu Trp Gln Ile Glu Gly Lys Tyr Lys Tyr Val Cys Val Ala Glu
50                  55                  60

```
Gln Pro Val Ala Phe Gly Lys Thr His His Val Lys Ala Ser Gly Gly
 65                  70                  75                  80

Gly Lys Thr Asp Leu Gln Ile Gly Ala Val Arg Thr Asp Ala Phe
             85                  90                  95

Asp Ala Ala Phe Tyr Tyr Asp Gly Glu Leu Gly Ala Val Tyr Ala Ser
                100                 105                 110

Asp Tyr Thr Glu Phe Lys Val Trp Ala Pro Ala Ala Thr Ser Ala Ala
                115                 120                 125

Val Lys Leu Ser His Pro Glu Lys Ser Gly Tyr Thr Leu Gln Met Thr
130                 135                 140

Arg Met Glu Asn Gly Val Tyr Ala Val Thr Val Ala Gly Asp Leu His
145                 150                 155                 160

Gly Tyr Glu Tyr Val Tyr Arg Ile Cys Asn Asn Leu Glu Trp Thr Glu
                165                 170                 175

Thr Val Asp Pro Tyr Ala Lys Ala Val Thr Val Asn Gly Glu Lys Gly
                180                 185                 190

Val Val Leu Arg Pro Asp Gln Ala Asn Ser Ala Pro Ser Phe Thr Pro
                195                 200                 205

Phe Ser Ala Pro Val Asp Ala Ile Ile Tyr Glu Met His Ile Arg Asp
210                 215                 220

Phe Ser Ile His Glu Asn Ser Gly Thr Lys Asn Lys Gly Lys Tyr Ala
225                 230                 235                 240

Ala Leu Ala Glu Thr Asp Thr Lys Thr Lys Asn Gly Ser Ser Thr Gly
                245                 250                 255

Leu Ser Tyr Leu Lys Glu Leu Gly Val Thr His Ile Glu Leu Leu Pro
                260                 265                 270

Leu Asn Asp Tyr Ala Gly Val Asp Glu Glu Asn Pro Leu Ala Ala Tyr
                275                 280                 285

Asn Trp Gly Tyr Asn Pro Leu His Phe Phe Ala Pro Glu Gly Ser Tyr
                290                 295                 300

Ser Ser Asn Pro His Asp Pro Gln Thr Arg Asn Thr Glu Val Lys Gln
305                 310                 315                 320

Met Ile His Thr Leu His Gln His Gly Leu Arg Val Ile Leu Asp Val
                325                 330                 335

Val Tyr Asn His Val Tyr Gln Arg Glu His Ser Pro Phe Glu Lys Thr
                340                 345                 350

Val Pro Gly Tyr Phe Phe Arg His Asp Gln Phe Gly Met Pro Ser Asn
                355                 360                 365

Gly Thr Gly Val Gly Asn Asp Ile Ala Ser Glu Arg Arg Met Ala Arg
                370                 375                 380

Lys Phe Ile Thr Asp Cys Val Met Tyr Trp Leu Lys Glu Tyr Asp Val
385                 390                 395                 400

Asp Gly Phe Arg Phe Asp Leu Leu Gly Ile Leu Asp Ile Glu Thr Val
                405                 410                 415

Leu His Met Lys Glu Lys Ala Ser Glu Val Lys Ser Gly Ile Leu Leu
                420                 425                 430

Phe Gly Glu Gly Trp Asp Leu Ala Thr Pro Leu Pro Pro Glu Gln Lys
                435                 440                 445

Ala Thr Leu Ala Asn Ala Ser Lys Met Pro Gly Val Gly Phe Phe Asn
                450                 455                 460

Asp Ser Phe Arg Asp Ala Val Lys Gly Asn Thr Phe His Ile Ala Ala
465                 470                 475                 480
```

```
Ala Gly Phe Ala Leu Gly Asn Gly Glu Lys Thr Glu Thr Val Met His
                485                 490                 495

Gly Ile Ala Gly Ser Ser Gly Trp Lys Glu Thr Ala Pro Leu Val Ser
            500                 505                 510

Ala Pro Ser Gln Ser Ile Asn Tyr Val Glu Ser His Asp Asn His Thr
        515                 520                 525

Phe Trp Asp Lys Met Ser Leu Ala Leu Pro Gln Glu Ser Glu Ser Arg
    530                 535                 540

Lys Arg Ser Arg Gln Lys Leu Ala Ser Ala Ile Ile Leu Leu Ala Gln
545                 550                 555                 560

Gly Val Pro Phe Ile His Ser Gly Gln Glu Phe Phe Arg Thr Lys Gln
                565                 570                 575

Gly Val Glu Asn Ser Tyr Gln Ser Ser Asp Ser Ile Asn Gln Leu Asp
            580                 585                 590

Trp Ser Arg Arg Glu Thr Phe Lys Gln Asp Val Asp Tyr Val Arg Arg
        595                 600                 605

Leu Ile Ser Leu Arg Lys Ala His Pro Ala Phe Arg Leu Thr Ser Ser
    610                 615                 620

Ala Asp Ile Gln Arg Cys Leu Glu Cys Leu Ala Leu Lys Glu His Leu
625                 630                 635                 640

Ile Val Tyr Arg Leu Phe Asn Leu Gly Ala Ile Asp Glu Trp Glu Glu
                645                 650                 655

Ile Ile Val Ile His His Ala Ser Pro Asp Ser Val Thr Trp Gln Leu
            660                 665                 670

Pro Lys Asp Lys Ala Tyr Arg Leu Leu Cys Asp Thr Asp Gly Phe Arg
        675                 680                 685

Ala Asp His Gly Glu Ile Lys Lys Ala Val Ala Val Asn Gly Ile Gly
    690                 695                 700

Thr Val Ile Leu Tyr Leu Ala Arg Asp Leu Thr Ser Phe Ala
705                 710                 715

<210> SEQ ID NO 27
<211> LENGTH: 1443
<212> TYPE: PRT
<213> ORGANISM: Unknown
<220> FEATURE:
<223> OTHER INFORMATION: bacterial

<400> SEQUENCE: 27

Met Phe Thr Lys Lys Arg Val Val Arg Ala Ala Leu Leu Val Val Gly
1               5                   10                  15

Ala Tyr Thr Leu Ala Gly Cys Gly Gly Ser Gly Val Glu Ser Gly Thr
            20                  25                  30

Asn Asp Leu Leu Thr Cys Glu Val Pro Asn Val Pro Asn Ser Thr Gly
        35                  40                  45

Thr Ala Cys Glu Pro Pro Pro Ile Gln Cys Asp Ala Pro Leu Val
    50                  55                  60

Pro Asn Glu Ala Asn Asp Ala Cys Glu Ala Gly Ala Asp Pro Ser Leu
65                  70                  75                  80

Pro Ala Pro Val Phe Thr Pro Ser Ser Asn Gln Ala Val Leu Tyr Tyr
                85                  90                  95

Asn Arg Ala Ala Val Asp Ala Asp Asn Ser Asn Asn Asp Pro Ala Tyr
            100                 105                 110

Glu Gly Trp Arg Leu His Thr Trp Asn Asn Asp Glu Cys Asp Ala Tyr
        115                 120                 125
```

```
Ala Asp Ala Asp Thr Asp Trp Ala Asn Gly Arg Ile His Ser Gly Ile
130                 135                 140

Asp Pro Asn Tyr Gly Ala Tyr Trp Ile Leu Asp Leu Lys Glu Gly Tyr
145                 150                 155                 160

Gly Ser Cys His Asn Phe Ile Ile His Lys Gly Thr Asp Asp Ala Gly
            165                 170                 175

Lys Glu Met Gly Gly Asp Phe Gln Ala Ser Leu Val Gln Glu Asp
        180                 185                 190

Asp Thr Phe Val Arg Met Asn Phe Thr Leu Ser Gly Glu Pro Thr Ile
        195                 200                 205

Phe Glu Phe Pro Ile Met Ser Leu Gly Pro Gln Pro Val Asp Ile Glu
210                 215                 220

Gly Phe Ser Ala His Trp Leu Asp Ala Asn Thr Ile Leu Trp Asp Val
225                 230                 235                 240

Pro Glu Thr Val Ala Glu Val Lys Leu His Tyr Ser Ala Lys Ala Asp
                245                 250                 255

Phe Glu Ser Thr Leu Glu Glu Gly Ile Asn Gly Thr Glu Val Ala Leu
            260                 265                 270

Met Ser Thr Thr Leu Thr Glu Glu Gln Ser Ala Arg Val Pro His Leu
        275                 280                 285

Ser Ser Met Gln Ala Trp Glu Gly Asp Trp Ser Val Glu Asp Ala Lys
290                 295                 300

Ile Val Leu Thr Thr Gln Ala Val Val Gly Gly Tyr Asp Ala Asp Gly
305                 310                 315                 320

Thr Leu Ile Ala Ala Thr Gly Ile Gln Leu Ala Asn Ala Ile Asp Ala
                325                 330                 335

Leu Tyr Thr Met Gly Glu Asp Asp Ala Asp Glu Ala Gln Phe Gly Gly
            340                 345                 350

Ile Tyr Thr Asp Ser Gly Ile Thr Ala Ser Leu Trp Ala Pro Thr Ala
        355                 360                 365

Ser Asn Val Asp Leu Leu Leu Tyr Asn Asp Asn Lys Thr Leu Ser Gln
370                 375                 380

Arg Leu Asp Met Val Arg Asp Asp Thr Ser Gly Val Trp Arg Tyr Glu
385                 390                 395                 400

Gly Asp Met Ser Leu Asp Arg Gln Leu Tyr Arg Tyr Glu Val Thr Val
                405                 410                 415

Tyr His Pro Asn Thr Gly Asn Ile Glu Thr Leu Leu Val Thr Asp Pro
            420                 425                 430

Tyr Ser Val Ser Leu Ser Thr Asn Gly Arg Phe Ser Arg Phe Val Asn
        435                 440                 445

Leu Ala Asp Glu Asp Leu Lys Pro Glu Gly Trp Asp Thr His Ala Ile
450                 455                 460

Pro Thr Val Asp Asn Tyr Glu Asp Ala Val Ile Tyr Glu Gly His Val
465                 470                 475                 480

Arg Asp Phe Ser Val Arg Asp Met Ser Thr Ser Glu Glu Asn Arg Gly
                485                 490                 495

Lys Tyr Leu Ala Phe Thr Glu Asp Gly Thr Ala Pro Val Glu His Leu
            500                 505                 510

Lys Lys Leu Val Asp Ala Gly Leu Thr Tyr Phe His Ile Leu Pro Ala
        515                 520                 525

Asn Asp Ile Ala Thr Ile Asp Glu Asp Pro Thr Lys Thr Val Asp Leu
530                 535                 540

Tyr Asp Thr Val Gly Lys Leu Cys Arg Leu Asn Ser Ser Ala Ala Val
```

```
545                 550                 555                 560
Cys Glu Glu Glu Ser Ala Asp Ala Leu Leu Ile Asp Val Tyr Asn Gly
                565                 570                 575
Tyr Asp Pro Leu Ser Gln Ala Gly Lys Ala Gln Gln Leu Thr Asn Asp
            580                 585                 590
Leu Arg Asn Leu Asp Thr Phe Asn Trp Gly Tyr Asp Pro His His Phe
        595                 600                 605
Asn Ala Pro Glu Gly Ser Tyr Ala Ser Ser Ala Glu Gly Val Glu Arg
    610                 615                 620
Ile Val Glu Met Arg Ala Met Ile Gln Ala Leu His Glu Met Gly Leu
625                 630                 635                 640
Arg Val Ala Leu Asp Val Val Tyr Asn His Thr Asn Ala Ser Gly Val
                645                 650                 655
Phe Ser Lys Ser Val Leu Asp Lys Ala Val Pro Gly Tyr Tyr His Arg
            660                 665                 670
Tyr Glu Val Asp Thr Gly Ala Ile Val Arg Glu Thr Cys Cys Asp Asp
        675                 680                 685
Thr Glu Pro Arg Asn Val Met Met Glu Lys Phe Met Glu Asp Ser Leu
    690                 695                 700
Leu Met Trp Thr Glu His Tyr Lys Tyr Asp Ser Phe Arg Phe Asp Ile
705                 710                 715                 720
Met Ser Gln Ala Thr Lys Asp Thr Met Val Arg Leu Arg Asp Ala Val
                725                 730                 735
Gln Ala Ile Asp Ala Asp Asn Tyr Phe Tyr Gly Glu Gly Trp Thr Lys
            740                 745                 750
Ile Asp Arg Gly Tyr Glu Gln Ala Ser Gln Leu Asn Met Ala Gly Thr
        755                 760                 765
Glu Ile Gly Thr Tyr Asn Asp Arg Ile Arg Glu Ala Ile Arg Gln Gly
    770                 775                 780
Ala Ile Phe Arg Pro Glu Asp Glu Gly Leu Leu Ser Ala Gln Asp Arg
785                 790                 795                 800
Val Lys Met Gly Met Ile Gly Thr Leu Lys Asp Tyr Val Leu Glu Thr
                805                 810                 815
Ser Ser Gly Ser Ala Gly Ala Thr Ser Asn Leu Gly Gly Tyr Ala Glu
            820                 825                 830
Asp Pro Ala Asp Ile Ile Asn Tyr Val Ser Lys His Asp Asn Glu Thr
        835                 840                 845
Leu Trp Asp Gln Leu Asn Tyr Thr Leu Pro Gln Asp Ile Thr Leu Glu
    850                 855                 860
Gln Arg Val Arg Ala Gln Asn Val Ala Met Gly Ile Asn Leu Val Ser
865                 870                 875                 880
Gln Gly Ile Pro Phe Leu Gln Met Gly Gly Asp Met Leu Arg Ser Lys
                885                 890                 895
Ser Met Asp Arg Asn Thr Tyr Asp Ala Gly Asp Trp Phe Asn Tyr Val
            900                 905                 910
Asp Phe Thr Tyr Glu Thr Asn Asn Trp Asn Val Gly Leu Pro Leu Ala
        915                 920                 925
Gln Asp Asn Glu Ala Arg Trp Glu Glu Met Gly Glu Phe Ile Tyr Asn
    930                 935                 940
Pro Asn Arg Ala Ala Ser Met Ala Asp Ile Met Phe Ala Ser Asp Val
945                 950                 955                 960
Phe Ala Glu Leu Leu Asn Ile Arg Met Thr Ser Pro Leu Phe Arg Leu
                965                 970                 975
```

```
Thr Thr Ala Glu Gly Ile Ile Asp Arg Ile Gly Phe His Asn Ile Gly
            980                 985                 990

Glu Arg Gln Gln Arg Gly Leu Ile Ala Met Ser Ile Asp Asp Gly Ile
        995                 1000                1005

Ser Glu Asn Ser Glu Val Pro Arg Gln Asp Leu Asp Met Met Asn
    1010                1015                1020

Asp Ala Val Met Val Leu Val Asn Thr Gly Tyr Glu Glu Lys Ser
    1025                1030                1035

Ile Thr Val Asn Thr Ala Thr Gly Phe Ser Leu His Ala Thr Gln
    1040                1045                1050

Met Asn Ser Val Asp Ala Ala Val Arg Gly Ala Thr Phe Val Glu
    1055                1060                1065

Gly Glu Asp Gly Asn Gly Thr Phe Thr Val Pro Ala Leu Thr Ile
    1070                1075                1080

Ala Val Phe Val Lys Pro Gln Ser Gly Ala Gln Gly Tyr Gly Leu
    1085                1090                1095

Ser Ala Tyr Ala Thr Ser Gly Ala Pro Asp Val Val Pro Tyr Gly
    1100                1105                1110

Asp Thr Ile Ala Tyr Leu Arg Gly Asp Met Asn Gly Trp Ser Thr
    1115                1120                1125

Asp Asp Ala Phe Ala Tyr Gln Gly Asp Gly Lys Tyr Thr Val Thr
    1130                1135                1140

Ala Thr Leu Glu Gly Gly Val Thr Tyr Gly Phe Lys Phe Ala Ser
    1145                1150                1155

Glu Asp Trp Ser Thr Val Asn Phe Gly Ala Ala Asp Gly Glu Glu
    1160                1165                1170

Gly Thr Val Ile Ala Gly Glu Glu Lys Val Leu Ala Arg Thr Asn
    1175                1180                1185

Thr Asn Leu Ser Phe Thr Pro Ala Thr Ser Ala Thr Tyr Leu Phe
    1190                1195                1200

Thr Ile Asp Ala Thr Asp Ser Glu Ala Pro Ile Leu Met Val Glu
    1205                1210                1215

Asn Glu Glu Pro Tyr Val Gly Thr Pro Val Tyr Leu Arg Gly Ala
    1220                1225                1230

Met Asn Asp Trp Gly Thr Ala Glu Glu Phe Ala Tyr Gln Gly Gly
    1235                1240                1245

Arg Val Tyr Thr Phe Ser Arg Asp Val Glu Pro Gly Thr Tyr Glu
    1250                1255                1260

Phe Lys Val Ser Ser Glu Asp Trp Asn Thr Val Asn Phe Gly Ala
    1265                1270                1275

Ile Ser Ala Asp Asp Ser Asp Arg Asn Leu Ala Pro Gly Gln Thr
    1280                1285                1290

Leu Gly Leu Ala Ala Thr Asn Asp Asn Leu Ile Leu Asn Ile Glu
    1295                1300                1305

Thr Ala Asp Arg Tyr Val Phe Val Asn Val Thr Asp Leu Asp
    1310                1315                1320

Ala Pro Thr Ile Gly Val Phe Lys Glu Ala Phe Trp Gly Asp Thr
    1325                1330                1335

Gln Val Tyr Ile Arg Gly Gly Met Asn Gly Trp Gly Ala Val Asp
    1340                1345                1350

Met Phe Glu Tyr Gln Gly Glu Gly Val Tyr Thr Ala Asp Ile Glu
    1355                1360                1365
```

```
Leu Ser Ala Gly Ser Ile Glu Phe Lys Val Ala Ser Glu Asp Trp
    1370            1375                1380

Ser Thr Val Asn Leu Gly Ser Pro Asn Asp Ala Ala Ser Asn Val
    1385            1390                1395

Val Thr Pro Ser Glu Pro Lys Ile Leu Gly Ala Ser Asn Asn Asn
    1400            1405                1410

Leu Met Ile Glu Val Ala Glu Ser Gly Leu Tyr Glu Phe Lys Val
    1415            1420                1425

Ser Gly Pro Asp Gly Asn Ala Pro Thr Leu Thr Ile Thr Met Lys
    1430            1435                1440

<210> SEQ ID NO 28
<211> LENGTH: 1096
<212> TYPE: PRT
<213> ORGANISM: Klebsiella pneumoniae

<400> SEQUENCE: 28

Met Val Arg Tyr Thr Cys His Ala Leu Phe Ile Gly Ser Leu Val Leu
1               5                   10                  15

Leu Ser Gly Cys Asp Asn Ser Ser Ser Ser Ser Ser Gly Ser Pro
            20                  25                  30

Gly Asp Pro Gly Asn Pro Gly Thr Pro Asp Pro Gln Asp Val Val
        35                  40                  45

Arg Leu Pro Asp Val Ala Val Pro Gly Glu Ala Val Gln Ala Ser Ala
50                  55                  60

Asn Gln Ala Val Ile His Leu Val Asp Ile Ala Gly Ile Thr Ser Ser
65                  70                  75                  80

Thr Pro Ala Asp Tyr Ala Ser Lys Asn Leu Tyr Leu Trp Asn Asn Glu
                85                  90                  95

Thr Cys Asp Ala Leu Ser Ala Pro Val Ala Asp Trp Asn Asp Val Ser
            100                 105                 110

Thr Thr Pro Thr Gly Ser Asp Lys Tyr Gly Pro Tyr Trp Ala Ile Pro
        115                 120                 125

Leu Thr Lys Glu Ser Gly Cys Ile Asn Val Ile Val Arg Asp Gly Thr
    130                 135                 140

Asn Lys Leu Ile Asp Ser Asp Leu Arg Val Ser Phe Ser Asp Phe Thr
145                 150                 155                 160

Asp Arg Thr Val Ser Val Ile Ala Gly Asn Ser Ala Val Tyr Asp Ser
                165                 170                 175

Arg Ala Asp Ala Phe Arg Ala Phe Gly Val Ala Leu Ala Asp Ala
            180                 185                 190

His Trp Val Asp Lys Thr Thr Leu Leu Trp Pro Gly Glu Asn Lys
        195                 200                 205

Pro Ile Val Arg Leu Tyr Tyr Ser His Ser Ser Lys Val Ala Ala Asp
    210                 215                 220

Ser Asn Gly Glu Phe Thr Asp Lys Tyr Val Lys Pro Thr Pro Thr Thr
225                 230                 235                 240

Val Ser Gln Gln Val Ser Met Arg Phe Pro His Leu Ala Ser Tyr Pro
                245                 250                 255

Ala Phe Lys Leu Pro Asp Asp Val Asn Val Asp Glu Leu Leu Gln Gly
            260                 265                 270

Glu Thr Val Ala Ile Ser Ala Glu Ser Asp Gly Ile Leu Ser Ser Ala
        275                 280                 285

Thr Gln Val Gln Thr Ala Gly Val Leu Asp Asp Thr Tyr Ala Ala Ala
    290                 295                 300
```

```
Ala Glu Ala Leu Ser Tyr Gly Ala Gln Leu Thr Asp Ser Gly Val Thr
305                 310                 315                 320

Phe Arg Val Trp Ala Pro Thr Ala Gln Gln Val Glu Leu Val Ile Tyr
            325                 330                 335

Ser Ala Asp Lys Lys Val Ile Ala Ser His Pro Met Thr Arg Asp Ser
        340                 345                 350

Ala Ser Gly Ala Trp Ser Trp Gln Gly Gly Ser Asp Leu Lys Gly Ala
    355                 360                 365

Phe Tyr Arg Tyr Ala Met Thr Val Tyr His Pro Gln Ser Arg Lys Val
370                 375                 380

Glu Gln Tyr Glu Val Thr Asp Pro Tyr Ala His Ser Leu Ser Thr Asn
385                 390                 395                 400

Ser Glu Tyr Ser Gln Val Val Asp Leu Asn Asp Ser Ala Leu Lys Pro
            405                 410                 415

Glu Gly Trp Asp Gly Leu Thr Met Pro His Ala Gln Lys Thr Lys Ala
        420                 425                 430

Asp Leu Ala Lys Met Thr Ile His Glu Ser His Ile Arg Asp Leu Ser
    435                 440                 445

Ala Trp Asp Gln Thr Val Pro Ala Glu Leu Arg Gly Lys Tyr Leu Ala
450                 455                 460

Leu Thr Ala Gln Glu Ser Asn Met Val Gln His Leu Lys Gln Leu Ser
465                 470                 475                 480

Ala Ser Gly Val Thr His Ile Glu Leu Leu Pro Val Phe Asp Leu Ala
            485                 490                 495

Thr Val Asn Glu Phe Ser Asp Lys Val Thr Asp Ile Gln Gln Pro Phe
        500                 505                 510

Ser Arg Leu Cys Glu Ile Asn Ser Ala Val Glu Ser Ser Glu Phe Ala
    515                 520                 525

Gly Tyr Cys Asp Ser Gly Ser Thr Val Glu Glu Ala Leu Thr Gln Leu
530                 535                 540

Lys Gln Asn Asp Ser Lys Asp Asn Pro Gln Val Gln Ala Leu Asn Thr
545                 550                 555                 560

Leu Val Ala Gln Thr Asp Ser Tyr Asn Trp Gly Tyr Asp Pro Phe His
            565                 570                 575

Tyr Thr Val Pro Glu Gly Ser Tyr Ala Thr Asp Pro Glu Gly Thr Ala
        580                 585                 590

Arg Ile Lys Glu Phe Arg Thr Met Ile Gln Ala Ile Lys Gln Asp Leu
    595                 600                 605

Gly Met Asn Val Ile Met Asp Val Val Tyr Asn His Thr Asn Ala Ala
610                 615                 620

Gly Pro Thr Asp Arg Thr Ser Val Leu Asp Lys Ile Val Pro Trp Tyr
625                 630                 635                 640

Tyr Gln Arg Leu Asn Glu Thr Thr Gly Ser Val Glu Ser Ala Thr Cys
            645                 650                 655

Cys Ser Asp Ser Ala Pro Glu His Arg Met Phe Ala Lys Leu Ile Ala
        660                 665                 670

Asp Ser Leu Ala Val Trp Thr Thr Asp Tyr Lys Ile Asp Gly Phe Arg
    675                 680                 685

Phe Asp Leu Met Gly Tyr His Pro Lys Ala Gln Ile Leu Ser Ala Trp
690                 695                 700

Glu Arg Ile Lys Ala Leu Asn Pro Asp Ile Tyr Phe Phe Gly Glu Gly
705                 710                 715                 720
```

-continued

Trp Asp Ser Asn Gln Ser Asp Arg Phe Glu Ile Ala Ser Gln Ile Asn
                725                 730                 735

Leu Lys Gly Thr Gly Ile Gly Thr Phe Ser Asp Arg Leu Arg Asp Ala
            740                 745                 750

Val Arg Gly Gly Gly Pro Phe Asp Ser Gly Asp Ala Leu Arg Gln Asn
        755                 760                 765

Gln Gly Val Gly Ser Gly Ala Gly Val Leu Pro Asn Glu Leu Thr Thr
    770                 775                 780

Leu Thr Asp Asp Gln Ala Arg His Leu Ala Asp Leu Thr Arg Leu Gly
785                 790                 795                 800

Met Ala Gly Asn Leu Ala Asp Phe Val Leu Ile Asp Lys Asp Gly Ala
                805                 810                 815

Val Lys Arg Gly Ser Gly Ile Asp Tyr Asn Gly Ala Pro Gly Gly Tyr
            820                 825                 830

Ala Ala Asp Pro Thr Glu Val Val Asn Tyr Val Ser Lys His Asp Asn
        835                 840                 845

Gln Thr Leu Trp Asp Met Ile Ser Tyr Lys Ala Ala Gln Glu Ala Asp
    850                 855                 860

Leu Asp Thr Arg Val Arg Met Gln Ala Val Ser Leu Ala Thr Val Met
865                 870                 875                 880

Leu Gly Gln Gly Ile Ala Phe Asp Gln Gln Gly Ser Glu Leu Leu Arg
                885                 890                 895

Ser Lys Ser Phe Thr Arg Asp Ser Tyr Asp Ser Gly Asp Trp Phe Asn
            900                 905                 910

Arg Val Asp Tyr Ser Leu Gln Asp Asn Asn Tyr Asn Val Gly Met Pro
        915                 920                 925

Arg Ser Ser Asp Asp Gly Ser Asn Tyr Asp Ile Ile Ala Arg Val Lys
    930                 935                 940

Asp Trp Val Ala Thr Pro Gly Glu Ala Glu Leu Lys Gln Met Thr Ala
945                 950                 955                 960

Phe Tyr Gln Glu Leu Thr Ala Leu Arg Lys Ser Ser Pro Leu Phe Thr
                965                 970                 975

Leu Gly Asp Gly Ala Thr Val Met Gln Arg Val Asp Phe Arg Asn Thr
            980                 985                 990

Gly Ala Asp Gln Gln Thr Gly Leu Leu Val Met Thr Ile Asp Asp Gly
        995                 1000                1005

Ile Gln Ala Gly Ala Ser Leu Asp Ser Arg Val Asp Gly Ile Val
    1010                1015                1020

Val Ala Ile Asn Ala Ala Pro Glu Ser Arg Thr Leu Gln Asp Phe
    1025                1030                1035

Ala Gly Thr Ser Leu Gln Leu Ser Ala Ile Gln Gln Ala Ala Gly
    1040                1045                1050

Asp Arg Ser Leu Ala Ser Gly Val Gln Val Ala Ala Asp Gly Ser
    1055                1060                1065

Val Thr Leu Pro Ala Trp Ser Val Ala Val Leu Glu Leu Pro Gln
    1070                1075                1080

Gly Glu Ser Gln Gly Ala Gly Leu Pro Val Ser Ser Lys
    1085                1090                1095

<210> SEQ ID NO 29
<211> LENGTH: 843
<212> TYPE: PRT
<213> ORGANISM: Thermotoga maritima

<400> SEQUENCE: 29

-continued

```
Met Lys Thr Lys Leu Trp Leu Leu Leu Val Leu Leu Leu Ser Ala Leu
1               5                   10                  15
Ile Phe Ser Glu Thr Thr Ile Val His Tyr His Arg Tyr Asp Gly
            20                  25                  30
Lys Tyr Asp Gly Trp Asn Leu Trp Ile Trp Pro Val Glu Pro Val Ser
            35                  40                  45
Gln Glu Gly Lys Ala Tyr Gln Phe Thr Gly Glu Asp Asp Phe Gly Lys
        50                  55                  60
Val Ala Val Val Lys Leu Pro Met Asp Leu Thr Lys Val Gly Ile Ile
65                  70                  75                  80
Val Arg Leu Asn Glu Trp Gln Ala Lys Asp Val Ala Lys Asp Arg Phe
                85                  90                  95
Ile Glu Ile Lys Asp Gly Lys Ala Glu Val Trp Ile Leu Gln Gly Val
            100                 105                 110
Glu Glu Ile Phe Tyr Glu Lys Pro Asp Thr Ser Pro Arg Ile Phe Phe
            115                 120                 125
Ala Gln Ala Arg Ser Asn Lys Val Ile Glu Ala Phe Leu Thr Asn Pro
        130                 135                 140
Val Asp Thr Lys Lys Glu Leu Phe Lys Val Thr Val Asp Gly Lys
145                 150                 155                 160
Glu Ile Pro Val Ser Arg Val Glu Lys Ala Asp Pro Thr Asp Ile Asp
                165                 170                 175
Val Thr Asn Tyr Val Arg Ile Val Leu Ser Glu Ser Leu Lys Glu Glu
            180                 185                 190
Asp Leu Arg Lys Asp Val Glu Leu Ile Ile Glu Gly Tyr Lys Pro Ala
        195                 200                 205
Arg Val Ile Met Met Glu Ile Leu Asp Asp Tyr Tyr Asp Gly Glu
        210                 215                 220
Leu Gly Ala Val Tyr Ser Pro Glu Lys Thr Ile Phe Arg Val Trp Ser
225                 230                 235                 240
Pro Val Ser Lys Trp Val Lys Val Leu Leu Phe Lys Asn Gly Glu Asp
                245                 250                 255
Thr Glu Pro Tyr Gln Val Asn Met Glu Tyr Lys Gly Asn Gly Val
            260                 265                 270
Trp Glu Ala Val Glu Gly Asp Leu Asp Gly Val Phe Tyr Leu Tyr
        275                 280                 285
Gln Leu Glu Asn Tyr Gly Lys Ile Arg Thr Thr Val Asp Pro Tyr Ser
        290                 295                 300
Lys Ala Val Tyr Ala Asn Ser Lys Lys Ser Ala Val Val Asn Leu Ala
305                 310                 315                 320
Arg Thr Asn Pro Glu Gly Trp Glu Asn Asp Arg Gly Pro Lys Ile Glu
                325                 330                 335
Gly Tyr Glu Asp Ala Ile Ile Tyr Glu Ile His Ile Ala Asp Ile Thr
            340                 345                 350
Gly Leu Glu Asn Ser Gly Val Lys Asn Lys Gly Leu Tyr Leu Gly Leu
        355                 360                 365
Thr Glu Glu Asn Thr Lys Gly Pro Gly Val Thr Thr Gly Leu Ser
        370                 375                 380
His Leu Val Glu Leu Gly Val Thr His Val His Ile Leu Pro Phe Phe
385                 390                 395                 400
Asp Phe Tyr Thr Gly Asp Glu Leu Asp Lys Asp Phe Glu Lys Tyr Tyr
            405                 410                 415
```

```
Asn Trp Gly Tyr Asp Pro Tyr Leu Phe Met Val Pro Glu Gly Arg Tyr
            420                 425                 430

Ser Thr Asp Pro Lys Asn Pro His Thr Arg Ile Arg Glu Val Lys Glu
        435                 440                 445

Met Val Lys Ala Leu His Lys His Gly Ile Gly Val Ile Met Asp Met
    450                 455                 460

Val Phe Pro His Thr Tyr Gly Ile Gly Glu Leu Ser Ala Phe Asp Gln
465                 470                 475                 480

Thr Val Pro Tyr Tyr Phe Tyr Arg Ile Asp Lys Thr Gly Ala Tyr Leu
                485                 490                 495

Asn Glu Ser Gly Cys Gly Asn Val Ile Ala Ser Glu Arg Pro Met Met
            500                 505                 510

Arg Lys Phe Ile Val Asp Thr Val Thr Tyr Trp Val Lys Glu Tyr His
        515                 520                 525

Ile Asp Gly Phe Arg Phe Asp Gln Met Gly Leu Ile Asp Lys Lys Thr
    530                 535                 540

Met Leu Glu Val Glu Arg Ala Leu His Lys Ile Asp Pro Thr Ile Ile
545                 550                 555                 560

Leu Tyr Gly Glu Pro Trp Gly Gly Trp Gly Ala Pro Ile Arg Phe Gly
                565                 570                 575

Lys Ser Asp Val Ala Gly Thr His Val Ala Ala Phe Asn Asp Glu Phe
            580                 585                 590

Arg Asp Ala Ile Arg Gly Ser Val Phe Asn Pro Ser Val Lys Gly Phe
        595                 600                 605

Val Met Gly Gly Tyr Gly Lys Glu Thr Lys Ile Lys Arg Gly Val Val
    610                 615                 620

Gly Ser Ile Asn Tyr Asp Gly Lys Leu Ile Lys Ser Phe Ala Leu Asp
625                 630                 635                 640

Pro Glu Glu Thr Ile Asn Tyr Ala Ala Cys His Asp Asn His Thr Leu
                645                 650                 655

Trp Asp Lys Asn Tyr Leu Ala Ala Lys Ala Asp Lys Lys Lys Glu Trp
            660                 665                 670

Thr Glu Glu Leu Lys Asn Ala Gln Lys Leu Ala Gly Ala Ile Leu
        675                 680                 685

Leu Thr Ser Gln Gly Val Pro Phe Leu His Gly Gly Gln Asp Phe Cys
    690                 695                 700

Arg Thr Lys Asn Phe Asn Asp Asn Ser Tyr Asn Ala Pro Ile Ser Ile
705                 710                 715                 720

Asn Gly Phe Asp Tyr Glu Arg Lys Leu Gln Phe Ile Asp Val Phe Asn
                725                 730                 735

Tyr His Lys Gly Leu Ile Lys Leu Arg Lys Glu His Pro Ala Phe Arg
            740                 745                 750

Leu Lys Asn Ala Glu Glu Ile Lys Lys His Leu Glu Phe Leu Pro Gly
        755                 760                 765

Gly Arg Arg Ile Val Ala Phe Met Leu Lys Asp His Ala Gly Gly Asp
    770                 775                 780

Pro Trp Lys Asp Ile Val Val Ile Tyr Asn Gly Asn Leu Glu Lys Thr
785                 790                 795                 800

Thr Tyr Lys Leu Pro Glu Gly Lys Trp Asn Val Val Asn Ser Gln
                805                 810                 815

Lys Ala Gly Thr Glu Val Ile Glu Thr Val Glu Gly Thr Ile Glu Leu
            820                 825                 830

Asp Pro Leu Ser Ala Tyr Val Leu Tyr Arg Glu
```

<210> SEQ ID NO 30
<211> LENGTH: 717
<212> TYPE: PRT
<213> ORGANISM: Escherichia coli

<400> SEQUENCE: 30

```
Asn Glu Ile Lys Ala Ile Phe Thr Thr Leu Asp Gly Leu Asp Glu Asp
 1               5                  10                  15
Ala Val Lys Gln Asn Ile Lys Ile Thr Asp Lys Ala Gly Lys Thr Val
             20                  25                  30
Ala Ile Asp Glu Leu Thr Leu Asp Lys Asp Lys Ser Val Met Thr Leu
         35                  40                  45
Lys Gly Asp Phe Lys Ala Gln Gly Ala Val Tyr Thr Val Thr Phe Gly
     50                  55                  60
Glu Val Ser Gln Val Ala Arg Gln Ser Trp Gln Leu Lys Asp Lys Leu
 65                  70                  75                  80
Tyr Ala Tyr Asp Gly Glu Leu Gly Ala Thr Leu Ala Lys Asp Gly Ser
                 85                  90                  95
Val Asp Leu Ala Leu Trp Ser Pro Ser Ala Asp Thr Val Lys Val Val
            100                 105                 110
Val Tyr Asp Lys Gln Asp Gln Thr Lys Val Ile Gly Gln Ala Asp Leu
        115                 120                 125
Thr Lys Ser Glu Lys Gly Val Trp Arg Ala His Leu Thr Ser Asp Ser
    130                 135                 140
Val Lys Gly Ile Ser Asp Tyr Thr Gly Tyr Tyr Tyr Leu Tyr Glu Ile
145                 150                 155                 160
Thr Arg Gly Gln Glu Lys Val Met Val Leu Asp Pro Tyr Ala Lys Ser
                165                 170                 175
Leu Ala Ala Trp Asn Asp Ala Thr Ala Thr Asp Ile Lys Thr Ala
            180                 185                 190
Lys Ala Ala Phe Ile Asp Pro Ser Lys Leu Gly Pro Thr Gly Leu Asp
        195                 200                 205
Phe Ala Lys Ile Asn Asn Phe Lys Lys Arg Glu Asp Ala Ile Ile Tyr
    210                 215                 220
Glu Ala His Val Arg Asp Phe Lys Ser Asp Lys Ala Leu Glu Gly Lys
225                 230                 235                 240
Leu Thr His Pro Phe Gly Thr Phe Ser Ala Phe Val Glu Gln Leu Asp
                245                 250                 255
Tyr Leu Lys Asp Leu Gly Val Thr His Val Gln Leu Leu Pro Val Leu
            260                 265                 270
Ser Tyr Phe Tyr Ala Asn Glu Leu Asp Lys Ser Arg Ser Thr Ala Tyr
        275                 280                 285
Thr Ser Ser Asp Asn Asn Tyr Asn Trp Gly Tyr Asp Pro Gln His Tyr
    290                 295                 300
Phe Ala Leu Ser Gly Met Tyr Ser Ala Asn Pro Asn Asp Pro Ala Leu
305                 310                 315                 320
Arg Ile Ala Glu Leu Lys Asn Leu Val Asn Glu Ile His Lys Arg Gly
                325                 330                 335
Met Gly Val Ile Phe Asp Val Val Tyr Asn His Thr Ala Arg Thr Tyr
            340                 345                 350
Leu Phe Glu Asp Leu Glu Pro Asn Tyr Tyr His Phe Met Asn Ala Asp
        355                 360                 365
```

Gly Thr Ala Arg Glu Ser Phe Gly Gly Arg Leu Gly Thr Thr His
370                 375                 380

Ala Met Ser Arg Arg Ile Leu Val Asp Ser Ile Thr Tyr Leu Thr Arg
385                 390                 395                 400

Glu Phe Lys Val Asp Gly Phe Arg Phe Asp Met Met Gly Asp His Asp
                405                 410                 415

Ala Ala Ala Ile Glu Gln Ala Phe Lys Ala Ala Lys Ala Ile Asn Pro
                420                 425                 430

Asn Thr Ile Met Ile Gly Glu Gly Trp Arg Thr Tyr Gln Gly Asp Glu
            435                 440                 445

Gly Lys Lys Glu Ile Ala Ala Asp Gln Asp Trp Met Lys Ala Thr Asn
450                 455                 460

Thr Val Gly Val Phe Ser Asp Asp Ile Arg Asn Thr Leu Lys Ser Gly
465                 470                 475                 480

Phe Pro Asn Glu Gly Thr Ala Ala Phe Ile Thr Gly Gly Ala Lys Asn
                485                 490                 495

Leu Glu Gly Leu Phe Lys Thr Ile Lys Ala Gln Pro Ser Asn Phe Glu
            500                 505                 510

Ala Asp Ala Pro Gly Asp Val Val Gln Tyr Ile Ala Ala His Asp Asn
        515                 520                 525

Leu Thr Leu His Asp Val Ile Ala Lys Ser Ile Asn Lys Asp Pro Lys
530                 535                 540

Val Ala Glu Glu Glu Ile His Lys Arg Ile Arg Leu Gly Asn Thr Met
545                 550                 555                 560

Ile Leu Thr Ala Gln Gly Thr Ala Phe Ile His Ser Gly Gln Glu Tyr
                565                 570                 575

Gly Arg Thr Lys Gln Leu Leu Asn Pro Asp Tyr Lys Thr Lys Val Ser
            580                 585                 590

Asp Asp Lys Val Pro Asn Lys Ala Thr Leu Ile Asp Ala Val Ala Gln
        595                 600                 605

Tyr Pro Tyr Phe Ile His Asp Ser Tyr Asp Ser Asp Ala Val Asn
    610                 615                 620

His Phe Asp Trp Ala Lys Ala Thr Asp Ser Ile Ala His Pro Ile Ser
625                 630                 635                 640

Asn Gln Thr Lys Ala Tyr Thr Gln Gly Leu Ile Ala Leu Arg Arg Ser
                645                 650                 655

Thr Asp Ala Phe Thr Lys Ala Thr Lys Ala Glu Val Asp Arg Asp Val
            660                 665                 670

Thr Leu Ile Thr Gln Ala Gly Gln Asp Gly Ile Gln Gln Glu Asp Leu
        675                 680                 685

Ile Met Gly Tyr Gln Thr Val Ala Ser Asn Glu Asp Arg Tyr Ala Val
690                 695                 700

Phe Val Asn Ala Asp Asn Lys Thr Arg Lys Ala Val Leu
705                 710                 715

<210> SEQ ID NO 31
<211> LENGTH: 1102
<212> TYPE: PRT
<213> ORGANISM: Enterobacter aerogenes

<400> SEQUENCE: 31

Met Leu Arg Tyr Thr Cys His Ala Leu Phe Leu Gly Ser Leu Val Leu
1               5                   10                  15

Leu Ser Gly Cys Asp Asn Ser Ser Ser Ser Thr Ser Gly Ser Pro
            20                  25                  30

-continued

```
Gly Ser Pro Gly Asn Pro Gly Asn Pro Gly Thr Pro Gly Thr Pro Asp
        35                  40                  45
Pro Gln Asp Val Val Arg Leu Pro Asp Val Ala Val Pro Gly Glu
 50                  55                  60
Ala Val Gln Ala Ser Ala Arg Gln Ala Val Ile His Leu Val Asp Ile
 65                  70                  75                  80
Ala Gly Ile Thr Ser Ser Thr Pro Ala Asp Tyr Ala Thr Lys Asn Leu
                     85                  90                  95
Tyr Leu Trp Asn Asn Glu Thr Cys Asp Ala Leu Ser Ala Pro Val Ala
             100                 105                 110
Asp Trp Asn Asp Val Ser Thr Thr Pro Thr Gly Ser Asp Lys Tyr Gly
             115                 120                 125
Pro Tyr Trp Val Ile Pro Leu Thr Lys Glu Ser Gly Cys Ile Asn Val
         130                 135                 140
Ile Val Arg Asp Gly Thr Asn Lys Leu Ile Asp Ser Asp Leu Arg Val
145                 150                 155                 160
Ser Phe Ser Asp Phe Thr Asp Arg Thr Val Ser Val Ile Ala Gly Asn
                 165                 170                 175
Ser Ala Val Tyr Asp Ser Arg Ala Asp Ala Phe Arg Ala Ala Phe Gly
             180                 185                 190
Val Ala Leu Ala Asp Ala His Trp Val Asp Lys Thr Thr Leu Leu Trp
             195                 200                 205
Pro Gly Gly Glu Asn Lys Pro Ile Val Arg Leu Tyr Tyr Ser His Ser
         210                 215                 220
Ser Lys Val Ala Ala Asp Ser Asn Gly Glu Phe Ser Asp Lys Tyr Val
225                 230                 235                 240
Lys Leu Thr Pro Thr Thr Val Asn Gln Gln Val Ser Met Arg Phe Pro
                 245                 250                 255
His Leu Ala Ser Tyr Pro Ala Phe Lys Leu Pro Asp Asp Val Asn Val
             260                 265                 270
Asp Glu Leu Leu Gln Gly Glu Thr Val Ala Ile Ala Ala Glu Ser Asp
         275                 280                 285
Gly Ile Leu Ser Ser Ala Thr Gln Val Gln Thr Ala Gly Val Leu Asp
     290                 295                 300
Asp Thr Tyr Ala Ala Ala Ala Glu Ala Leu Ser Tyr Gly Ala Gln Leu
305                 310                 315                 320
Thr Asp Ser Gly Val Thr Phe Arg Val Trp Ala Pro Thr Ala Gln Gln
                 325                 330                 335
Val Glu Leu Val Ile Tyr Ser Ala Asp Lys Lys Val Ile Ala Ser His
             340                 345                 350
Pro Met Thr Arg Asp Ser Ala Ser Gly Ala Trp Ser Trp Gln Gly Gly
         355                 360                 365
Ser Asp Leu Lys Gly Ala Phe Tyr Arg Tyr Ala Met Thr Val Tyr His
     370                 375                 380
Pro Gln Ser Arg Lys Val Glu Gln Tyr Glu Val Thr Asp Pro Tyr Ala
385                 390                 395                 400
His Ser Leu Ser Thr Asn Ser Glu Tyr Ser Gln Val Val Asp Leu Asn
                 405                 410                 415
Asp Ser Ala Leu Lys Pro Glu Gly Trp Asp Gly Leu Thr Met Pro His
             420                 425                 430
Ala Gln Lys Thr Lys Ala Asp Leu Ala Lys Met Thr Ile His Glu Ser
         435                 440                 445
```

-continued

```
His Ile Arg Asp Leu Ser Ala Trp Asp Gln Thr Val Pro Ala Glu Leu
450                 455                 460
Arg Gly Lys Tyr Leu Ala Leu Thr Ala Gln Glu Ser Asn Met Val Gln
465                 470                 475                 480
His Leu Lys Gln Leu Ser Ala Ser Gly Val Thr His Ile Glu Leu Leu
            485                 490                 495
Pro Val Phe Asp Leu Ala Thr Val Asn Glu Phe Ser Asp Lys Val Ala
        500                 505                 510
Asp Ile Gln Gln Pro Phe Ser Arg Leu Cys Glu Val Asn Ser Ala Val
    515                 520                 525
Lys Ser Ser Glu Phe Ala Gly Tyr Cys Asp Ser Gly Ser Thr Val Glu
530                 535                 540
Glu Val Leu Thr Gln Leu Lys Gln Asn Asp Ser Lys Asp Asn Pro Gln
545                 550                 555                 560
Val Gln Ala Leu Asn Thr Leu Val Ala Gln Thr Asp Ser Tyr Asn Trp
            565                 570                 575
Gly Tyr Asp Pro Phe His Tyr Thr Val Pro Glu Gly Ser Tyr Ala Thr
        580                 585                 590
Asp Pro Glu Gly Thr Ala Arg Ile Lys Glu Phe Arg Thr Met Ile Gln
    595                 600                 605
Ala Ile Lys Gln Asp Leu Gly Met Asn Val Ile Met Asp Val Val Tyr
610                 615                 620
Asn His Thr Asn Ala Ala Gly Pro Thr Asp Arg Thr Ser Val Leu Asp
625                 630                 635                 640
Lys Ile Val Pro Trp Tyr Tyr Gln Arg Leu Asn Glu Thr Thr Gly Ser
            645                 650                 655
Val Glu Ser Ala Thr Cys Cys Ser Asp Ser Ala Pro Glu His Arg Met
        660                 665                 670
Phe Ala Lys Leu Ile Ala Asp Ser Leu Ala Val Trp Thr Thr Asp Tyr
    675                 680                 685
Lys Ile Asp Gly Phe Arg Phe Asp Leu Met Gly Tyr His Pro Lys Ala
690                 695                 700
Gln Ile Leu Ser Ala Trp Glu Arg Ile Lys Ala Leu Asn Pro Asp Ile
705                 710                 715                 720
Tyr Phe Phe Gly Glu Gly Trp Asp Ser Asn Gln Ser Asp Arg Phe Glu
            725                 730                 735
Ile Ala Ser Gln Ile Asn Leu Lys Gly Thr Gly Ile Gly Thr Phe Ser
        740                 745                 750
Asp Arg Leu Arg Asp Ala Val Arg Gly Gly Pro Phe Asp Ser Gly
    755                 760                 765
Asp Ala Leu Arg Gln Asn Gln Gly Val Gly Ser Gly Ala Gly Val Leu
770                 775                 780
Pro Asn Glu Leu Thr Thr Leu Ser Asp Asp Gln Ala Arg His Leu Ala
785                 790                 795                 800
Asp Leu Thr Arg Leu Gly Met Ala Gly Asn Leu Ala Asp Phe Val Leu
            805                 810                 815
Ile Asp Lys Asp Gly Ala Val Lys Arg Gly Ser Glu Ile Asp Tyr Asn
        820                 825                 830
Gly Ala Pro Gly Gly Tyr Ala Ala Asp Pro Thr Glu Val Val Asn Tyr
    835                 840                 845
Val Ser Lys His Asp Asn Gln Thr Leu Trp Asp Met Ile Ser Tyr Lys
850                 855                 860
Ala Ala Gln Glu Ala Asp Leu Asp Thr Arg Val Arg Met Gln Ala Val
```

```
                865                 870                 875                 880
        Ser Leu Ala Thr Val Met Leu Gly Gln Gly Ile Ala Phe Asp Gln Gln
                        885                 890                 895

Gly Ser Glu Leu Val Arg Ser Lys Ser Phe Thr Arg Asp Ser Tyr Asp
                        900                 905                 910

Ser Gly Asp Trp Phe Asn Arg Val Asp Tyr Ser Leu Gln Asp Asn Asn
                        915                 920                 925

Tyr Asn Val Gly Met Pro Arg Ser Ser Asp Gly Ser Asn Tyr Asp
                        930                 935                 940

Ile Ile Ala Arg Val Lys Asp Ala Val Ala Thr Pro Gly Glu Thr Glu
        945                 950                 955                 960

Leu Lys Gln Met Thr Ala Phe Tyr Gln Glu Leu Thr Ala Leu Arg Lys
                        965                 970                 975

Ser Ser Pro Leu Phe Thr Leu Gly Asp Gly Ala Thr Val Met Lys Arg
                        980                 985                 990

Val Asp Phe Arg Asn Thr Gly Ala Asp Gln Gln Thr Gly Leu Leu Val
                        995                1000                1005

Met Thr Ile Asp Asp Gly Met Gln Ala Gly Ala Ser Leu Asp Ser
                1010                1015                1020

Arg Val Asp Gly Ile Val Val Ala Ile Asn Ala Ala Pro Glu Ser
                1025                1030                1035

Arg Thr Leu Gln Asp Phe Ala Gly Thr Ser Leu Gln Leu Ser Ala
                1040                1045                1050

Ile Gln Gln Ala Ala Gly Asp Arg Ser Leu Ala Ser Gly Val Gln
                1055                1060                1065

Val Ala Ala Asp Gly Ser Val Thr Leu Pro Ala Trp Ser Val Ala
                1070                1075                1080

Val Leu Glu Leu Pro Gln Gly Glu Ser Gln Gly Ala Gly Leu Pro
                1085                1090                1095

Val Ser Ser Lys
                1100

<210> SEQ ID NO 32
<211> LENGTH: 710
<212> TYPE: PRT
<213> ORGANISM: Bacillus atrophaeus

<400> SEQUENCE: 32

Met Val Cys Leu Asn Arg Lys Phe Glu Ala Tyr Leu Asp Glu Met Asp
        1               5                  10                  15

Val Ile Thr Val Leu Ile Pro Ser Gly Lys Lys Glu Lys Tyr Thr Leu
                        20                  25                  30

Pro Phe Val Leu Glu Thr Glu Ala Gly Asp Val Ser Leu Ser Ile Arg
                        35                  40                  45

Ala Glu Cys His Ile Asp Gly Lys Tyr Lys Tyr Ile Leu Val Ser Glu
                        50                  55                  60

His Pro Val Ser Leu Gly Lys Thr His Tyr Ile Arg Ala Ser Gly Gly
        65                  70                  75                  80

Asp Lys Thr Asp Leu Gln Ile Gly Ala Val Ile Arg Thr Glu Ala Phe
                        85                  90                  95

Asp Ser Gln Phe Tyr Phe Asp Gly Ala Leu Gly Ala Asp Tyr Thr Pro
                        100                 105                 110

Ser Arg Thr Val Phe Lys Val Trp Ala Pro Thr Ala Thr Ala
                        115                 120                 125
```

-continued

```
Val Lys Leu Thr His Pro Glu Gln Gln Gly Leu Val Leu Gln Met Thr
130                 135                 140
Arg Gln Asp His Gly Val Phe Ala Ala Leu Val Asp Gly Asp Leu His
145                 150                 155                 160
Gly Tyr Glu Tyr Val Tyr Arg Ile Cys Asn Asn Leu Glu Trp Thr Glu
                165                 170                 175
Thr Val Asp Pro Tyr Ala Lys Ala Val Thr Ile Asn Gly Glu Lys Gly
                    180                 185                 190
Val Val Leu Arg Pro Glu Asn Pro His Ile Thr Ser Gln Gly Ile Pro
            195                 200                 205
Phe Ser Asn Pro Ala Asp Ala Val Ile Tyr Glu Leu His Ile Arg Asp
210                 215                 220
Phe Ser Ile His Glu Asn Ser Gly Met Lys Lys Gly Gln Tyr Leu
225                 230                 235                 240
Ala Met Thr Glu Thr Asp Ala Lys Thr Gln Glu Gly Val Ser Ala Gly
                245                 250                 255
Leu Ser Tyr Leu Lys Glu Leu Gly Val Thr His Ile Glu Leu Leu Pro
            260                 265                 270
Val Asn Asp Phe Ala Gly Val Asp Glu Lys Asn Pro Leu Ala Ala Tyr
        275                 280                 285
Asn Trp Gly Tyr Asn Pro Leu His Phe Phe Ala Pro Glu Gly Ser Tyr
    290                 295                 300
Ser Ser Asp Pro Tyr Asn Pro Gln Val Arg Lys Ser Glu Leu Lys Glu
305                 310                 315                 320
Leu Ile Gln Thr Leu His Gln Asn Gly Leu Gln Val Ile Leu Asp Val
                325                 330                 335
Val Tyr Asn His Val Tyr Lys Arg Glu His Ser Pro Phe Glu Asn Thr
                340                 345                 350
Val Pro Gly Tyr Phe Phe Arg His Asp Ala Asp Gly Met Pro Ser Asn
            355                 360                 365
Gly Thr Gly Val Gly Asn Asp Ile Ala Ser Glu Arg Leu Met Ala Arg
        370                 375                 380
Lys Tyr Ile Ile Asp Cys Val Val His Trp Leu Lys Glu Tyr Asp Ala
385                 390                 395                 400
Asp Gly Phe Arg Phe Asp Leu Met Gly Ile Leu Asp Ile Asp Thr Ile
                405                 410                 415
Arg Gln Ile Arg Glu Arg Ala Leu Ala Val Lys Pro Gly Ile Leu Leu
                420                 425                 430
Phe Gly Glu Gly Trp Asn Leu Asp Thr Pro Ile Ser Asp Asp Lys Lys
            435                 440                 445
Ala Thr Leu Ala Asn Ala Phe Gln Leu Pro Gly Ile Gly Phe Phe Asn
450                 455                 460
Asp Ser Phe Arg Asp Ala Val Lys Gly Ser Thr Phe Gln Arg Glu Ala
465                 470                 475                 480
Ala Gly Phe Ala Leu Gly Asn Gly Asp Gln Ile Asp Ala Val Ile His
                485                 490                 495
Gly Ile Thr Gly Ser Ala Gly Trp Lys Glu Thr Asp Pro Ile Val Gln
            500                 505                 510
Glu Pro Ser Gln Ser Val Asn Tyr Val Glu Ser His Asp Asn His Thr
        515                 520                 525
Phe Trp Asp Lys Met Gln Tyr Ala Leu Pro His Glu Thr Asp Ser Val
    530                 535                 540
Lys Arg Ser Arg Gln Lys Leu Ala Thr Ala Val Val Leu Leu Ala Gln
```

-continued

```
                545                 550                 555                 560
Gly Ile Pro Phe Ile His Ser Gly Gln Glu Phe Phe Arg Thr Lys Gln
                    565                 570                 575

Gly Asp Glu Asn Ser Tyr Gln Ser Gly Asp Ser Val Asn Arg Leu Asp
                580                 585                 590

Trp Thr Arg Arg Ser Glu Phe Arg Glu Asp Val Glu Tyr Val Arg Arg
            595                 600                 605

Leu Ile Glu Ile Arg Lys Ala His Pro Ala Phe Arg Leu Lys Arg Ala
        610                 615                 620

Ala Glu Val Val Arg His Leu Asp Phe Leu Glu Ala Arg Gly His Leu
625                 630                 635                 640

Ile Ala Tyr Arg Leu Phe Asp Leu Glu Ala Met Asp Glu Trp Lys Glu
                645                 650                 655

Ile Ile Ile Val His His Ser Ser Pro Asp Lys Ala Glu Met Met Leu
                660                 665                 670

Pro Ala Gly Lys Thr Tyr Arg Leu Leu Cys Asp Pro Ser Gly Phe Arg
            675                 680                 685

Glu Gln Pro Lys Glu Ile Lys Glu Glu Leu Ile Ile Glu Gly Ile Gly
        690                 695                 700

Thr Cys Ile Leu Tyr Ile
705                 710

<210> SEQ ID NO 33
<211> LENGTH: 711
<212> TYPE: PRT
<213> ORGANISM: Unknown
<220> FEATURE:
<223> OTHER INFORMATION: bacterial

<400> SEQUENCE: 33

Met Val Ser Ile Gln Arg Arg Phe Glu Ala Tyr Ala Asp Glu Met Asn
1               5                   10                  15

Ile Ile Thr Val Leu Ile Pro Ala Asp Gln Lys Asp Thr Phe Thr Pro
                20                  25                  30

Pro Phe Gln Leu Glu Thr Asp Thr Gly Glu Ile Pro Leu Thr Val Ser
            35                  40                  45

Gln Glu Trp Lys Ile Glu Gly Lys Tyr Lys Tyr Val Cys Val Ala Glu
        50                  55                  60

Gln Pro Val Thr Phe Gly Lys Thr His Tyr Val Lys Ala Ser Gly Gly
65                  70                  75                  80

Gly Val Thr Asp Leu Gln Ile Gly Ala Val Ile Arg Thr Asp Pro Phe
                85                  90                  95

Asp Ala Ala Phe Tyr Tyr Asp Gly Glu Leu Gly Ala Val Tyr Thr Ser
            100                 105                 110

Asp Tyr Thr Glu Phe Lys Val Trp Ala Pro Ala Ala Thr Ser Ala Ala
        115                 120                 125

Val Lys Leu Ser His Pro Glu Lys Ser Gly His Thr Phe Gln Met Thr
    130                 135                 140

Arg Met Glu Asn Gly Val Tyr Ala Val Thr Val Val Gly Asp Leu His
145                 150                 155                 160

Gly Tyr Glu Tyr Val Tyr Trp Ile Cys Asn Asn Leu Glu Trp Thr Glu
                165                 170                 175

Thr Val Asp Pro Tyr Ala Lys Ala Val Thr Val Asn Gly Glu Lys Gly
            180                 185                 190

Val Val Leu Arg Pro Asp Gln Ala Asn Ser Ala Pro Ser Leu Thr Pro
```

```
                195                 200                 205
      Phe Ser Asp Pro Val Asp Ala Ile Ile Tyr Glu Met His Val Arg Asp
          210                 215                 220

Phe Ser Ile His Glu Asn Ser Gly Met Lys Asn Lys Gly Lys Tyr Ala
      225                 230                 235                 240

Ala Leu Ala Glu Thr Gly Thr Gln Thr Lys Asn Gly Ser Ser Thr Gly
                      245                 250                 255

Leu Ser Tyr Leu Lys Glu Leu Gly Val Thr His Ile Glu Leu Leu Pro
                  260                 265                 270

Val Asn Asp Tyr Ala Gly Val Asn Glu Glu Thr Pro Leu Ala Ala Tyr
                  275                 280                 285

Asn Trp Gly Tyr Asn Pro Leu His Phe Phe Ala Pro Glu Gly Ser Tyr
                  290                 295                 300

Ala Ser Asn Pro His Asp Pro Gln Thr Arg Asn Lys Glu Val Lys Gln
      305                 310                 315                 320

Met Ile His Thr Leu His Arg His Gly Leu Arg Val Ile Leu Asp Val
                      325                 330                 335

Val Tyr Asn His Val Tyr Gln Arg Glu His Ser Pro Phe Glu Lys Thr
                  340                 345                 350

Val Pro Gly Tyr Phe Phe Arg His Asp Gln Phe Gly Met Pro Ser Asn
                  355                 360                 365

Gly Thr Gly Val Gly Asn Asp Ile Ala Ser Glu Arg Arg Met Ala Arg
                  370                 375                 380

Lys Phe Ile Thr Asp Cys Val Leu Tyr Trp Leu Lys Glu Tyr Asp Val
      385                 390                 395                 400

Asp Gly Phe Arg Phe Asp Leu Leu Gly Ile Leu Asp Ile Glu Thr Val
                      405                 410                 415

Leu His Ile Lys Glu Lys Ala Phe Glu Val Lys Pro Gly Ile Leu Leu
                  420                 425                 430

Phe Gly Glu Gly Trp Asp Leu Ala Thr Pro Leu Pro Pro Asp Gln Lys
                  435                 440                 445

Ala Thr Leu Ala Asn Ala Ser Lys Met Pro Gly Val Gly Phe Phe Asn
      450                 455                 460

Asp Ser Phe Arg Asp Ala Val Lys Gly Asn Thr Phe Gln Ile Ala Ala
      465                 470                 475                 480

Ala Gly Phe Ala Leu Gly Asn Gly Glu Lys Ala Glu Thr Val Met His
                      485                 490                 495

Gly Ile Ala Gly Ser Ser Gly Trp Lys Glu Thr Ala Pro Leu Val Ser
                  500                 505                 510

Ala Pro Ser Gln Ser Ile Asn Tyr Val Glu Ser His Asp Asn His Thr
                  515                 520                 525

Phe Trp Asp Lys Met Ser Leu Ala Leu Pro Gln Glu Ser Asp Ser Arg
                  530                 535                 540

Lys Arg Ser Arg Gln Lys Leu Ala Thr Ala Ile Ile Leu Leu Ala Gln
      545                 550                 555                 560

Gly Val Pro Phe Ile His Ser Gly Gln Glu Phe Phe Arg Thr Lys Gln
                      565                 570                 575

Gly Val Glu Asn Ser Tyr Gln Ser Ser Asp Ser Ile Asn Gln Leu Asp
                  580                 585                 590

Trp Ser Arg Arg Glu Thr Phe Met Gln Asp Ala Asp Tyr Val Arg Lys
                  595                 600                 605

Leu Ile Ser Leu Arg Lys Ala His Pro Ala Phe Arg Leu Thr Ser Ser
                  610                 615                 620
```

```
Ala Asp Ile Gln Arg Ser Leu Glu Cys Leu Ala Leu Lys Glu His Leu
625                 630                 635                 640

Ile Val Tyr Arg Leu Phe Gly Leu Gly Ala Ile Asp Glu Trp Glu Glu
                645                 650                 655

Ile Ile Val Ile His His Ala Ser Pro Asp Ser Val Ile Trp Gln Leu
                660                 665                 670

Pro Lys Asp Lys Ala Tyr Arg Leu Leu Cys Asp Thr Asp Gly Phe Cys
                675                 680                 685

Ala Asp Pro Gly Glu Ile Lys Lys Ala Val Ala Val Asn Gly Ile Gly
690                 695                 700

Thr Val Ile Leu Tyr Leu Ala
705                 710

<210> SEQ ID NO 34
<211> LENGTH: 718
<212> TYPE: PRT
<213> ORGANISM: Bacillus sp.

<400> SEQUENCE: 34

Met Val Cys Ile Gln Arg Ser Phe Glu Ala Tyr Ala Asp Glu Met Asn
1               5                   10                  15

Ile Ile Thr Val Leu Ile Pro Ala Asp Gln Lys Asp Thr Phe Thr Pro
                20                  25                  30

Pro Phe Gln Leu Glu Thr Asp Thr Ala Glu Ile Pro Leu Ala Val Ser
            35                  40                  45

Gln Glu Trp Gln Ile Glu Gly Lys Tyr Lys Tyr Val Cys Val Ala Glu
    50                  55                  60

Gln Pro Val Ala Phe Gly Lys Thr His His Val Lys Ala Ser Gly Gly
65                  70                  75                  80

Gly Lys Thr Asp Leu Gln Ile Gly Ala Val Val Arg Thr Ala Ala Phe
                85                  90                  95

Asp Ala Ala Phe Tyr Tyr Asp Gly Glu Leu Gly Ala Val Tyr Ala Ser
                100                 105                 110

Asp Tyr Thr Glu Phe Lys Val Trp Ala Pro Ala Ala Thr Ser Ala Ala
            115                 120                 125

Val Lys Leu Ser His Pro Glu Lys Ser Gly His Thr Leu Gln Met Thr
130                 135                 140

Arg Met Glu Asn Gly Val Tyr Ala Val Thr Val Ala Gly Asp Leu His
145                 150                 155                 160

Gly Tyr Glu Tyr Val Tyr Arg Ile Cys Asn Asn Leu Glu Trp Thr Glu
                165                 170                 175

Thr Val Asp Pro Tyr Ala Lys Ala Val Thr Val Asn Gly Glu Lys Gly
            180                 185                 190

Val Val Leu Arg Pro Asp Gln Ala Asn Ser Ala Pro Ser Phe Thr Pro
    195                 200                 205

Phe Ser Asp Pro Val Asp Ala Ile Ile Tyr Glu Met His Ile Arg Asp
210                 215                 220

Phe Ser Ile His Glu Asn Ser Gly Met Lys Asn Lys Gly Lys Tyr Ala
225                 230                 235                 240

Ala Leu Ala Glu Thr Asp Thr Lys Thr Lys Asn Gly Ser Ser Thr Gly
                245                 250                 255

Leu Ser Tyr Leu Lys Glu Leu Gly Val Thr His Ile Glu Leu Leu Pro
            260                 265                 270

Leu Asn Asp Tyr Ala Gly Val Asp Glu Glu Asn Pro Leu Ala Ala Tyr
```

-continued

```
                275                 280                 285
Asn Trp Gly Tyr Asn Pro Leu His Phe Phe Ala Pro Glu Gly Ser Tyr
290                 295                 300
Ala Ser Asn Pro His Asp Pro Gln Thr Arg Asn Thr Glu Val Lys Gln
305                 310                 315                 320
Met Ile His Thr Leu His Gln His Gly Leu Arg Val Ile Leu Asp Val
                325                 330                 335
Val Tyr Asn His Val Tyr Gln Arg Glu His Ser Pro Phe Glu Lys Thr
            340                 345                 350
Val Pro Gly Tyr Phe Phe Arg His Asp Gln Phe Gly Met Pro Ser Asn
        355                 360                 365
Gly Thr Gly Val Gly Asn Asp Ile Ala Ser Glu Arg Met Ala Arg
370                 375                 380
Lys Phe Ile Thr Asp Cys Val Leu Tyr Trp Leu Lys Glu Tyr Asp Ile
385                 390                 395                 400
Asp Gly Phe Arg Phe Asp Leu Leu Gly Ile Leu Asp Ile Glu Thr Val
                405                 410                 415
Leu His Met Lys Glu Lys Ala Ser Glu Val Lys Pro Gly Ile Leu Leu
            420                 425                 430
Phe Gly Glu Gly Trp Asp Leu Ala Thr Pro Leu Pro Glu Gln Lys
        435                 440                 445
Ala Thr Leu Ala Asn Ala Ser Lys Met Pro Gly Val Gly Phe Phe Asn
450                 455                 460
Asp Ser Phe Arg Asp Ala Val Lys Gly Asn Thr Phe His Ile Ala Ala
465                 470                 475                 480
Ala Gly Phe Ala Leu Gly Asn Gly Glu Gln Thr Glu Thr Val Met Arg
                485                 490                 495
Gly Ile Ala Gly Ser Ser Gly Trp Glu Glu Thr Asp Pro Leu Val Ser
            500                 505                 510
Ala Pro Ser Gln Ser Ile Asn Tyr Val Glu Ser His Asp Asn His Thr
        515                 520                 525
Phe Trp Asp Lys Met Ser Leu Ala Leu Pro Gln Glu Ser Glu Ser Arg
530                 535                 540
Lys Arg Ser Arg Gln Lys Leu Ala Ser Ala Ile Ile Leu Leu Ala Gln
545                 550                 555                 560
Gly Val Pro Phe Ile His Ser Gly Gln Glu Phe Phe Arg Thr Lys Gln
                565                 570                 575
Gly Val Glu Asn Ser Tyr Gln Ser Ser Asp Ser Ile Asn Gln Leu Asp
            580                 585                 590
Trp Ser Arg Arg Glu Thr Phe Lys Gln Asp Val Asp Tyr Val Arg Arg
        595                 600                 605
Leu Ile Ser Leu Arg Lys Ala His Pro Ala Phe Arg Leu Thr Ser Ser
610                 615                 620
Ala Asp Ile Gln Arg Cys Leu Glu Cys Leu Ala Leu Lys Glu His Leu
625                 630                 635                 640
Ile Val Tyr Arg Leu Phe Asn Leu Gly Ala Ile Asp Glu Trp Glu Glu
                645                 650                 655
Ile Ile Val Ile His His Ala Ser Pro Asp Ser Val Thr Trp Gln Leu
            660                 665                 670
Pro Lys Asp Lys Ala Tyr Arg Leu Leu Cys Asp Thr Asp Gly Phe Arg
        675                 680                 685
Ala Asp His Gly Glu Ile Lys Lys Ala Val Ala Val Asn Gly Ile Gly
690                 695                 700
```

```
Thr Val Ile Leu Tyr Leu Ala Arg Asp Leu Thr Ser Phe Ala
705                 710                 715

<210> SEQ ID NO 35
<211> LENGTH: 718
<212> TYPE: PRT
<213> ORGANISM: Unknown
<220> FEATURE:
<223> OTHER INFORMATION: bacterial

<400> SEQUENCE: 35

Met Val Ser Ile Arg Arg Ser Phe Glu Ala Tyr Val Asp Met Asn
1               5                   10                  15

Ile Ile Thr Val Leu Ile Pro Ser Asp Gln Lys Glu Ile Met Thr Pro
                20                  25                  30

Pro Phe Gln Leu Glu Thr Glu Thr Ala Val Phe Pro Leu Ala Val Arg
            35                  40                  45

Glu Glu Tyr Arg Leu Glu Ala Thr Tyr Lys Tyr Val Cys Val Ser Asp
        50                  55                  60

His Pro Val Thr Phe Gly Lys Thr His Ala Val Arg Ala Ser Ser Gly
65                  70                  75                  80

Asp Gln Thr Asp Leu Gln Ile Gly Ala Val Ile Arg Thr Asp Ala Phe
                85                  90                  95

Asp Asp Ala Phe Tyr Tyr Asp Gly Glu Leu Gly Ala Val Tyr Thr Ala
            100                 105                 110

Asp Tyr Thr Glu Phe Lys Val Trp Ala Pro Ala Ala Val Ser Ala Ala
        115                 120                 125

Val Lys Leu Ser Pro Pro Asn Lys Ser Gly Arg Met Phe Gln Met Thr
130                 135                 140

Arg Leu Glu Lys Gly Val Tyr Ala Val Thr Val Ser Gly Asp Leu His
145                 150                 155                 160

Gly Tyr Glu Tyr Val Phe Cys Ile Cys Asn Asn Ser Val Trp Thr Glu
                165                 170                 175

Thr Val Asp Pro Tyr Ala Lys Ala Val Thr Val Asn Gly Glu Lys Gly
            180                 185                 190

Val Val Leu Arg Pro Asp Gln Met Lys Cys Ser Asp Pro Leu Lys Pro
        195                 200                 205

Phe Pro His Pro Ala Asp Thr Val Ile Tyr Glu Met His Ile Arg Asp
210                 215                 220

Phe Ser Ile His Gln Tyr Ser Gly Met Lys Asn Lys Gly Lys Tyr Leu
225                 230                 235                 240

Ala Leu Thr Glu Thr Asp Thr Gln Thr Thr Asn Gly Cys Ser Ser Gly
                245                 250                 255

Leu Thr Tyr Val Lys Glu Leu Gly Val Thr His Val Glu Leu Leu Pro
            260                 265                 270

Val Asn Asp Phe Ala Gly Val Asp Glu Lys Lys Pro Leu Asp Ala Tyr
        275                 280                 285

Asn Trp Gly Tyr Asn Pro Leu His Phe Phe Ala Pro Glu Gly Ser Tyr
290                 295                 300

Ala Ser Asn Pro His Asp Pro Gln Thr Arg Lys Thr Glu Leu Lys Gln
305                 310                 315                 320

Met Ile Lys Thr Leu His Gln His Gly Leu Arg Val Ile Leu Asp Val
                325                 330                 335

Val Phe Asn His Val Tyr Glu Arg Glu Asn Ser Pro Phe Glu Lys Thr
            340                 345                 350
```

Val Pro Gly Tyr Phe Arg His Asn Ala Phe Gly Met Pro Ser Asn
            355                 360                 365

Gly Thr Gly Val Gly Asn Asp Ile Ala Ser Glu Arg Arg Met Ala Arg
        370                 375                 380

Lys Phe Ile Ala Asp Cys Val Ile Tyr Trp Leu Gln Glu Tyr Asp Ala
385                 390                 395                 400

Asp Gly Phe Arg Phe Asp Leu Leu Gly Ile Leu Asp Ile Asp Thr Val
                405                 410                 415

Leu Phe Ile Lys Glu Lys Ala Met Ala Val Lys Pro Gly Ile Leu Leu
            420                 425                 430

Phe Gly Glu Gly Trp Asp Leu Asp Thr Pro Leu Pro His Glu Gln Lys
        435                 440                 445

Ala Ile Leu Ala Asn Ala Ser Lys Met Pro Gly Ile Gly Phe Phe Asn
    450                 455                 460

Asp Met Phe Arg Asp Ala Val Lys Gly Asn Thr Phe Gln Leu Met Ser
465                 470                 475                 480

Ala Gly Phe Ala Leu Gly Ser Gly Gly Ala Ala Glu Asn Val Met His
                485                 490                 495

Gly Ile Thr Gly Ser Ser Gly Trp Lys Ala Leu Ala Pro Val Val Pro
            500                 505                 510

Glu Pro Ser Gln Ser Ile Asn Tyr Val Glu Ser His Asp Asn His Thr
        515                 520                 525

Phe Trp Asp Lys Met Ser Leu Ala Leu Pro Gln Glu Thr Asp Ser Arg
    530                 535                 540

Lys Arg Ser Arg Gln Arg Leu Ala Ser Ala Ile Ile Leu Leu Ala Gln
545                 550                 555                 560

Gly Val Pro Phe Ile His Ser Gly Gln Glu Phe Phe Arg Thr Lys Gln
                565                 570                 575

Gly Val Glu Asn Ser Tyr Gln Ser Ser Asp Ser Ile Asn Gln Leu Asp
            580                 585                 590

Trp Asp Arg Arg Glu Met Phe Lys Glu Asp Val Asp Tyr Phe Arg Arg
        595                 600                 605

Leu Ile Ser Leu Arg Lys Ala His Pro Ala Phe Arg Leu Arg Ser Ala
    610                 615                 620

Ala Asp Ile Arg Arg His Leu Glu Cys Leu Thr Arg Asp Glu His Leu
625                 630                 635                 640

Ile Ala Tyr Arg Leu His Asn Leu Asn Gly Ile Asp Glu Trp Glu Asp
                645                 650                 655

Val Ile Val Ile His His Ala Ser Pro Ala Ala Val Glu Trp Lys Leu
            660                 665                 670

Pro Asn Asp Lys Ser Tyr Arg Leu Leu Cys Asp Thr Ser Gly Phe Gln
        675                 680                 685

Arg Asp Pro Lys Glu Ile Lys Lys Ala Val Ala Val Met Gly Ile Gly
    690                 695                 700

Thr Val Ile Leu Tyr Leu Ala Ser Asp Leu Lys Ser Phe Ala
705                 710                 715

<210> SEQ ID NO 36
<211> LENGTH: 718
<212> TYPE: PRT
<213> ORGANISM: Unknown
<220> FEATURE:
<223> OTHER INFORMATION: bacterial

<400> SEQUENCE: 36

```
Met Val Ser Ile Arg Arg Ser Phe Glu Ala Tyr Val Asp Asp Met Asn
1               5                   10                  15

Ile Ile Thr Val Leu Ile Pro Ala Glu Gln Lys Glu Ile Ile Lys Pro
            20                  25                  30

Pro Phe Arg Leu Glu Thr Glu Thr Thr Asp Phe Pro Leu Ala Val Arg
        35                  40                  45

Glu Glu Cys Arg Leu Glu Ala Thr Tyr Lys Tyr Val Cys Val Ser Asp
    50                  55                  60

Arg Pro Val Thr Phe Gly Lys Ile His Ala Val Arg Ala Ser Ser Gly
65                  70                  75                  80

Asp Lys Thr Asp Leu Gln Phe Gly Ala Val Ile Arg Met Asp Thr Phe
                85                  90                  95

Asp Asp Ser Phe Tyr Tyr Asp Gly Glu Leu Gly Ala Val Tyr Thr Ala
                100                 105                 110

Asp Tyr Thr Glu Phe Lys Val Trp Ala Pro Ala Ala Thr Ser Ala Ala
            115                 120                 125

Val Lys Leu Ser His Pro Asn Lys Arg Gly Arg Ile Phe Gln Met Ile
        130                 135                 140

Arg Met Asp Lys Gly Val Tyr Thr Val Thr Val Asn Gly Asp Leu His
145                 150                 155                 160

Gly Tyr Glu Tyr Val Phe Cys Ile Cys Asn Asn Ser Val Trp Ala Glu
                165                 170                 175

Thr Val Asp Pro Tyr Ala Lys Ala Val Thr Val Asn Gly Glu Lys Gly
            180                 185                 190

Val Val Leu Arg Pro Asp Gln Met Lys Trp Ala Asp Lys Leu Lys Pro
        195                 200                 205

Phe Ser Asn Pro Val Asp Ala Val Ile Tyr Glu Met His Ile Arg Asp
210                 215                 220

Phe Ser Ile His Glu Asn Ser Gly Met Lys Asn Lys Gly Lys Tyr Leu
225                 230                 235                 240

Ala Leu Thr Glu Thr Asp Thr Gln Thr Thr Asn Gly Cys Ser Ser Gly
                245                 250                 255

Leu Ala Tyr Ile Lys Glu Leu Gly Ile Thr His Val Glu Leu Leu Pro
            260                 265                 270

Val Asn Asp Phe Ala Gly Val Asn Glu Glu Lys Pro Leu Asp Ala Tyr
        275                 280                 285

Asn Trp Gly Tyr Asn Pro Leu His Phe Phe Ala Pro Glu Gly Ser Tyr
    290                 295                 300

Ala Ser Asn Pro His Asp Pro Gln Thr Arg Lys Thr Glu Leu Lys Gln
305                 310                 315                 320

Met Ile Lys Thr Leu His Gln His Gly Leu Arg Val Ile Leu Asp Val
                325                 330                 335

Val Phe Asn His Val Tyr Glu Arg Glu Asp Ser Pro Phe Glu Lys Thr
                340                 345                 350

Val Pro Gly Tyr Phe Phe Arg His Asp Glu Phe Gly Met Pro Ser Asn
            355                 360                 365

Gly Thr Gly Val Gly Asn Asp Ile Ala Ser Glu Arg Arg Met Ala Arg
        370                 375                 380

Lys Phe Ile Ala Asp Cys Val Ile Tyr Trp Ile Glu Glu Tyr Asp Ala
385                 390                 395                 400

Asp Gly Phe Arg Phe Asp Leu Leu Gly Ile Leu Asp Ile Asp Thr Val
                405                 410                 415
```

Leu Tyr Ile Lys Glu Lys Ala Thr Ala Val Lys Pro Gly Ile Leu Leu
            420                 425                 430

Phe Gly Glu Gly Trp Asp Leu Ala Thr Pro Leu Pro His Glu Gln Lys
        435                 440                 445

Ala Ile Leu Ala Asn Ala Thr Lys Ile Pro Gly Ile Gly Phe Phe Asn
    450                 455                 460

Asp Met Phe Arg Asp Ala Val Lys Gly Asn Thr Phe His Leu Thr Ala
465                 470                 475                 480

Ala Gly Phe Ala Leu Gly Ser Gly Glu Ala Gly Asn Val Met His
            485                 490                 495

Gly Ile Ala Gly Ser Ser Gly Trp Lys Ala Leu Ala Pro Ile Val Pro
            500                 505                 510

Glu Pro Ser Gln Ser Ile Asn Tyr Val Glu Ser His Asp Asn His Thr
        515                 520                 525

Phe Trp Asp Lys Met Gly Leu Ala Leu Ser Gln Glu Thr Asp Ser Arg
    530                 535                 540

Lys Arg Ser Arg Gln Arg Leu Ala Ala Ile Ile Leu Leu Ala Gln
545                 550                 555                 560

Gly Val Pro Phe Ile His Ser Gly Gln Glu Phe Phe Arg Thr Lys Gln
            565                 570                 575

Gly Val Glu Asn Ser Tyr Gln Ser Ser Asp Ser Ile Asn Gln Leu Asp
            580                 585                 590

Trp Asp Arg Arg Glu Thr Phe Lys Glu Asp Val Asp Tyr Ile Arg Arg
        595                 600                 605

Leu Ile Ser Leu Arg Arg Thr His Pro Ala Phe Arg Leu Asn Ser Ala
    610                 615                 620

Ala Asp Ile Gln Ser His Leu Glu Cys Val Thr Leu Lys Glu His Leu
625                 630                 635                 640

Ile Ala Tyr Arg Leu Tyr Asp Leu Asn Gly Ile Asp Glu Trp Glu Asp
            645                 650                 655

Ile Ile Val Ile His His Ala Ser Pro Asp Phe Val Glu Trp Lys Leu
            660                 665                 670

Pro Asn Asp Lys Thr Tyr Arg Leu Leu Cys Asp Thr Ser Gly Leu His
        675                 680                 685

His Asp Pro Lys Glu Ile Lys Lys Ala Val Ala Val Asn Gly Ile Gly
    690                 695                 700

Thr Val Ile Leu Tyr Leu Ala Ser Asp Leu Lys Ser Phe Ala
705                 710                 715

<210> SEQ ID NO 37
<211> LENGTH: 718
<212> TYPE: PRT
<213> ORGANISM: Unknown
<220> FEATURE:
<223> OTHER INFORMATION: bacterial

<400> SEQUENCE: 37

Met Val Ser Ile Arg Arg Ser Phe Glu Ala Tyr Val Asp Asp Met Asn
1               5                   10                  15

Ile Ile Thr Val Leu Ile Pro Ala Glu Gln Lys Glu Ile Ile Lys Pro
            20                  25                  30

Pro Phe Arg Leu Glu Thr Glu Thr Asp Phe Pro Leu Ala Val Arg
        35                  40                  45

Glu Glu Cys Arg Leu Glu Ala Thr Tyr Lys Tyr Val Cys Val Ser Asp
50                  55                  60

-continued

Arg Pro Val Thr Phe Gly Lys Ile His Ala Val Arg Ala Ser Ser Gly
65                  70                  75                  80

Asp Lys Thr Asp Leu Gln Ile Gly Ala Val Ile Arg Met Asp Thr Phe
            85                  90                  95

Asp Asp Ser Phe Tyr Tyr Asp Gly Glu Leu Gly Ala Val Tyr Thr Ala
                100                 105                 110

Asp Tyr Thr Glu Phe Lys Val Trp Ala Pro Ala Ala Thr Ser Ala Ala
            115                 120                 125

Val Lys Leu Ser His Pro Asn Lys Arg Gly Arg Ile Phe Gln Met Ile
        130                 135                 140

Arg Met Asp Lys Gly Val Tyr Thr Val Thr Val Asn Gly Asp Leu His
145                 150                 155                 160

Gly Tyr Glu Tyr Val Phe Cys Ile Cys Asn Asn Ser Val Trp Ala Glu
                165                 170                 175

Thr Val Asp Pro Tyr Ala Lys Ala Val Thr Val Asn Gly Glu Lys Gly
            180                 185                 190

Val Val Leu Arg Pro Asp Gln Met Lys Trp Ala Asp Lys Leu Lys Pro
        195                 200                 205

Phe Ser Asn Pro Val Asp Ala Val Ile Tyr Glu Met His Ile Arg Asp
210                 215                 220

Phe Ser Ile His Glu Asn Ser Gly Met Lys Asn Lys Gly Lys Tyr Leu
225                 230                 235                 240

Ala Leu Thr Glu Thr Asp Thr Gln Thr Thr Asn Gly Cys Ser Ser Gly
                245                 250                 255

Leu Ala Tyr Ile Lys Glu Leu Gly Ile Thr His Val Glu Leu Leu Pro
            260                 265                 270

Val Asn Asp Phe Ala Gly Val Asn Glu Glu Lys Pro Leu Asp Ala Tyr
        275                 280                 285

Asn Trp Gly Tyr Asn Pro Leu His Phe Phe Ala Pro Glu Gly Ser Tyr
290                 295                 300

Ala Ser Asn Pro His Asp Pro Gln Thr Arg Lys Thr Glu Leu Lys Gln
305                 310                 315                 320

Met Ile Lys Thr Leu His Gln His Gly Leu Arg Val Ile Leu Asp Val
                325                 330                 335

Val Phe Asn His Val Tyr Glu Arg Glu Asn Ser Pro Phe Glu Lys Thr
            340                 345                 350

Val Pro Gly Tyr Phe Arg His Asp Glu Phe Gly Met Pro Ser Asn
        355                 360                 365

Gly Thr Gly Val Gly Asn Asp Ile Ala Ser Glu Arg Arg Met Ala Arg
370                 375                 380

Lys Phe Ile Ala Asp Cys Val Ile Tyr Trp Ile Glu Glu Tyr Asp Ala
385                 390                 395                 400

Asp Gly Phe Arg Phe Asp Leu Leu Gly Ile Leu Asp Ile Asp Thr Val
                405                 410                 415

Leu Tyr Met Lys Glu Lys Ala Thr Ala Val Lys Pro Gly Ile Leu Leu
            420                 425                 430

Phe Gly Glu Gly Trp Asp Leu Ala Thr Pro Leu Pro His Glu Gln Lys
        435                 440                 445

Ala Thr Leu Ala Asn Val Thr Lys Met Pro Gly Ile Gly Phe Phe Asn
            450                 455                 460

Asp Met Phe Arg Asp Ala Val Lys Gly Asn Thr Phe His Leu Thr Ala
465                 470                 475                 480

Ala Gly Phe Ala Leu Gly Ser Gly Glu Ala Ala Gly Asn Val Met His

```
                   485                 490                 495
Gly Ile Ala Gly Ser Ser Gly Trp Lys Ala Leu Ala Pro Ile Val Pro
            500                 505                 510

Glu Pro Ser Gln Ser Ile Asn Tyr Val Glu Ser His Asp Asn His Thr
        515                 520                 525

Phe Trp Asp Lys Met Gly Phe Val Leu Ser Gln Glu Thr Asp Ser Arg
    530                 535                 540

Lys Arg Ser Arg Gln Arg Leu Ala Ala Ala Ile Ile Leu Leu Ala Gln
545                 550                 555                 560

Gly Val Pro Phe Ile His Ser Gly Gln Glu Phe Phe Arg Thr Lys Gln
                565                 570                 575

Gly Val Glu Asn Ser Tyr Gln Ser Ser Asp Ser Ile Asn Gln Leu Asp
            580                 585                 590

Trp Asp Arg Arg Glu Thr Phe Lys Glu Asp Val Asp Tyr Ile Arg Arg
        595                 600                 605

Leu Ile Ser Leu Arg Arg Thr His Pro Ala Phe Arg Leu Asn Ser Ala
    610                 615                 620

Ala Asp Ile Gln Ser His Leu Glu Cys Val Thr Leu Lys Glu His Leu
625                 630                 635                 640

Ile Ala Tyr Arg Leu Tyr Asp Leu Asn Gly Ile Asp Glu Trp Glu Asp
                645                 650                 655

Ile Ile Val Ile His His Ala Ser Pro Asp Phe Val Glu Trp Lys Leu
            660                 665                 670

Pro Asn Asp Lys Thr Tyr Arg Leu Leu Cys Asp Thr Ser Gly Leu His
        675                 680                 685

His Asp Pro Lys Glu Ile Lys Lys Ala Val Ala Val Asn Gly Ile Gly
    690                 695                 700

Thr Val Ile Leu Tyr Leu Ala Ser Asp Leu Lys Ser Phe Ala
705                 710                 715

<210> SEQ ID NO 38
<211> LENGTH: 718
<212> TYPE: PRT
<213> ORGANISM: Bacillus sp.

<400> SEQUENCE: 38

Met Val Ser Ile Arg Arg Ser Phe Glu Ala Tyr Val Asp Asp Met Asn
1               5                   10                  15

Ile Ile Thr Val Leu Ile Pro Ala Glu Gln Lys Glu Ile Met Thr Pro
            20                  25                  30

Pro Phe Arg Leu Glu Thr Glu Thr Thr Asp Phe Pro Leu Ala Val Arg
        35                  40                  45

Glu Glu Tyr Arg Leu Glu Asp Thr Tyr Lys Tyr Val Cys Val Ser Asp
    50                  55                  60

His Pro Val Thr Phe Gly Lys Ile His Ala Val Arg Ala Ser Ser Gly
65                  70                  75                  80

Asp Lys Thr Asp Leu Gln Ile Gly Ala Val Ile Arg Thr Asp Thr Phe
                85                  90                  95

Asp Asp Ser Phe Tyr Tyr Asp Gly Glu Leu Gly Ala Val Tyr Thr Ala
            100                 105                 110

Asn Tyr Thr Asp Phe Lys Val Trp Ala Pro Ala Ala Thr Ser Ala Ala
        115                 120                 125

Val Lys Leu Ser His Pro Asn Lys Ser Gly Arg Ile Phe Gln Met Ile
    130                 135                 140
```

```
Arg Met Glu Lys Gly Val Tyr Thr Val Ser Val Asn Gly Asp Leu His
145                 150                 155                 160

Gly Tyr Glu Tyr Val Phe Cys Ile Cys Asn Asn Ser Glu Trp Thr Glu
            165                 170                 175

Thr Val Asp Pro Tyr Ala Lys Ala Val Thr Val Asn Gly Glu Lys Gly
        180                 185                 190

Val Val Leu Arg Pro Asp Gln Met Lys Trp Ala Asp Lys Leu Lys Pro
    195                 200                 205

Phe Ser Asn Pro Val Asp Ala Val Ile Tyr Glu Met His Ile Arg Asp
    210                 215                 220

Phe Ser Ile His Glu Asn Ser Gly Met Lys Asn Lys Gly Lys Tyr Leu
225                 230                 235                 240

Ala Leu Thr Glu Thr Glu Thr Gln Thr Ile Asn Gly Cys Ser Ser Gly
            245                 250                 255

Leu Ala Tyr Ile Lys Glu Leu Gly Ile Thr His Val Glu Leu Leu Pro
            260                 265                 270

Val Asn Asp Phe Ala Gly Ile Asn Glu Glu Lys Pro Leu Asp Ala Tyr
        275                 280                 285

Asn Trp Gly Tyr Asn Pro Leu His Phe Phe Ala Pro Glu Gly Ser Tyr
        290                 295                 300

Ala Ser Asn Pro His Asp Pro Gln Thr Arg Lys Thr Glu Leu Lys Gln
305                 310                 315                 320

Met Ile Lys Thr Leu His Gln His Gly Leu Arg Val Ile Leu Asp Val
            325                 330                 335

Val Phe Asn His Val Tyr Glu Arg Glu Asn Ser Pro Phe Glu Lys Thr
        340                 345                 350

Val Pro Gly Tyr Phe Phe Arg His Asp Glu Phe Gly Met Pro Ser Asn
        355                 360                 365

Gly Thr Gly Val Gly Asn Asp Ile Ala Ser Glu Arg Arg Met Ala Arg
        370                 375                 380

Lys Phe Ile Ala Asp Cys Val Ile Tyr Trp Ile Glu Glu Tyr Asp Ala
385                 390                 395                 400

Asp Gly Phe Arg Phe Asp Leu Leu Gly Ile Leu Asp Ile Asp Thr Val
            405                 410                 415

Leu Tyr Met Lys Glu Lys Ala Thr Ala Val Lys Pro Gly Ile Leu Leu
            420                 425                 430

Phe Gly Glu Gly Trp Asp Leu Ala Thr Pro Leu Pro Gln Glu Gln Lys
        435                 440                 445

Ala Thr Leu Ala Asn Ala Thr Lys Met Pro Gly Ile Gly Phe Phe Asn
450                 455                 460

Asp Thr Phe Arg Asp Ala Val Lys Gly Asn Thr Phe His Leu Thr Ala
465                 470                 475                 480

Ala Gly Phe Ala Leu Gly Asn Gly Glu Ala Ala Glu Thr Val Met His
            485                 490                 495

Gly Ile Ala Gly Ser Ser Gly Trp Lys Ala Leu Ala Pro Ile Val Pro
        500                 505                 510

Glu Pro Ser Gln Ser Ile Asn Tyr Val Glu Ser His Asp Asn His Thr
        515                 520                 525

Phe Trp Asp Lys Met Gly Phe Val Leu Ser Gln Glu Thr Asp Ser Arg
        530                 535                 540

Lys Arg Ser Arg Gln Arg Leu Ala Ala Ala Ile Ile Leu Leu Ala Gln
545                 550                 555                 560

Gly Val Pro Phe Ile His Ser Gly Gln Glu Phe Phe Arg Thr Lys Gln
```

```
            565                 570                 575
Gly Val Glu Asn Ser Tyr Gln Ser Ser Asp Ser Ile Asn Gln Leu Asp
            580                 585                 590

Trp Asp Arg Arg Glu Thr Phe Lys Glu Asp Val Asp Tyr Ile Arg Arg
            595                 600                 605

Leu Ile Ser Leu Arg Thr Thr His Pro Ala Phe Arg Leu Asn Pro Ser
            610                 615                 620

Val Asp Ile Gln Ser His Leu Glu Cys Leu Thr Leu Arg Glu His Leu
625                 630                 635                 640

Ile Ala Tyr Arg Leu Tyr Asp Leu Asn Gly Ile Asp Gln Trp Glu Asp
                645                 650                 655

Ile Ile Val Ile His His Ala Ser Pro Asp Phe Val Glu Trp Glu Leu
                660                 665                 670

Pro Asn Asp Thr Thr Tyr Arg Leu Leu Cys Asp Thr Ser Gly Phe His
                675                 680                 685

His Asp Pro Lys Glu Ile Lys Lys Ala Val Ala Val Asn Ser Ile Gly
                690                 695                 700

Thr Val Ile Leu Tyr Leu Ala Ser Asp Leu Lys Ser Phe Ser
705                 710                 715

<210> SEQ ID NO 39
<211> LENGTH: 718
<212> TYPE: PRT
<213> ORGANISM: Bacillus licheniformis

<400> SEQUENCE: 39

Met Val Ser Ile Arg Arg Ser Phe Glu Ala Tyr Val Asp Asp Met Asn
1               5                   10                  15

Val Ile Thr Val Leu Ile Pro Ala Glu Gln Lys Asp Ile Ile Lys Pro
            20                  25                  30

Pro Phe Arg Leu Glu Thr Glu Thr Ala Val Phe Pro Leu Ala Val Arg
        35                  40                  45

Glu Glu Tyr Arg Leu Glu Ala Thr Tyr Lys Tyr Val Cys Val Ser Asp
    50                  55                  60

His Pro Val Thr Phe Gly Lys Ile His Val Val Arg Ala Ser Ser Gly
65                  70                  75                  80

Asp Lys Thr Asp Leu Gln Ile Gly Ala Val Ile Arg Thr Ala Ala Phe
                85                  90                  95

Asp Asp Ala Phe Tyr Tyr Asp Gly Glu Leu Gly Ala Val Tyr Thr Ala
            100                 105                 110

Asp Tyr Thr Glu Phe Lys Val Trp Ala Pro Ala Ala Val Ser Ala Ala
        115                 120                 125

Val Lys Leu Ser Arg Pro Asn Lys Ser Gly Leu Thr Phe Gln Met Thr
    130                 135                 140

Arg Leu Glu Lys Gly Val Tyr Ala Val Thr Val Ser Gly Asp Leu His
145                 150                 155                 160

Gly Tyr Glu Tyr Val Phe Cys Ile Cys Asn Asn Ser Gln Trp Ala Glu
                165                 170                 175

Thr Val Asp Pro Tyr Ala Lys Ala Val Thr Val Asn Gly Glu Lys Gly
            180                 185                 190

Val Val Leu Arg Pro Asp Gln Met Lys Arg Ala Asp Pro Leu Lys Pro
        195                 200                 205

Phe Ser Asn Pro Ala Asp Ala Val Ile Tyr Glu Met His Ile Arg Asp
    210                 215                 220
```

```
Phe Ser Ile His Glu Asn Ser Gly Met Lys Asn Lys Gly Lys Tyr Leu
225                 230                 235                 240

Ala Leu Thr Glu Thr Asp Thr Gln Thr Thr Lys Gly Cys Ser Ser Gly
            245                 250                 255

Leu Ala Tyr Val Lys Glu Leu Gly Val Thr His Val Glu Leu Leu Pro
        260                 265                 270

Val Asn Asp Phe Ala Gly Val Asp Glu Glu Lys Pro Leu Asp Ala Tyr
    275                 280                 285

Asn Trp Gly Tyr Asn Pro Leu His Phe Phe Ala Pro Glu Gly Ser Tyr
290                 295                 300

Ala Ser Asn Pro His Asp Pro Gln Thr Arg Lys Thr Glu Leu Lys Gln
305                 310                 315                 320

Met Ile Lys Ile Leu His Gln His Gly Leu Arg Val Ile Leu Asp Val
                325                 330                 335

Val Phe Asn His Val Tyr Glu Arg Glu Asn Ser Pro Phe Glu Lys Thr
            340                 345                 350

Val Pro Gly Tyr Tyr Phe Arg His Asp Glu Phe Gly Met Pro Ser Asn
        355                 360                 365

Gly Thr Gly Val Gly Asn Asp Ile Ala Ser Glu Arg Arg Met Ala Arg
370                 375                 380

Lys Phe Ile Ala Asp Cys Val Ile Tyr Trp Leu Glu Glu Tyr Asp Ala
385                 390                 395                 400

Asp Gly Phe Arg Phe Asp Leu Leu Gly Ile Leu Asp Ile Asp Thr Val
                405                 410                 415

Leu Tyr Ile Lys Glu Lys Ala Thr Ala Val Lys Pro Gly Ile Leu Leu
            420                 425                 430

Phe Gly Glu Gly Trp Asp Leu Ala Thr Pro Leu Pro His Glu Gln Lys
        435                 440                 445

Ala Ala Leu Ala Asn Ala Ser Lys Met Ala Gly Ile Gly Phe Phe Asn
    450                 455                 460

Asp Met Phe Arg Asp Ala Val Lys Gly Asn Thr Phe His Leu Thr Ala
465                 470                 475                 480

Ala Gly Phe Ala Leu Gly Gly Gly Glu Ala Ala Gly Thr Val Met His
                485                 490                 495

Gly Ile Ala Gly Ser Ser Gly Trp Lys Ala Leu Ala Pro Val Val Pro
            500                 505                 510

Glu Pro Ser Gln Ser Ile Asn Tyr Val Glu Ser His Asp Asn His Thr
        515                 520                 525

Phe Trp Asp Lys Met Ser Leu Ala Leu Pro His Glu Thr Asp Ser Arg
530                 535                 540

Lys Arg Ser Arg Gln Arg Leu Ala Ser Ala Ile Ile Leu Leu Ala Gln
545                 550                 555                 560

Gly Val Pro Phe Ile His Ser Gly Gln Glu Phe Phe Arg Thr Lys Gln
                565                 570                 575

Gly Val Glu Asn Ser Tyr Gln Ser Asn Ser Ile Asn Gln Leu Asp
            580                 585                 590

Trp Asp Arg Arg Glu Thr Phe Lys Glu Asp Val Asp Tyr Ile Arg Arg
        595                 600                 605

Leu Ile Ser Leu Arg Lys Ala His Pro Ala Phe Arg Leu Asn Ser Ala
610                 615                 620

Ala Asp Ile Gln Arg His Leu Glu Cys Leu Thr Leu Asn Glu His Leu
625                 630                 635                 640

Ile Ala Tyr Arg Leu His Asp Leu Gly Ala Phe Asp Lys Trp Glu Asp
```

```
                   645                 650                 655
Ile Ile Val Ile His His Ala Ser Pro Glu Ser Val Glu Trp Lys Leu
            660                 665                 670

Pro Asn Asp Lys Thr Tyr Arg Leu Leu Cys Asp Thr Ser Gly Phe Gln
            675                 680                 685

His Asp Pro Lys Glu Ile Lys Lys Ala Val Ala Val Asn Gly Ile Gly
            690                 695                 700

Thr Val Ile Leu Tyr Leu Ala Ser Asp Leu Lys Ser Phe Ala
705                 710                 715

<210> SEQ ID NO 40
<211> LENGTH: 718
<212> TYPE: PRT
<213> ORGANISM: Bacillus sp.

<400> SEQUENCE: 40

Met Val Ser Ile Arg Arg Ser Phe Glu Ala Tyr Val Asp Asp Met Asn
1               5                   10                  15

Ile Ile Thr Val Leu Ile Pro Ala Glu Gln Lys Glu Ile Ile Thr Pro
            20                  25                  30

Pro Phe Arg Leu Glu Thr Glu Thr Thr Asp Phe Pro Leu Ala Val Arg
        35                  40                  45

Glu Glu Tyr Ser Leu Glu Ala Lys Tyr Lys Tyr Ile Cys Val Pro Asp
    50                  55                  60

His Pro Val Thr Phe Gly Lys Ile His Phe Val Ser Ala Ser Asn Gly
65                  70                  75                  80

His Lys Thr Asp Leu Gln Ile Gly Ala Val Ile Arg Thr Ala Ala Phe
                85                  90                  95

Asp Asp Glu Phe Tyr Tyr Asp Gly Glu Leu Gly Ala Val Tyr Thr Ala
            100                 105                 110

Asp His Thr Val Phe Lys Val Trp Ala Pro Ala Ala Ser Ala Ala
            115                 120                 125

Val Lys Leu Ser His Pro Asn Lys Gly Gly Arg Thr Phe Gln Met Thr
    130                 135                 140

Arg Leu Glu Lys Gly Val Tyr Ala Val Thr Val Met Gly Asp Leu His
145                 150                 155                 160

Gly Tyr Glu Tyr Val Phe Cys Ile Cys Asn Asn Ser Glu Trp Ala Glu
                165                 170                 175

Thr Val Asp Pro Tyr Ala Lys Ala Val Thr Val Asn Gly Glu Lys Gly
            180                 185                 190

Val Val Leu Arg Pro Asp Gln Met Lys Trp Thr Ala Pro Leu Lys Pro
        195                 200                 205

Phe Ser Asn Pro Val Asp Ala Val Ile Tyr Glu Thr His Leu Arg Asp
    210                 215                 220

Phe Ser Ile His Glu Asn Ser Gly Met Ile Asn Lys Gly Lys Tyr Leu
225                 230                 235                 240

Ala Leu Thr Glu Thr Asp Thr Gln Thr Ala Asn Gly Ser Ser Ser Gly
                245                 250                 255

Leu Ala Tyr Ile Lys Glu Leu Gly Val Thr His Val Glu Leu Leu Pro
            260                 265                 270

Val Asn Asp Phe Ala Gly Val Asp Glu Glu Lys Pro Leu Asp Ala Tyr
        275                 280                 285

Asn Trp Gly Tyr Asn Pro Leu His Phe Phe Ala Pro Glu Gly Ser Tyr
    290                 295                 300
```

```
Ala Ser Asn Pro His Asp Pro Gln Thr Arg Lys Thr Glu Leu Lys Gln
305                 310                 315                 320

Met Ile Asn Thr Leu His Gln His Gly Leu Arg Val Ile Leu Asp Val
            325                 330                 335

Val Phe Asn His Val Tyr His Arg Glu Asn Ser Ser Phe Glu Lys Thr
            340                 345                 350

Val Pro Gly Tyr Phe Phe Arg His Asp Glu Phe Gly Met Pro Ser Asn
            355                 360                 365

Gly Thr Gly Val Gly Asn Asp Ile Ala Ser Glu Arg Arg Met Ala Arg
        370                 375                 380

Lys Phe Ile Ala Asp Cys Val Val Tyr Trp Leu Glu Glu Tyr Asn Ala
385                 390                 395                 400

Asp Gly Phe Arg Phe Asp Leu Leu Gly Ile Leu Asp Ile Asp Thr Val
                405                 410                 415

Leu Tyr Met Lys Glu Lys Ala Thr Lys Ala Lys Pro Gly Ile Leu Leu
            420                 425                 430

Phe Gly Glu Gly Trp Asp Leu Ala Thr Pro Leu Pro His Glu Gln Lys
        435                 440                 445

Ala Thr Leu Ala Asn Ala Pro Arg Met Pro Gly Ile Gly Phe Phe Asn
450                 455                 460

Asp Met Phe Arg Asp Ala Val Lys Gly Asn Thr Phe His Leu Met Ala
465                 470                 475                 480

Ala Gly Phe Ala Leu Gly Ser Gly Glu Ser Ala Gln Ala Val Met His
                485                 490                 495

Gly Ile Ala Gly Ser Ser Gly Trp Lys Ala Phe Ala Pro Ile Val Pro
            500                 505                 510

Glu Pro Ser Gln Ser Ile Asn Tyr Val Glu Ser His Asp Asn His Thr
        515                 520                 525

Phe Trp Asp Lys Met Ser Phe Ala Leu Pro Gln Glu Asn Asp Ser Arg
530                 535                 540

Lys Arg Ser Arg Gln Arg Leu Ala Ala Ile Ile Leu Leu Ala Gln
545                 550                 555                 560

Gly Val Pro Phe Ile His Ser Gly Gln Glu Phe Phe Arg Thr Lys Gln
                565                 570                 575

Gly Val Glu Asn Ser Tyr Gln Ser Ser Asp Ser Ile Asn Glu Leu Asp
            580                 585                 590

Trp Asp Arg Arg Glu Thr Phe Lys Glu Asp Val Asp Tyr Ile Arg Arg
        595                 600                 605

Leu Ile Ser Leu Arg Lys Ala His Pro Ala Phe Arg Leu Arg Ser Ala
610                 615                 620

Ala Asp Ile Arg Arg His Leu Glu Cys Leu Thr Leu Lys Glu His Phe
625                 630                 635                 640

Ile Ala Tyr Arg Leu Tyr Asp Leu Asp Lys Val Asp Glu Trp Lys Asp
                645                 650                 655

Ile Ile Val Ile His His Ala Ser Pro Asn Ser Val Glu Trp Arg Leu
            660                 665                 670

Pro Asn Asp Lys Pro Tyr Arg Leu Leu Cys Asp Pro Ser Gly Phe Gln
        675                 680                 685

Gln Asp Pro Pro Glu Ile Lys Lys Thr Val Ala Val Asn Gly Ile Gly
690                 695                 700

Thr Val Ile Leu Tyr Leu Ala Ser Asp Leu Lys Ser Phe Ala
705                 710                 715
```

<210> SEQ ID NO 41
<211> LENGTH: 718
<212> TYPE: PRT
<213> ORGANISM: Bacillus sp.

<400> SEQUENCE: 41

Met Val Ser Ile Arg Arg Ser Phe Glu Ala Tyr Val Asp Asp Met Asn
1               5                   10                  15

Ile Ile Thr Val Leu Ile Pro Ala Glu Gln Lys Glu Ile Met Thr Pro
            20                  25                  30

Pro Phe Arg Leu Glu Thr Glu Thr Thr Asp Phe Pro Leu Ala Val Arg
        35                  40                  45

Glu Glu Tyr Ser Leu Glu Ala Lys Tyr Lys Tyr Ile Cys Val Ser Asp
    50                  55                  60

His Pro Val Thr Phe Gly Lys Ile His Phe Val Ser Ala Ser Ser Gly
65                  70                  75                  80

His Lys Thr Asp Leu Gln Ile Gly Ala Val Ile Arg Thr Ala Ala Phe
                85                  90                  95

Asp Asp Glu Phe Tyr Tyr Asp Gly Glu Leu Gly Ala Val Tyr Thr Ala
            100                 105                 110

Asp His Thr Val Phe Lys Val Trp Ala Pro Ala Ala Thr Ser Ala Ala
        115                 120                 125

Val Lys Leu Ser His Pro Asn Lys Gly Gly Arg Thr Phe Gln Met Thr
    130                 135                 140

Arg Leu Glu Lys Gly Val Tyr Ala Val Thr Val Met Gly Asp Leu His
145                 150                 155                 160

Gly Tyr Glu Tyr Val Phe Cys Ile Cys Asn Asn Ser Glu Trp Ala Glu
                165                 170                 175

Thr Val Asp Pro Tyr Ala Lys Ala Val Thr Val Asn Gly Glu Lys Gly
            180                 185                 190

Val Val Leu Arg Pro Asp Gln Met Lys Trp Thr Ala Pro Leu Lys Pro
        195                 200                 205

Phe Ser Asn Pro Val Asp Ala Val Ile Tyr Glu Thr His Leu Arg Asp
    210                 215                 220

Phe Ser Ile His Lys Asn Ser Gly Met Ile Asn Lys Gly Lys Tyr Leu
225                 230                 235                 240

Ala Leu Thr Glu Thr Asp Thr Gln Thr Ala Asn Gly Ser Ser Ser Gly
                245                 250                 255

Leu Ala Tyr Ile Lys Glu Leu Gly Val Thr His Val Glu Leu Leu Pro
            260                 265                 270

Val Asn Asp Phe Ala Gly Val Asp Glu Glu Lys Pro Leu Asp Ala Tyr
        275                 280                 285

Asn Trp Gly Tyr Asn Pro Leu His Phe Phe Ala Pro Glu Gly Ser Tyr
    290                 295                 300

Ala Ser Asn Pro His Asp Pro Gln Thr Arg Lys Thr Glu Leu Lys Gln
305                 310                 315                 320

Met Ile Asn Thr Leu His Gln His Gly Leu Arg Val Ile Leu Asp Val
                325                 330                 335

Val Phe Asn His Val Tyr His Arg Glu Asn Ser Pro Phe Glu Lys Thr
            340                 345                 350

Val Pro Gly Tyr Phe Arg His Asp Glu Phe Gly Met Pro Ser Asn
        355                 360                 365

Gly Thr Gly Val Gly Asn Asp Ile Ala Ser Glu Arg Arg Met Ala Arg
    370                 375                 380

```
Lys Phe Ile Ala Asp Cys Val Val Tyr Trp Leu Glu Glu Tyr Asn Ala
385                 390                 395                 400

Asp Gly Phe Arg Phe Asp Leu Leu Gly Ile Leu Asp Ile Asp Thr Val
            405                 410                 415

Leu Tyr Met Lys Glu Lys Ala Ile Lys Ala Lys Thr Gly Ile Leu Leu
        420                 425                 430

Phe Gly Glu Gly Trp Asp Leu Ala Thr Pro Leu Pro His Glu Gln Lys
    435                 440                 445

Ala Thr Leu Ala Asn Ala Pro Arg Met Pro Gly Ile Gly Phe Phe Asn
450                 455                 460

Asp Met Phe Arg Asp Ala Val Lys Gly Asn Thr Phe His Leu Met Ala
465                 470                 475                 480

Ala Gly Phe Ala Leu Gly Ser Gly Glu Ser Ala Gln Ala Val Met His
                485                 490                 495

Gly Ile Ala Gly Ser Ser Gly Trp Lys Ala Phe Ala Pro Ile Val Pro
            500                 505                 510

Glu Pro Ser Gln Ser Ile Asn Tyr Val Glu Ser His Asp Asn His Thr
        515                 520                 525

Phe Trp Asp Lys Met Ser Phe Ala Leu Pro Gln Glu Asn Asp Ser Arg
    530                 535                 540

Lys Arg Ser Arg Gln Arg Leu Ala Ala Ala Ile Ile Leu Leu Ala Gln
545                 550                 555                 560

Gly Val Pro Phe Ile His Ser Gly Gln Glu Phe Phe Arg Thr Lys Gln
                565                 570                 575

Gly Val Glu Asn Ser Tyr Gln Ser Ser Asp Ser Ile Asn Glu Leu Asp
            580                 585                 590

Trp Gly Arg Arg Glu Thr Phe Lys Glu Asp Val Asp Tyr Ile Arg Arg
        595                 600                 605

Leu Ile Ser Leu Arg Lys Ala His Pro Ala Phe Arg Leu Arg Ser Ala
    610                 615                 620

Ala Asp Ile Arg Arg His Leu Glu Cys Leu Thr Leu Lys Glu His Phe
625                 630                 635                 640

Ile Ala Tyr Arg Leu Tyr Asp Leu Asp Glu Val Asp Glu Trp Lys Asp
                645                 650                 655

Ile Ile Val Ile His His Ala Ser Ala Asn Ser Val Glu Trp Arg Leu
            660                 665                 670

Pro Asn Asp Lys Pro Tyr Arg Leu Leu Cys Asp Pro Ser Gly Phe Gln
        675                 680                 685

Gln Asp Pro Ala Glu Ile Lys Lys Thr Val Ala Val Asn Gly Ile Gly
    690                 695                 700

Thr Val Ile Leu Tyr Leu Ala Ser Asp Leu Lys Ser Phe Ala
705                 710                 715

<210> SEQ ID NO 42
<211> LENGTH: 718
<212> TYPE: PRT
<213> ORGANISM: Bacillus sp.

<400> SEQUENCE: 42

Met Val Ser Ile Arg Arg Ser Phe Glu Ala Tyr Val Asp Asp Met Asn
1               5                   10                  15

Ile Ile Thr Val Leu Ile Pro Ala Glu Gln Lys Glu Ile Met Thr Pro
            20                  25                  30

Pro Phe Arg Leu Glu Thr Glu Thr Gly Phe Pro Leu Ala Val Arg
        35                  40                  45
```

```
Glu Glu Tyr Phe Leu Glu Ala Lys Tyr Lys Tyr Ile Cys Val Ser Asp
    50                  55                  60

Tyr Pro Val Thr Phe Gly Lys Ile His Cys Val Ser Ala Ser Ser Gly
65                  70                  75                  80

His Lys Thr Asp Leu Gln Ile Gly Ala Val Ile Arg Thr Ala Ala Phe
                85                  90                  95

Asp Asp Glu Phe Tyr Tyr Asp Gly Leu Gly Ala Val Tyr Thr Ala
                100                 105                 110

Asp His Thr Val Phe Lys Val Trp Ala Pro Ala Ala Thr Ser Ala Ala
            115                 120                 125

Val Lys Leu Ser His Pro Asn Lys Ser Gly Arg Thr Phe Gln Met Thr
    130                 135                 140

Arg Leu Glu Lys Gly Val Tyr Ala Val Thr Val Met Gly Asp Leu His
145                 150                 155                 160

Gly Tyr Glu Tyr Val Phe Cys Ile Cys Asn Asn Ser Glu Trp Met Glu
                165                 170                 175

Thr Val Asp Pro Tyr Ala Lys Ala Val Thr Val Asn Gly Glu Lys Gly
            180                 185                 190

Val Val Leu Arg Pro Asp Gln Met Asn Trp Thr Ala Arg Leu Lys Pro
        195                 200                 205

Phe Ser Asn Pro Val Asp Ala Val Ile Tyr Glu Thr His Leu Arg Asp
    210                 215                 220

Phe Ser Ile His Glu Asn Ser Gly Met Ile Asn Lys Gly Lys Tyr Leu
225                 230                 235                 240

Ala Leu Thr Glu Thr Asp Thr Gln Thr Ala Asn Gly Ser Ser Ser Gly
                245                 250                 255

Leu Ala Tyr Ile Lys Glu Leu Gly Val Thr His Val Glu Leu Leu Pro
            260                 265                 270

Val Asn Asp Phe Ala Gly Val Asp Glu Glu Lys Pro Leu Asp Ala Tyr
        275                 280                 285

Asn Trp Gly Tyr Asn Pro Leu His Phe Phe Ala Pro Glu Gly Ser Phe
    290                 295                 300

Ser Ser Asn Pro His Asp Pro Gln Thr Arg Lys Thr Glu Leu Lys Gln
305                 310                 315                 320

Met Ile Asn Thr Leu His Gln His Gly Leu Arg Val Ile Leu Asp Val
                325                 330                 335

Val Phe Asn His Val Tyr Asn Arg Glu Asn Ser Pro Phe Glu Lys Thr
            340                 345                 350

Val Pro Gly Tyr Phe Phe Arg His Asp Glu Phe Gly Met Pro Ser Asn
        355                 360                 365

Gly Thr Gly Val Gly Asn Asp Ile Ala Ser Glu Arg Arg Met Ala Arg
    370                 375                 380

Lys Phe Ile Ala Asp Cys Val Val Tyr Trp Leu Glu Glu Tyr Asn Ala
385                 390                 395                 400

Asp Gly Phe Arg Phe Asp Leu Leu Gly Ile Leu Asp Ile Asp Thr Val
                405                 410                 415

Leu Tyr Met Lys Glu Lys Ala Ile Ala Ala Lys Pro Gly Ile Leu Leu
            420                 425                 430

Phe Gly Glu Gly Trp Asp Leu Ala Thr Pro Leu Pro His Glu Gln Lys
        435                 440                 445

Ala Thr Leu Ala Asn Ala Pro Arg Met Pro Gly Ile Gly Phe Phe Asn
    450                 455                 460
```

Asp Val Phe Arg Asp Ala Val Lys Gly Asn Thr Phe His Leu Met Ala
465                 470                 475                 480

Ala Gly Phe Ala Leu Gly Ser Gly Glu Ser Ala Gln Ala Val Met His
            485                 490                 495

Gly Ile Ala Gly Ser Ser Gly Trp Lys Ala Leu Ala Pro Val Val Pro
        500                 505                 510

Glu Pro Ser Gln Ser Ile Asn Tyr Val Glu Ser His Asp Asn His Thr
    515                 520                 525

Phe Trp Asp Lys Met Ser Phe Ala Leu Pro Gln Glu Asn Asp Ser Arg
530                 535                 540

Lys Arg Ser Arg Gln Arg Leu Ala Ala Ala Ile Ile Leu Leu Ala Gln
545                 550                 555                 560

Gly Val Pro Phe Ile His Ser Gly Gln Glu Phe Phe Arg Thr Lys Gln
                565                 570                 575

Gly Val Glu Asn Ser Tyr Gln Ser Ser Asp Ser Ile Asn Gln Leu Asp
            580                 585                 590

Trp Asp Arg Arg Glu Thr Phe Lys Glu Asp Val Asp Tyr Ile Arg Arg
        595                 600                 605

Leu Ile Ser Leu Arg Lys Ala His Pro Ala Phe Arg Leu Arg Ser Ala
    610                 615                 620

Ala Asp Ile Gln Arg His Ile Glu Cys Leu Thr Leu Lys Glu His Phe
625                 630                 635                 640

Ile Ala Tyr Arg Leu Tyr Asp Leu Asp Glu Val Asp Glu Trp Lys Asp
                645                 650                 655

Ile Ile Val Ile His His Ala Ser Pro Asp Ala Val Glu Trp Arg Leu
            660                 665                 670

Pro Asn Asp Lys Pro Tyr Arg Leu Leu Cys Asp Pro Ser Gly Phe Gln
        675                 680                 685

Gln Asp Pro Ala Glu Ile Lys Lys Thr Val Ala Val Asn Gly Ile Gly
    690                 695                 700

Thr Val Ile Leu Tyr Leu Ala Ser Asp Leu Lys Ser Phe Ala
705                 710                 715

<210> SEQ ID NO 43
<211> LENGTH: 718
<212> TYPE: PRT
<213> ORGANISM: Bacillus sp.

<400> SEQUENCE: 43

Met Val Ser Ile Arg Arg Ser Phe Glu Ala Tyr Val Asp Asp Met Asn
1               5                   10                  15

Ile Ile Thr Val Leu Ile Pro Ala Glu Gln Lys Glu Ile Met Thr Pro
            20                  25                  30

Pro Phe Arg Leu Glu Thr Glu Thr Asp Phe Pro Leu Ala Val Arg
        35                  40                  45

Glu Glu Tyr Ser Leu Glu Ala Lys Tyr Lys Tyr Ile Cys Val Ser Asp
    50                  55                  60

His Pro Val Thr Phe Gly Lys Ile His Phe Val Ser Ala Ser Ser Gly
65                  70                  75                  80

His Lys Thr Asp Leu Gln Ile Gly Ala Val Ile Arg Thr Ala Ala Phe
                85                  90                  95

Asp Asp Glu Phe Tyr Tyr Asp Gly Glu Leu Gly Ala Val Tyr Thr Ala
            100                 105                 110

Asp His Thr Val Phe Lys Val Trp Ala Pro Ala Ala Thr Ser Ala Ala
        115                 120                 125

```
Val Lys Leu Ser His Pro Asn Lys Gly Gly Arg Thr Phe Gln Met Thr
    130                 135                 140

Arg Leu Glu Lys Gly Val Tyr Ala Val Thr Val Met Gly Asp Leu His
145                 150                 155                 160

Gly Tyr Glu Tyr Val Phe Cys Ile Cys Asn Asn Ser Glu Trp Ala Glu
                165                 170                 175

Thr Val Asp Pro Tyr Ala Lys Ala Val Thr Val Asn Gly Glu Lys Gly
                180                 185                 190

Val Val Leu Arg Pro Asp Gln Met Lys Trp Thr Ala Pro Leu Lys Pro
            195                 200                 205

Phe Ser Asn Pro Val Asp Ala Val Ile Tyr Glu Thr His Leu Arg Asp
210                 215                 220

Phe Ser Ile His Glu Asn Ser Gly Met Ile Asn Lys Gly Lys Tyr Leu
225                 230                 235                 240

Ala Leu Thr Glu Thr Asp Thr Gln Thr Ala Ile Gly Ser Ser Ser Gly
                245                 250                 255

Leu Ala Tyr Ile Lys Glu Leu Gly Val Thr His Val Glu Leu Leu Pro
                260                 265                 270

Val Asn Asp Phe Ala Gly Val Asp Glu Glu Lys Pro Leu Asp Ala Tyr
            275                 280                 285

Asn Trp Gly Tyr Asn Pro Leu His Phe Phe Ala Pro Glu Gly Ser Tyr
290                 295                 300

Ala Ser Asn Pro His Asp Pro Gln Thr Arg Lys Thr Glu Leu Lys Gln
305                 310                 315                 320

Met Ile Asn Thr Leu His Gln His Gly Leu Arg Val Ile Leu Asp Val
                325                 330                 335

Val Phe Asn His Val Tyr His Arg Glu Asn Ser Pro Phe Glu Lys Thr
            340                 345                 350

Val Pro Gly Tyr Phe Phe Arg His Asp Glu Phe Gly Met Pro Ser Asn
            355                 360                 365

Gly Thr Gly Val Gly Asn Asp Ile Ala Ser Glu Arg Arg Met Ala Arg
        370                 375                 380

Lys Phe Ile Ala Asp Cys Val Val Tyr Trp Leu Glu Glu Tyr Asn Ala
385                 390                 395                 400

Asp Gly Phe Arg Phe Asp Leu Leu Gly Ile Leu Asp Ile Asp Thr Val
                405                 410                 415

Leu Tyr Met Lys Glu Lys Ala Ile Lys Ala Lys Pro Gly Ile Leu Leu
            420                 425                 430

Phe Gly Glu Gly Trp Asp Leu Ala Thr Pro Leu Pro His Glu Gln Lys
            435                 440                 445

Ala Ala Leu Ala Asn Ala Pro Arg Met Pro Gly Ile Gly Phe Phe Asn
450                 455                 460

Asp Met Phe Arg Asp Ala Val Lys Gly Asn Thr Phe His Leu Met Ala
465                 470                 475                 480

Ala Gly Phe Ala Leu Gly Ser Gly Glu Ser Thr Gln Ala Val Met His
                485                 490                 495

Gly Ile Ala Gly Ser Ser Gly Trp Lys Ala Leu Ala Pro Ile Val Pro
            500                 505                 510

Glu Pro Ser Gln Ser Ile Asn Tyr Val Glu Ser His Asp Asn His Thr
            515                 520                 525

Phe Trp Asp Lys Met Ser Phe Ala Leu Pro Gln Glu Asn Asp Ser Arg
530                 535                 540
```

```
Lys Arg Ser Arg Gln Arg Leu Ala Ala Ala Ile Ile Leu Leu Ala Gln
545                 550                 555                 560

Gly Val Pro Phe Ile His Ser Gly Gln Glu Phe Phe Arg Thr Lys Gln
            565                 570                 575

Gly Val Glu Asn Ser Tyr Gln Ser Ser Asp Ser Ile Asn Glu Leu Asp
                580                 585                 590

Trp Asp Arg Arg Glu Thr Phe Lys Glu Asp Val Asp Tyr Ile Arg Arg
            595                 600                 605

Leu Ile Ser Leu Arg Lys Ala His Pro Ala Phe Arg Leu Arg Ser Ala
        610                 615                 620

Ala Asp Ile Arg Arg His Leu Glu Cys Leu Thr Leu Lys Glu His Phe
625                 630                 635                 640

Ile Ala Tyr Arg Leu Tyr Asp Leu Asp Lys Val Asp Glu Trp Lys Asp
            645                 650                 655

Ile Ile Val Ile His His Ala Ser Pro Asp Phe Val Glu Trp Arg Leu
                660                 665                 670

Pro Asn Asp Lys Pro Tyr Arg Leu Leu Cys Asp Pro Ser Gly Phe Gln
            675                 680                 685

Gln Asp Pro Ala Glu Ile Lys Lys Thr Val Ala Val Asn Gly Ile Gly
690                 695                 700

Thr Val Ile Leu Tyr Leu Ala Ser Asp Leu Lys Ser Phe Ala
705                 710                 715

<210> SEQ ID NO 44
<211> LENGTH: 718
<212> TYPE: PRT
<213> ORGANISM: Bacillus sp.

<400> SEQUENCE: 44

Met Val Ser Ile Arg Arg Ser Phe Glu Ala Tyr Val Asp Asp Met Asn
1               5                   10                  15

Ile Ile Thr Val Leu Ile Pro Ala Glu Gln Lys Glu Ile Met Thr Pro
            20                  25                  30

Pro Phe Arg Leu Glu Thr Glu Thr Thr Asp Phe Pro Leu Ala Val Arg
        35                  40                  45

Glu Glu Tyr Ser Leu Glu Ala Lys Tyr Lys Tyr Ile Cys Val Ser Asp
50                  55                  60

His Pro Val Thr Phe Gly Lys Ile His Phe Val Ser Ala Ser Ser Gly
65                  70                  75                  80

His Lys Thr Asp Leu Gln Ile Gly Ala Val Ile Arg Thr Ala Ala Phe
            85                  90                  95

Asp Asp Glu Phe Tyr Tyr Asp Gly Glu Leu Gly Ala Val Tyr Thr Ala
        100                 105                 110

Asp His Thr Val Phe Lys Val Trp Ala Pro Ala Ala Thr Ser Ala Ala
    115                 120                 125

Val Lys Leu Ser His Pro Asn Lys Gly Gly Arg Thr Phe Gln Met Thr
130                 135                 140

Arg Leu Glu Lys Gly Val Tyr Ala Val Thr Val Met Gly Asp Leu His
145                 150                 155                 160

Gly Tyr Glu Tyr Val Phe Cys Ile Cys Asn Asn Ser Glu Trp Ala Glu
            165                 170                 175

Thr Val Asp Pro Tyr Ala Lys Ala Val Thr Asn Gly Glu Lys Gly
        180                 185                 190

Val Val Leu Arg Pro Asp Gln Met Lys Trp Thr Ala Pro Leu Lys Pro
    195                 200                 205
```

```
Phe Ser Asn Pro Val Asp Ala Ile Tyr Glu Thr His Leu Arg Asp
    210                 215                 220
Phe Ser Ile His Glu Asn Ser Gly Met Ile Asn Lys Gly Lys Tyr Leu
225                 230                 235                 240
Ala Leu Thr Glu Thr Asp Thr Gln Thr Ala Ile Gly Ser Ser Ser Gly
                245                 250                 255
Leu Ala Tyr Ile Lys Glu Leu Gly Val Thr His Val Glu Leu Leu Pro
                260                 265                 270
Val Asn Asp Phe Ala Gly Val Asp Glu Glu Lys Pro Leu Asp Ala Tyr
            275                 280                 285
Asn Trp Gly Tyr Asn Pro Leu His Phe Phe Ala Pro Glu Gly Ser Tyr
290                 295                 300
Ala Ser Asn Pro His Asp Pro Gln Thr Arg Lys Thr Glu Leu Lys Gln
305                 310                 315                 320
Met Ile Asn Thr Leu His Gln His Gly Leu Arg Val Ile Leu Asp Val
                325                 330                 335
Val Phe Asn His Val Tyr His Arg Glu Asn Ser Pro Phe Glu Lys Thr
            340                 345                 350
Val Pro Gly Tyr Phe Phe Arg His Asp Glu Phe Gly Met Pro Ser Asn
            355                 360                 365
Gly Thr Gly Val Gly Asn Asp Ile Ala Ser Glu Arg Arg Met Ala Arg
370                 375                 380
Lys Phe Ile Ala Asp Cys Val Val Tyr Trp Leu Glu Glu Tyr Asn Ala
385                 390                 395                 400
Asp Gly Phe Arg Phe Asp Leu Leu Gly Ile Leu Asp Ile Asp Thr Val
                405                 410                 415
Leu Tyr Met Lys Glu Lys Ala Ile Lys Ala Lys Pro Gly Ile Leu Leu
            420                 425                 430
Phe Gly Glu Gly Trp Asp Leu Ala Thr Pro Leu Pro His Glu Gln Lys
            435                 440                 445
Ala Ala Leu Ala Asn Ala Pro Arg Met Pro Gly Ile Gly Phe Phe Asn
        450                 455                 460
Asp Met Phe Arg Asp Ala Val Lys Gly Asn Thr Phe His Leu Met Ala
465                 470                 475                 480
Ala Gly Phe Ala Leu Gly Ser Gly Glu Ser Ala Gln Ala Val Met His
                485                 490                 495
Gly Ile Ala Gly Ser Ser Gly Trp Lys Ala Leu Ala Pro Ile Val Pro
                500                 505                 510
Glu Pro Ser Gln Ser Ile Asn Tyr Val Glu Ser His Asp Asn His Thr
            515                 520                 525
Phe Trp Asp Lys Met Ser Phe Ala Leu Pro Gln Glu Asn Asp Ser Arg
            530                 535                 540
Lys Arg Ser Arg Gln Arg Leu Ala Ala Ala Ile Ile Leu Leu Ala Gln
545                 550                 555                 560
Gly Val Pro Phe Ile His Ser Gly Gln Glu Phe Phe Arg Thr Lys Gln
                565                 570                 575
Gly Val Glu Asn Ser Tyr Gln Ser Ser Asp Ser Ile Asn Glu Leu Asp
            580                 585                 590
Trp Asp Arg Arg Glu Thr Phe Lys Glu Asp Val Asp Tyr Ile Arg Arg
            595                 600                 605
Leu Ile Ser Leu Arg Lys Ala His Pro Ala Phe Arg Leu Arg Ser Ala
        610                 615                 620
```

-continued

```
Ala Asp Ile Arg Arg His Leu Glu Cys Leu Thr Leu Lys Glu His Phe
625                 630                 635                 640

Ile Ala Tyr Arg Leu Tyr Asp Leu Asp Lys Val Asp Glu Trp Lys Asp
            645                 650                 655

Ile Ile Val Ile His His Ala Ser Pro Asp Ser Val Glu Trp Arg Leu
        660                 665                 670

Pro Asn Asp Lys Pro Tyr Arg Leu Leu Cys Asp Pro Ser Gly Phe Gln
    675                 680                 685

Gln Asp Pro Ala Glu Ile Lys Lys Thr Val Ala Val Asn Gly Ile Gly
690                 695                 700

Thr Val Ile Leu Tyr Leu Ala Ser Asp Leu Lys Ser Phe Ala
705                 710                 715

<210> SEQ ID NO 45
<211> LENGTH: 718
<212> TYPE: PRT
<213> ORGANISM: Bacillus subtilis

<400> SEQUENCE: 45

Met Val Ser Ile Arg Arg Ser Phe Glu Ala Tyr Val Asp Asp Met Asn
1               5                   10                  15

Ile Ile Thr Val Leu Ile Pro Ala Glu Gln Lys Glu Ile Met Thr Pro
            20                  25                  30

Pro Phe Arg Leu Glu Thr Glu Thr Ile Gly Phe Pro Leu Ala Val Arg
        35                  40                  45

Glu Glu Tyr Ser Leu Glu Ala Lys Tyr Lys Tyr Ile Cys Val Ser Asp
    50                  55                  60

His Pro Val Thr Phe Gly Lys Ile His Phe Val Ser Ala Ser Ser Gly
65                  70                  75                  80

His Lys Thr Asp Leu Gln Ile Gly Ala Val Ile Arg Thr Ala Ala Phe
                85                  90                  95

Asp Asp Glu Phe Tyr Tyr Asp Gly Glu Leu Gly Ala Val Tyr Thr Ala
            100                 105                 110

Asp His Thr Val Phe Lys Val Trp Ala Pro Ala Ala Thr Ser Ala Ala
        115                 120                 125

Val Lys Leu Ser His Pro Asn Lys Gly Gly Arg Thr Phe Gln Met Thr
130                 135                 140

Arg Leu Glu Lys Gly Val Tyr Ala Val Thr Val Met Gly Asp Leu His
145                 150                 155                 160

Gly Tyr Glu Tyr Val Phe Cys Ile Cys Asn Asn Ser Glu Trp Ala Glu
                165                 170                 175

Thr Val Asp Pro Tyr Ala Lys Ala Val Thr Val Asn Gly Glu Lys Gly
            180                 185                 190

Val Val Leu Arg Pro Asp Gln Met Lys Trp Thr Ala Pro Leu Lys Pro
        195                 200                 205

Phe Ser His Pro Val Asp Ala Val Ile Tyr Glu Thr His Leu Arg Asp
    210                 215                 220

Phe Ser Ile His Glu Asn Ser Gly Met Ile Asn Lys Gly Lys Tyr Leu
225                 230                 235                 240

Ala Leu Thr Glu Thr Asp Thr Gln Thr Ala Asn Gly Ser Ser Ser Gly
                245                 250                 255

Leu Ala Tyr Ile Lys Glu Leu Gly Val Thr His Val Glu Leu Leu Pro
            260                 265                 270

Val Asn Asp Phe Ala Gly Val Asp Glu Glu Lys Pro Leu Asp Ala Tyr
        275                 280                 285
```

```
Asn Trp Gly Tyr Asn Pro Leu His Phe Phe Ala Pro Glu Gly Ser Tyr
    290                 295                 300
Ala Ser Asn Pro His Asp Pro Gln Thr Arg Lys Thr Glu Leu Lys Gln
305                 310                 315                 320
Met Ile Asn Thr Leu His Gln His Gly Leu Arg Val Ile Leu Asp Val
                325                 330                 335
Val Phe Asn His Val Tyr Lys Arg Glu Asn Ser Pro Phe Glu Lys Thr
            340                 345                 350
Val Pro Gly Tyr Phe Phe Arg His Asp Glu Cys Gly Met Pro Ser Asn
        355                 360                 365
Gly Thr Gly Val Gly Asn Asp Ile Ala Ser Glu Arg Arg Met Ala Arg
    370                 375                 380
Lys Phe Ile Ala Asp Cys Val Val Tyr Trp Leu Glu Glu Tyr Asn Val
385                 390                 395                 400
Asp Gly Phe Arg Phe Asp Leu Leu Gly Ile Leu Asp Ile Asp Thr Val
                405                 410                 415
Leu Tyr Met Lys Glu Lys Ala Thr Lys Ala Lys Pro Gly Ile Leu Leu
            420                 425                 430
Phe Gly Glu Gly Trp Asp Leu Ala Thr Pro Leu Pro His Glu Gln Lys
        435                 440                 445
Ala Ala Leu Ala Asn Ala Pro Arg Met Pro Gly Ile Gly Phe Phe Asn
    450                 455                 460
Asp Met Phe Arg Asp Ala Val Lys Gly Asn Thr Phe His Leu Lys Ala
465                 470                 475                 480
Ala Gly Phe Ala Leu Gly Ser Gly Glu Ser Ala Gln Ala Val Met His
                485                 490                 495
Gly Ile Ala Gly Ser Ser Gly Trp Lys Ala Leu Ala Pro Ile Val Pro
            500                 505                 510
Glu Pro Ser Gln Ser Ile Asn Tyr Val Glu Ser His Asp Asn His Thr
        515                 520                 525
Phe Trp Asp Lys Met Ser Phe Ala Leu Pro Gln Glu Asn Asp Ser Arg
    530                 535                 540
Lys Arg Ser Arg Gln Arg Leu Ala Ala Ala Ile Ile Leu Leu Ala Gln
545                 550                 555                 560
Gly Val Pro Phe Ile His Ser Gly Gln Glu Phe Phe Arg Thr Lys Gln
                565                 570                 575
Gly Val Glu Asn Ser Tyr Gln Ser Ser Asp Ser Ile Asn Gln Leu Asp
            580                 585                 590
Trp Asp Arg Arg Glu Thr Phe Lys Glu Asp Val His Tyr Ile Arg Arg
        595                 600                 605
Leu Ile Ser Leu Arg Lys Ala His Pro Ala Phe Arg Leu Arg Ser Ala
    610                 615                 620
Ala Asp Ile Gln Arg His Leu Glu Cys Leu Thr Leu Lys Glu His Leu
625                 630                 635                 640
Ile Ala Tyr Arg Leu Tyr Asp Leu Asp Glu Val Asp Glu Trp Lys Asp
                645                 650                 655
Ile Ile Val Ile His His Ala Ser Pro Asp Ser Val Glu Trp Arg Leu
            660                 665                 670
Pro Asn Asp Ile Pro Tyr Arg Leu Leu Cys Asp Pro Ser Gly Phe Gln
        675                 680                 685
Glu Asp Pro Ala Glu Ile Lys Lys Thr Val Ala Val Asn Gly Ile Gly
    690                 695                 700
```

```
Thr Val Ile Leu Tyr Leu Ala Ser Asp Leu Lys Ser Phe Ala
705                 710                 715
```

```
<210> SEQ ID NO 46
<211> LENGTH: 718
<212> TYPE: PRT
<213> ORGANISM: Bacillus sp.

<400> SEQUENCE: 46
```

```
Met Val Ser Ile Arg Arg Ser Phe Glu Ala Tyr Val Asp Asp Met Asn
1               5                   10                  15

Ile Ile Thr Val Leu Ile Pro Ala Glu Gln Lys Glu Ile Met Thr Pro
                20                  25                  30

Pro Phe Arg Leu Glu Thr Glu Thr Thr Asp Phe Pro Leu Ala Val Arg
            35                  40                  45

Glu Glu Tyr Ser Leu Glu Ala Lys Tyr Lys Tyr Val Cys Val Ser Asp
50                  55                  60

His Pro Val Thr Phe Gly Lys Ile His Cys Val Arg Ala Ser Ser Gly
65                  70                  75                  80

His Lys Thr Asp Leu Gln Ile Gly Ala Val Ile Arg Thr Ser Ala Phe
                85                  90                  95

Asp Asp Glu Phe Tyr Tyr Asp Gly Glu Leu Gly Ala Val Tyr Thr Ala
            100                 105                 110

Asp His Thr Val Phe Lys Val Trp Ala Pro Ala Ala Thr Ser Ala Ala
        115                 120                 125

Val Lys Leu Ser His Pro Asn Lys Ser Gly Cys Thr Phe Gln Met Thr
130                 135                 140

Arg Leu Glu Lys Gly Val Tyr Ala Val Thr Val Thr Gly Asp Leu His
145                 150                 155                 160

Gly Tyr Glu Tyr Leu Phe Cys Ile Cys Asn Asn Ser Glu Trp Met Glu
                165                 170                 175

Thr Val Asp Pro Tyr Ala Lys Ala Val Thr Val Asn Gly Glu Leu Gly
            180                 185                 190

Val Val Leu Arg Pro Asp Gln Met Lys Trp Thr Ala Pro Leu Lys Pro
        195                 200                 205

Phe Ser His Pro Val Asp Ala Val Ile Tyr Glu Thr His Leu Arg Asp
210                 215                 220

Phe Ser Ile His Glu Asn Ser Gly Met Ile Asn Lys Gly Lys Tyr Leu
225                 230                 235                 240

Ala Leu Thr Glu Thr Asp Thr Gln Thr Ala Asn Gly Ser Ser Ser Gly
                245                 250                 255

Leu Ala Tyr Val Lys Glu Leu Gly Val Thr His Val Glu Leu Leu Pro
            260                 265                 270

Val Asn Asp Phe Ala Gly Val Asp Glu Glu Lys Pro Leu Asp Ala Tyr
        275                 280                 285

Asn Trp Gly Tyr Asn Pro Leu His Phe Phe Ala Pro Glu Gly Ser Tyr
290                 295                 300

Ala Ser Asn Pro His Asp Pro Gln Thr Arg Lys Thr Glu Leu Lys Gln
305                 310                 315                 320

Met Ile Asn Thr Leu His Gln His Gly Leu Arg Val Ile Leu Asp Val
                325                 330                 335

Val Phe Asn His Val Tyr Lys Arg Glu Asn Ser Pro Phe Glu Lys Thr
            340                 345                 350

Val Pro Gly Tyr Phe Phe Arg His Asp Glu Cys Gly Met Pro Ser Asn
        355                 360                 365
```

Gly Thr Gly Val Gly Asn Asp Ile Ala Ser Glu Arg Arg Met Ala Arg
            370                 375                 380

Lys Phe Ile Ala Asp Cys Val Val Tyr Trp Leu Glu Glu Tyr Asn Ala
385                 390                 395                 400

Asp Gly Phe Arg Phe Asp Leu Leu Gly Ile Leu Asp Ile Asp Thr Val
            405                 410                 415

Leu Tyr Met Lys Glu Lys Ala Thr Lys Ala Lys Pro Gly Ile Leu Leu
            420                 425                 430

Phe Gly Glu Gly Trp Asp Leu Ala Thr Pro Leu Pro His Glu Gln Lys
            435                 440                 445

Ala Ala Leu Ala Asn Ala Pro Arg Ile Pro Gly Ile Gly Phe Phe Asn
450                 455                 460

Asp Met Phe Arg Asp Ala Val Lys Gly Asn Thr Phe His Leu Lys Ala
465                 470                 475                 480

Val Gly Phe Ala Leu Gly Ser Gly Glu Ser Ala Gln Ala Val Met His
            485                 490                 495

Gly Ile Ala Gly Ser Ser Gly Trp Lys Ala Leu Ala Pro Ile Val Pro
            500                 505                 510

Glu Pro Ser Gln Ser Ile Asn Tyr Val Glu Ser His Asp Asn His Thr
            515                 520                 525

Phe Trp Asp Lys Met Ser Phe Ala Leu Pro Gln Glu Asn Asp Ser Arg
530                 535                 540

Lys Arg Ser Arg Gln Arg Leu Ala Ala Ile Ile Leu Leu Ala Gln
545                 550                 555                 560

Gly Val Pro Phe Ile His Ser Gly Gln Glu Phe Phe Arg Thr Lys Gln
            565                 570                 575

Gly Val Glu Asn Ser Tyr Gln Ser Ser Asp Ser Ile Asn Gln Leu Asp
            580                 585                 590

Trp Asp Arg Arg Glu Thr Phe Lys Glu Asp Val His Tyr Ile Arg Arg
            595                 600                 605

Leu Ile Ser Leu Arg Lys Ala His Pro Ala Phe Arg Leu Arg Ser Ala
            610                 615                 620

Ala Asp Ile Arg Arg His Leu Glu Cys Leu Thr Leu Lys Glu His Leu
625                 630                 635                 640

Ile Ala Tyr Arg Leu Tyr Asp Leu Asp Glu Val Asp Glu Trp Lys Asp
            645                 650                 655

Ile Ile Val Ile His His Ala Ser Pro Asp Ser Val Glu Trp Ser Leu
            660                 665                 670

Pro Asn Asp Ile Pro Tyr Arg Leu Leu Cys Asp Pro Ser Gly Phe Gln
            675                 680                 685

Glu Asp Thr Ala Glu Ile Lys Lys Thr Val Ala Val Asn Gly Ile Gly
            690                 695                 700

Thr Val Ile Leu Tyr Leu Ala Ser Asp Leu Lys Ser Phe Ala
705                 710                 715

<210> SEQ ID NO 47
<211> LENGTH: 718
<212> TYPE: PRT
<213> ORGANISM: Bacillus sp.

<400> SEQUENCE: 47

Met Val Ser Ile Arg Arg Ser Phe Glu Ala Tyr Val Asp Asp Met Asn
1               5                   10                  15

Ile Ile Thr Val Leu Ile Pro Ala Glu Gln Lys Gly Ile Met Thr Pro

```
                20                  25                  30
Pro Phe Arg Leu Glu Thr Glu Thr Val Phe Pro Leu Ala Val Arg
            35                  40                  45
Glu Glu Tyr Ser Leu Glu Ala Lys Tyr Lys Tyr Val Cys Val Ser Asp
50                  55                  60
His Pro Val Thr Phe Gly Lys Ile His Cys Val Arg Ala Ser Ser Gly
65                  70                  75                  80
His Lys Thr Asp Leu Gln Ile Gly Ala Val Ile Arg Thr Ala Ala Phe
                85                  90                  95
Asp Asp Glu Phe Tyr Tyr Asp Gly Leu Gly Ala Val Tyr Thr Ala
                100                 105                 110
Asp His Thr Val Phe Lys Val Trp Ala Pro Ala Ala Thr Ser Ala Ala
            115                 120                 125
Val Lys Leu Ser Tyr Pro Asn Lys Ser Gly Arg Thr Phe Gln Met Thr
        130                 135                 140
Arg Leu Glu Lys Gly Val Tyr Ala Val Thr Val Thr Gly Asp Leu His
145                 150                 155                 160
Gly Tyr Glu Tyr Leu Phe Cys Ile Cys Asn Asn Ser Glu Trp Met Glu
                165                 170                 175
Thr Val Asp Pro Tyr Ala Lys Ala Val Thr Val Asn Gly Glu Lys Gly
            180                 185                 190
Val Val Leu Arg Pro Asp Gln Met Lys Trp Thr Ala Pro Leu Lys Pro
        195                 200                 205
Phe Ser His Pro Val Asp Ala Val Ile Tyr Glu Thr His Leu Arg Asp
    210                 215                 220
Phe Ser Ile His Glu Asn Ser Gly Met Ile Asn Lys Gly Lys Tyr Leu
225                 230                 235                 240
Ala Leu Thr Glu Thr Asp Thr Gln Thr Ala Asn Gly Ser Ser Ser Gly
                245                 250                 255
Leu Ala Tyr Val Lys Glu Leu Gly Val Thr His Val Glu Leu Leu Pro
            260                 265                 270
Val Asn Asp Phe Ala Gly Val Asp Glu Glu Lys Pro Leu Asp Ala Tyr
        275                 280                 285
Asn Trp Gly Tyr Asn Pro Leu His Phe Phe Ala Pro Glu Gly Ser Tyr
    290                 295                 300
Ala Ser Asn Pro His Asp Pro Gln Thr Arg Lys Thr Glu Leu Lys Gln
305                 310                 315                 320
Met Ile Asn Thr Leu His Gln His Gly Leu Arg Val Ile Leu Asp Val
                325                 330                 335
Val Phe Asn His Val Tyr Lys Arg Glu Asn Ser Pro Phe Glu Lys Thr
            340                 345                 350
Val Pro Gly Tyr Phe Phe Arg His Asp Glu Cys Gly Met Pro Ser Asn
        355                 360                 365
Gly Thr Gly Val Gly Asn Asp Ile Ala Ser Glu Arg Arg Met Ala Arg
    370                 375                 380
Lys Phe Ile Ala Asp Cys Val Val Tyr Trp Leu Glu Glu Tyr Asn Val
385                 390                 395                 400
Asp Gly Phe Arg Phe Asp Leu Leu Gly Ile Leu Asp Ile Asp Thr Val
                405                 410                 415
Leu Tyr Met Lys Glu Lys Ala Thr Lys Ala Lys Pro Gly Ile Leu Leu
            420                 425                 430
Phe Gly Glu Gly Trp Asp Leu Ala Thr Pro Leu Pro His Glu Gln Lys
        435                 440                 445
```

```
Ala Ala Leu Ala Asn Ala Pro Arg Met Pro Gly Ile Gly Phe Phe Asn
            450                 455                 460

Asp Met Phe Arg Asp Ala Val Lys Gly Asn Thr Phe His Leu Lys Ala
465                 470                 475                 480

Val Gly Phe Ala Leu Gly Ser Gly Glu Ser Ala Gln Ala Val Met His
                485                 490                 495

Gly Ile Ala Gly Ser Ser Gly Trp Lys Ala Leu Ala Pro Ile Val Pro
                500                 505                 510

Glu Pro Ser Gln Ser Ile Asn Tyr Val Glu Ser His Asp Asn His Thr
            515                 520                 525

Phe Trp Asp Lys Met Ser Phe Ala Leu Pro Gln Glu Asn Asp Ser Arg
            530                 535                 540

Lys Arg Ser Arg Gln Arg Leu Ala Ala Ala Ile Ile Leu Leu Ala Gln
545                 550                 555                 560

Gly Val Pro Phe Ile His Ser Gly Gln Glu Phe Phe Arg Thr Lys Gln
                565                 570                 575

Gly Val Glu Asn Ser Tyr Gln Ser Ser Asp Ser Ile Asn Gln Leu Asp
                580                 585                 590

Trp Asp Arg Arg Glu Thr Phe Lys Glu Asp Val His Tyr Ile Arg Arg
            595                 600                 605

Leu Ile Ser Leu Arg Lys Ala His Pro Ala Phe Arg Leu Arg Ser Ala
            610                 615                 620

Ala Asp Ile Arg Arg His Leu Glu Cys Leu Thr Leu Lys Glu His Leu
625                 630                 635                 640

Ile Ala Tyr Arg Leu Tyr Asp Leu Asp Glu Val Asp Glu Trp Lys Asp
                645                 650                 655

Ile Ile Val Ile His His Ala Ser Pro Asp Ser Val Gly Trp Ser Leu
                660                 665                 670

Pro Asn Asp Ile Pro Tyr Arg Leu Leu Cys Asp Pro Ser Gly Phe Gln
            675                 680                 685

Glu Asp Pro Ala Glu Ile Lys Lys Thr Val Ala Val Asn Gly Ile Gly
            690                 695                 700

Thr Val Ile Leu Tyr Leu Ala Ser Asp Leu Lys Ser Phe Ala
705                 710                 715

<210> SEQ ID NO 48
<211> LENGTH: 718
<212> TYPE: PRT
<213> ORGANISM: Unknown
<220> FEATURE:
<223> OTHER INFORMATION: bacterial

<400> SEQUENCE: 48

Met Val Ser Ile Gln Arg Ser Phe Glu Ala Tyr Ala Asp Glu Met Asn
1               5                   10                  15

Ile Ile Thr Val Leu Ile Pro Ala Asp Gln Lys Asp Thr Phe Thr Pro
            20                  25                  30

Pro Phe Gln Leu Glu Thr Asp Thr Ala Glu Ile Pro Leu Thr Val Ser
        35                  40                  45

Gln Glu Trp Gln Ile Glu Gly Lys Cys Lys Tyr Val Cys Val Ala Glu
    50                  55                  60

Gln Pro Val Thr Phe Gly Lys Thr His His Val Lys Ala Ser Gly Gly
65                  70                  75                  80

Gly Lys Thr Asp Leu Gln Ile Gly Ala Val Val Arg Thr Asp Ala Phe
                85                  90                  95
```

```
Asp Ala Ala Phe Tyr Tyr Asp Gly Glu Leu Gly Ala Val Tyr Thr Ser
                100             105             110

Asp Tyr Thr Glu Phe Lys Val Trp Ala Pro Ala Ala Thr Ser Ala Ala
            115             120             125

Val Lys Leu Ser His Pro Glu Lys Ser Gly His Thr Leu Gln Met Thr
    130             135             140

Arg Met Glu Asn Gly Val Tyr Ala Val Thr Val Ala Gly Asp Leu His
145             150             155             160

Gly Tyr Glu Tyr Val Tyr Arg Ile Cys Asn Asn Leu Glu Trp Thr Glu
                165             170             175

Thr Val Asp Pro Tyr Ala Lys Ala Val Thr Val Asn Gly Glu Lys Gly
            180             185             190

Val Val Leu Arg Pro Asp Gln Ala Asn Ser Ala Pro Ser Leu Ala Pro
    195             200             205

Phe Ser Asp Pro Val Asp Ala Ile Ile Tyr Glu Met His Ile Arg Asp
210             215             220

Phe Ser Ile His Glu Asn Ser Gly Met Lys Asn Lys Gly Lys Tyr Ala
225             230             235             240

Ala Leu Ala Glu Thr Asp Thr Lys Thr Lys Asn Gly Ser Ser Thr Gly
                245             250             255

Leu Ser Tyr Leu Lys Glu Leu Gly Val Thr His Ile Glu Leu Leu Pro
            260             265             270

Leu Asn Asp Tyr Ala Gly Val Asp Glu Glu Asn Pro Leu Ala Ala Tyr
    275             280             285

Asn Trp Gly Tyr Asn Pro Leu His Phe Phe Ala Pro Glu Gly Ser Tyr
290             295             300

Ala Ser Asn Pro His Asp Pro Gln Thr Arg Asn Thr Glu Val Lys Gln
305             310             315             320

Met Ile His Thr Leu His Gln His Gly Leu Arg Val Ile Leu Asp Val
                325             330             335

Val Tyr Asn His Val Tyr Gln Arg Glu His Ser Pro Phe Glu Lys Thr
            340             345             350

Val Pro Gly Tyr Phe Phe Arg His Asp Gln Phe Gly Met Pro Ser Asn
    355             360             365

Gly Thr Gly Val Gly Asn Asp Ile Ala Ser Glu Arg Arg Met Ala Arg
370             375             380

Lys Phe Ile Thr Asp Cys Val Met Tyr Trp Leu Lys Glu Tyr Asp Val
385             390             395             400

Asp Gly Phe Arg Phe Asp Leu Leu Gly Ile Leu Asp Ile Glu Thr Val
                405             410             415

Leu His Met Lys Glu Lys Ala Ser Glu Val Lys Pro Gly Ile Leu Leu
            420             425             430

Phe Gly Glu Gly Trp Asp Leu Ala Thr Pro Leu Pro Pro Glu Gln Lys
    435             440             445

Ala Thr Leu Ala Asn Ala Ser Lys Met Pro Gly Val Gly Phe Phe Asn
450             455             460

Asp Ser Phe Arg Asp Ala Val Lys Gly Asn Thr Phe His Ile Ala Ala
465             470             475             480

Ala Gly Phe Ala Leu Gly Asn Gly Glu Gln Thr Glu Thr Val Met Arg
                485             490             495

Gly Ile Ala Gly Ser Ser Gly Trp Lys Glu Thr Ala Pro Leu Val Ser
            500             505             510
```

Ala Pro Ser Gln Ser Ile Asn Tyr Val Glu Ser His Asp Asn His Thr
            515                 520                 525

Phe Trp Asp Lys Met Ser Leu Ala Leu Pro Gln Glu Ser Glu Ser Arg
530                 535                 540

Lys Arg Ser Arg Gln Lys Leu Ala Ser Ala Ile Ile Leu Leu Ala Gln
545                 550                 555                 560

Gly Val Pro Phe Ile His Ser Gly Gln Glu Phe Phe Arg Thr Lys Gln
                565                 570                 575

Gly Val Glu Asn Ser Tyr Gln Ser Ser Asp Ser Ile Asn Gln Leu Asp
                580                 585                 590

Trp Ser Arg Arg Glu Thr Phe Lys Gln Asp Val Asp Tyr Val Arg Arg
            595                 600                 605

Leu Ile Ser Leu Arg Lys Ala His Pro Ala Phe Arg Leu Thr Ser Ser
            610                 615                 620

Ala Asp Ile Gln Arg Cys Leu Glu Cys Leu Ala Leu Lys Glu His Leu
625                 630                 635                 640

Ile Val Tyr Arg Leu Phe Asn Leu Gly Ala Ile Asp Glu Trp Glu Glu
                645                 650                 655

Ile Ile Val Ile His His Ala Ser Pro Asp Ser Val Thr Trp Gln Leu
                660                 665                 670

Pro Lys Asp Lys Ala Tyr Arg Leu Leu Cys Asp Thr Asp Gly Phe Arg
            675                 680                 685

Ala Asp Pro Gly Glu Ile Lys Lys Ala Val Ser Val Asn Gly Ile Gly
            690                 695                 700

Thr Val Ile Leu Tyr Leu Ala Arg Asp Leu Thr Ser Phe Ala
705                 710                 715

<210> SEQ ID NO 49
<211> LENGTH: 718
<212> TYPE: PRT
<213> ORGANISM: Unknown
<220> FEATURE:
<223> OTHER INFORMATION: bacterial

<400> SEQUENCE: 49

Met Val Ser Ile Gln Arg Ser Phe Glu Ala Tyr Ala Asp Glu Met Asn
1               5                   10                  15

Ile Ile Thr Val Leu Ile Pro Ala Asp Gln Lys Asp Thr Phe Thr Pro
            20                  25                  30

Pro Phe Gln Leu Glu Thr Asp Thr Ala Glu Ile Pro Leu Thr Val Ser
        35                  40                  45

Gln Glu Trp Gln Ile Glu Gly Lys Cys Lys Tyr Val Cys Val Ala Glu
    50                  55                  60

Gln Pro Val Thr Phe Gly Lys Thr His His Val Lys Ala Ser Gly Gly
65                  70                  75                  80

Gly Lys Thr Asp Leu Gln Ile Gly Ala Val Val Arg Thr Asp Ala Phe
                85                  90                  95

Asp Ala Ala Phe Tyr Tyr Asp Gly Glu Leu Gly Ala Val Tyr Thr Ser
            100                 105                 110

Asp Tyr Thr Glu Phe Lys Val Trp Ala Pro Ala Thr Ser Ala Ala
        115                 120                 125

Val Lys Leu Ser His Pro Glu Lys Ser Gly His Thr Leu Gln Met Thr
130                 135                 140

Arg Met Glu Asn Gly Val Tyr Ala Val Thr Val Ala Gly Asp Leu His
145                 150                 155                 160

-continued

```
Gly Tyr Glu Tyr Val Tyr Arg Ile Cys Asn Asn Leu Glu Trp Thr Glu
            165                 170                 175
Thr Val Asp Pro Tyr Ala Lys Ala Val Thr Val Asn Gly Glu Lys Gly
        180                 185                 190
Val Val Leu Arg Pro Asp Gln Ala Asn Ser Ala Pro Ser Leu Ala Pro
    195                 200                 205
Phe Ser Asp Pro Val Asp Ala Ile Ile Tyr Glu Met His Ile Arg Asp
210                 215                 220
Phe Ser Ile His Glu Asn Ser Gly Met Lys Asn Lys Gly Lys Tyr Ala
225                 230                 235                 240
Ala Leu Ala Glu Thr Asp Thr Lys Thr Lys Asn Gly Ser Ser Thr Gly
                245                 250                 255
Leu Ser Tyr Leu Lys Glu Leu Gly Val Thr His Ile Glu Leu Leu Pro
            260                 265                 270
Leu Asn Asp Tyr Ala Gly Val Asp Glu Glu Asn Pro Leu Ala Ala Tyr
        275                 280                 285
Asn Trp Gly Tyr Asn Pro Leu His Phe Phe Ala Pro Glu Gly Ser Tyr
    290                 295                 300
Ala Ser Asn Pro His Asp Pro Gln Thr Arg Asn Thr Glu Val Lys Gln
305                 310                 315                 320
Met Ile His Thr Leu His Gln His Gly Leu Arg Val Ile Leu Asp Val
                325                 330                 335
Val Tyr Asn His Val Tyr Gln Arg Glu His Ser Pro Phe Glu Lys Thr
            340                 345                 350
Val Pro Gly Tyr Phe Phe Arg His Asp Gln Phe Gly Met Pro Ser Asn
        355                 360                 365
Gly Thr Gly Val Gly Asn Asp Ile Ala Ser Glu Arg Arg Met Ala Arg
    370                 375                 380
Lys Phe Ile Thr Asp Cys Val Met Tyr Trp Leu Lys Glu Tyr Asp Val
385                 390                 395                 400
Asp Gly Phe Arg Phe Asp Leu Leu Gly Ile Leu Asp Ile Glu Thr Val
                405                 410                 415
Leu His Met Lys Glu Lys Ala Ser Glu Val Lys Ser Gly Ile Leu Leu
            420                 425                 430
Phe Gly Glu Gly Trp Asp Leu Ala Thr Pro Leu Pro Pro Glu Gln Lys
        435                 440                 445
Ala Thr Leu Ala Asn Ala Ser Lys Met Pro Gly Val Gly Phe Phe Asn
    450                 455                 460
Asp Ser Phe Arg Asp Ala Val Lys Gly Asn Thr Phe His Ile Ala Ala
465                 470                 475                 480
Ala Gly Phe Ala Leu Gly Asn Gly Glu Gln Thr Glu Thr Val Met Arg
                485                 490                 495
Gly Ile Ala Gly Ser Ser Gly Trp Lys Glu Thr Ala Pro Leu Val Ser
            500                 505                 510
Ala Pro Ser Gln Ser Ile Asn Tyr Val Glu Ser His Asp Asn His Thr
        515                 520                 525
Phe Trp Asp Lys Met Ser Leu Ala Leu Pro Gln Glu Ser Glu Ser Arg
    530                 535                 540
Lys Arg Ser Arg Gln Lys Leu Ala Ser Ala Ile Ile Leu Leu Ala Gln
545                 550                 555                 560
Gly Val Pro Phe Ile His Ser Gly Gln Glu Phe Phe Arg Thr Lys Gln
                565                 570                 575
Gly Val Glu Asn Ser Tyr Gln Ser Ser Asp Ser Ile Asn Gln Leu Asp
```

```
                580             585             590
Trp Ser Arg Arg Glu Thr Phe Lys Gln Asp Val Asp Tyr Val Arg Arg
        595                 600                 605

Leu Ile Ser Leu Arg Lys Ala His Pro Ala Phe Arg Leu Thr Ser Ser
        610                 615                 620

Ala Asp Ile Gln Arg Cys Leu Glu Cys Leu Ala Leu Lys Glu His Leu
625                 630                 635                 640

Ile Val Tyr Arg Leu Phe Asn Leu Gly Ala Ile Asp Glu Trp Glu Glu
                645                 650                 655

Ile Ile Val Ile His His Ala Ser Pro Asp Ser Val Thr Trp Gln Leu
                660                 665                 670

Pro Lys Asp Lys Ala Tyr Arg Leu Leu Cys Asp Thr Asp Gly Phe Arg
        675                 680                 685

Ala Asp Pro Gly Glu Ile Lys Lys Ala Val Ala Val Asn Gly Ile Gly
        690                 695                 700

Thr Val Ile Leu Tyr Leu Ala Arg Asp Leu Thr Ser Phe Ala
705                 710                 715

<210> SEQ ID NO 50
<211> LENGTH: 718
<212> TYPE: PRT
<213> ORGANISM: Bacillus subtilis

<400> SEQUENCE: 50

Met Val Ser Ile Cys Arg Ser Phe Glu Ala Tyr Val Asp Asp Met Asn
1               5                   10                  15

Ile Ile Thr Val Leu Ile Pro Ala Glu Gln Lys Glu Ile Met Thr Pro
                20                  25                  30

Pro Phe Arg Leu Glu Thr Glu Thr Thr Asp Phe Pro Leu Ala Val Arg
            35                  40                  45

Glu Glu Tyr Ser Leu Glu Ala Lys Tyr Lys Tyr Ile Cys Val Ser Asp
        50                  55                  60

His Pro Val Thr Phe Gly Lys Asn His Phe Val Ser Ala Ser Ser Gly
65                  70                  75                  80

His Lys Thr Asp Leu Gln Ile Gly Ala Val Ile Arg Thr Ala Ala Phe
                85                  90                  95

Asp Asp Glu Phe Tyr Tyr Asp Gly Glu Leu Gly Ala Val Tyr Thr Ala
            100                 105                 110

Asp His Thr Val Phe Lys Val Trp Ala Pro Ala Ala Thr Ser Ala Ala
        115                 120                 125

Val Lys Leu Ser His Pro Asn Lys Gly Gly Arg Thr Phe Gln Met Thr
130                 135                 140

Arg Leu Glu Lys Gly Val Tyr Ala Val Thr Val Met Gly Asp Leu His
145                 150                 155                 160

Gly Tyr Glu Tyr Val Phe Cys Ile Cys Asn Asn Ser Glu Trp Ala Glu
                165                 170                 175

Thr Val Asp Pro Tyr Ala Lys Ala Val Thr Val Asn Gly Glu Lys Gly
            180                 185                 190

Val Val Leu Arg Pro Asp Gln Met Lys Trp Thr Ala Gln Leu Lys Pro
        195                 200                 205

Phe Ser Asn Pro Val Asp Ala Val Ile Tyr Glu Thr His Leu Arg Asp
    210                 215                 220

Phe Ser Ile His Glu Asn Ser Gly Met Ile Asn Lys Gly Lys Tyr Leu
225                 230                 235                 240
```

```
Ala Leu Thr Glu Thr Asp Thr Gln Thr Ala Asn Gly Ser Ser Ser Gly
                245                 250                 255

Leu Ala Tyr Ile Lys Glu Leu Gly Val Thr His Val Glu Leu Leu Pro
            260                 265                 270

Val Asn Asp Phe Ala Gly Val Asp Glu Glu Lys Pro Leu Asp Ala Tyr
        275                 280                 285

Asn Trp Gly Tyr Asn Pro Val His Phe Phe Ala Pro Glu Gly Ser Tyr
    290                 295                 300

Ala Ser Asn Pro Tyr Asp Pro Gln Thr Arg Lys Thr Glu Leu Lys Gln
305                 310                 315                 320

Met Ile Asn Thr Leu His Gln His Gly Leu Arg Val Ile Leu Asp Val
                325                 330                 335

Val Phe Asn His Val Tyr His Arg Glu Asn Ser Pro Phe Glu Lys Thr
            340                 345                 350

Val Pro Gly Tyr Phe Phe Arg His Asp Glu Phe Gly Met Pro Ser Asn
        355                 360                 365

Gly Thr Gly Val Gly Asn Asp Ile Ala Ser Glu Arg Arg Met Ala Arg
    370                 375                 380

Lys Phe Ile Ala Asp Cys Val Val Tyr Trp Leu Glu Glu Tyr Asn Ala
385                 390                 395                 400

Asp Gly Phe Arg Phe Asp Leu Leu Gly Ile Leu Asp Ile Asp Thr Val
                405                 410                 415

Leu Tyr Met Lys Glu Lys Ala Thr Ala Lys Pro Gly Ile Leu Leu
            420                 425                 430

Phe Gly Glu Gly Trp Asp Leu Ala Thr Pro Leu Pro His Glu Gln Lys
        435                 440                 445

Ala Thr Leu Ala Asn Ala Pro Arg Met Pro Gly Ile Gly Phe Phe Asn
    450                 455                 460

Asp Val Phe Arg Asp Ala Val Lys Gly Asn Thr Phe His Leu Met Ala
465                 470                 475                 480

Ala Gly Phe Ala Leu Gly Ser Gly Glu Ser Ala Gln Ala Val Met His
                485                 490                 495

Gly Ile Ala Gly Ser Ser Gly Trp Lys Ala Phe Ala Pro Ile Val Pro
            500                 505                 510

Glu Pro Ser Gln Ser Ile Asn Tyr Val Glu Ser His Asp Asn His Thr
        515                 520                 525

Phe Trp Asp Lys Met Ser Phe Ala Leu Pro Gln Glu Asn Asp Ser Arg
    530                 535                 540

Lys Arg Ser Arg Gln Arg Leu Ala Ala Ile Ile Leu Leu Ala Gln
545                 550                 555                 560

Gly Val Pro Phe Ile His Ser Gly Gln Glu Phe Phe Arg Thr Lys Gln
                565                 570                 575

Gly Val Glu Asn Ser Tyr Gln Ser Ser Asp Ser Ile Asn Glu Leu Asp
            580                 585                 590

Trp Asp Arg Arg Glu Thr Phe Lys Glu Asp Val Asp Tyr Ile Arg Arg
        595                 600                 605

Leu Ile Ser Leu Arg Lys Ala His Pro Ala Phe Arg Leu Arg Ser Ala
    610                 615                 620

Ala Asp Ile Arg Arg His Leu Glu Cys Leu Thr Leu Lys Glu His Phe
625                 630                 635                 640

Ile Ala Tyr Arg Leu Tyr Asp Leu Asp Glu Val Asp Glu Trp Lys Asp
                645                 650                 655

Ile Ile Val Ile His His Ala Ser Pro Asn Ser Val Glu Trp Arg Leu
```

```
            660                 665                 670
Pro Asn Asp Lys Pro Tyr Arg Leu Leu Cys Asp Pro Ser Gly Phe Gln
            675                 680                 685

Gln Asp Pro Ala Glu Ile Lys Lys Thr Val Ala Val Asn Gly Ile Gly
            690                 695                 700

Thr Val Ile Leu Tyr Leu Ala Ser Asp Leu Lys Ser Phe Ala
705                 710                 715

<210> SEQ ID NO 51
<211> LENGTH: 718
<212> TYPE: PRT
<213> ORGANISM: Bacillus subtilis

<400> SEQUENCE: 51

Met Val Ser Ile Arg Arg Ser Phe Glu Ala Tyr Val Asp Asp Met Asn
1               5                   10                  15

Ile Ile Thr Val Leu Ile Pro Ala Glu Gln Lys Glu Ile Met Thr Pro
                20                  25                  30

Pro Phe Arg Leu Glu Thr Glu Thr Asp Phe Pro Leu Ala Val Arg
            35                  40                  45

Glu Glu Tyr Ser Leu Glu Ala Lys Tyr Lys Tyr Ile Cys Val Ser Asp
50                  55                  60

His Pro Val Thr Phe Gly Lys Ile His Phe Val Ser Ala Ser Ser Gly
65                  70                  75                  80

His Lys Thr Asp Leu Gln Ile Gly Ala Val Ile Arg Thr Ala Ala Phe
                85                  90                  95

Asp Asp Glu Phe Tyr Tyr Asp Gly Glu Leu Gly Ala Val Tyr Thr Ala
            100                 105                 110

Asp His Thr Val Phe Lys Val Trp Ala Pro Ala Ala Thr Ser Ala Ala
            115                 120                 125

Val Lys Leu Ser His Pro Asn Lys Gly Gly Arg Thr Phe Gln Met Thr
130                 135                 140

Arg Ser Glu Lys Gly Val Tyr Ala Val Thr Val Met Gly Asp Leu His
145                 150                 155                 160

Gly Tyr Glu Tyr Val Phe Cys Ile Cys Asn Asn Ser Glu Trp Ala Glu
                165                 170                 175

Thr Val Asp Pro Tyr Ala Lys Ala Val Thr Val Asn Gly Glu Lys Gly
            180                 185                 190

Val Val Leu Arg Pro Asp Gln Met Lys Trp Thr Ala Pro Leu Lys Pro
            195                 200                 205

Phe Ser Asn Pro Val Asp Ala Val Ile Tyr Glu Thr His Leu Arg Asp
            210                 215                 220

Phe Ser Ile His Glu Asn Ser Gly Met Ile Asn Lys Gly Lys Tyr Leu
225                 230                 235                 240

Ala Leu Thr Glu Thr Asp Thr Gln Thr Ser Ile Gly Ser Ser Ser Gly
                245                 250                 255

Leu Ala Tyr Ile Lys Glu Leu Gly Val Thr His Val Glu Leu Leu Pro
            260                 265                 270

Val Asn Asp Phe Ala Gly Val Asp Glu Glu Lys Pro Leu Asp Ala Tyr
            275                 280                 285

Asn Trp Gly Tyr Asn Pro Leu His Phe Phe Ala Pro Glu Gly Ser Tyr
            290                 295                 300

Ala Leu Asn Pro His Asp Pro Gln Thr Arg Lys Thr Glu Leu Lys Gln
305                 310                 315                 320
```

```
Met Ile Asn Thr Leu His Gln His Gly Leu Arg Val Ile Leu Asp Val
                325                 330                 335

Val Phe Asn His Val Phe His Arg Glu Asn Ser Pro Phe Glu Lys Thr
            340                 345                 350

Val Pro Gly Tyr Phe Phe Arg His Asp Glu Phe Gly Met Pro Ser Asn
            355                 360                 365

Gly Thr Gly Val Gly Asn Asp Ile Ala Ser Glu Arg Arg Met Ala Arg
            370                 375                 380

Lys Phe Ile Ala Asp Cys Val Val Tyr Trp Leu Glu Glu Tyr Asn Ala
385                 390                 395                 400

Asp Gly Phe Arg Phe Asp Leu Leu Gly Ile Leu Asp Ile Asp Thr Val
            405                 410                 415

Leu Tyr Met Lys Glu Lys Ala Thr Lys Ala Lys Pro Gly Ile Leu Phe
            420                 425                 430

Phe Gly Glu Gly Trp Asp Leu Ala Thr Pro Leu Pro His Glu Gln Lys
            435                 440                 445

Ala Ala Leu Ala Asn Ala Pro Arg Met Pro Gly Ile Gly Phe Phe Asn
            450                 455                 460

Asp Met Phe Arg Asp Ala Val Lys Gly Asn Thr Phe His Leu Met Ala
465                 470                 475                 480

Thr Gly Phe Ala Leu Gly Ser Gly Glu Ser Ala Gln Ala Val Met His
            485                 490                 495

Gly Ile Ala Gly Ser Ser Gly Trp Lys Ala Phe Ala Pro Ile Val Pro
            500                 505                 510

Glu Pro Ser Gln Ser Ile Asn Tyr Val Glu Ser His Asp Asn His Thr
            515                 520                 525

Phe Trp Asp Lys Met Ser Phe Ala Leu Pro Gln Glu Asn Asp Ser Arg
            530                 535                 540

Lys Arg Ser Arg Gln Arg Leu Ala Ala Ala Ile Ile Leu Leu Ala Gln
545                 550                 555                 560

Gly Val Pro Phe Ile His Ser Gly Gln Glu Phe Phe Arg Thr Lys Gln
            565                 570                 575

Gly Val Glu Asn Ser Tyr Gln Ser Ser Asp Ser Ile Asn Glu Leu Asp
            580                 585                 590

Trp Asp Arg Arg Glu Thr Phe Lys Glu Asp Val Asp Tyr Ile Arg Arg
            595                 600                 605

Leu Ile Ser Leu Arg Lys Ala His Pro Ala Phe Arg Leu Arg Ser Ala
            610                 615                 620

Ala Asp Ile Arg Arg His Leu Glu Cys Leu Thr Leu Lys Glu His Phe
625                 630                 635                 640

Ile Ala Tyr Arg Leu Tyr Asp Leu Asp Lys Val Asp Glu Trp Lys Asp
            645                 650                 655

Ile Ile Val Ile His His Ala Ser Pro Asp Ser Val Glu Trp Arg Leu
            660                 665                 670

Pro Asn Asp Lys Pro Tyr Arg Leu Leu Cys Asp Pro Ser Gly Phe Gln
            675                 680                 685

Gln Asp Pro Pro Glu Ile Lys Lys Thr Val Ala Val Asn Gly Ile Gly
            690                 695                 700

Thr Val Ile Leu Tyr Leu Ala Ser Asp Leu Lys Ser Phe Ala
705                 710                 715

<210> SEQ ID NO 52
<211> LENGTH: 718
<212> TYPE: PRT
```

<213> ORGANISM: Bacillus subtilis

<400> SEQUENCE: 52

```
Met Val Ser Ile Arg Ser Phe Glu Ala Tyr Val Asp Asp Met Asn
1               5                   10                  15

Ile Ile Thr Val Leu Ile Pro Ala Glu Gln Lys Glu Ile Met Thr Pro
                20                  25                  30

Pro Phe Arg Leu Glu Thr Glu Thr Thr Asp Phe Pro Leu Ala Val Arg
        35                  40                  45

Glu Glu Tyr Ser Leu Glu Ala Lys Tyr Lys Tyr Ile Cys Val Ser Asp
    50                  55                  60

His Pro Val Thr Phe Gly Lys Ile His Phe Val Ser Ala Ser Ser Gly
65                  70                  75                  80

His Lys Thr Asp Leu Gln Ile Gly Ala Val Ile Arg Thr Ala Ala Phe
                85                  90                  95

Asp Asp Glu Phe Tyr Tyr Asp Gly Glu Leu Gly Ala Val Tyr Thr Ala
            100                 105                 110

Asp His Thr Val Phe Lys Val Trp Ala Pro Ala Ala Thr Ser Ala Ala
        115                 120                 125

Val Lys Leu Ser His Pro Asn Lys Gly Gly Arg Thr Phe Gln Met Thr
    130                 135                 140

Arg Leu Glu Lys Gly Val Tyr Ala Val Thr Val Met Gly Asp Leu His
145                 150                 155                 160

Gly Tyr Glu Tyr Val Phe Cys Ile Cys Asn Asn Ser Glu Trp Ala Glu
                165                 170                 175

Thr Val Asp Pro Tyr Ala Lys Ala Val Thr Val Asn Gly Glu Lys Gly
            180                 185                 190

Val Val Leu Arg Pro Asp Gln Met Lys Trp Thr Ala Pro Leu Lys Pro
        195                 200                 205

Phe Ser Asn Pro Val Asp Ala Val Ile Tyr Glu Thr His Leu Arg Asp
    210                 215                 220

Phe Ser Ile His Glu Asn Ser Gly Met Ile Asn Lys Gly Lys Tyr Leu
225                 230                 235                 240

Ala Leu Thr Glu Thr Asp Thr Gln Thr Ala Asn Gly Ser Ser Ser Gly
                245                 250                 255

Leu Ala Tyr Ile Lys Glu Leu Gly Val Thr His Val Glu Leu Leu Pro
            260                 265                 270

Val Asn Asp Phe Ala Gly Val Asp Glu Glu Lys Pro Leu Asp Ala Tyr
        275                 280                 285

Asn Trp Gly Tyr Asn Pro Val His Phe Ala Pro Glu Gly Ser Tyr
    290                 295                 300

Ala Ser Asn Pro Tyr Asp Pro Gln Thr Arg Lys Thr Glu Leu Lys Gln
305                 310                 315                 320

Met Ile Asn Thr Leu His Gln His Gly Leu Arg Val Ile Leu Asp Val
                325                 330                 335

Val Phe Asn His Val Tyr His Arg Glu Asn Ser Pro Phe Glu Lys Thr
            340                 345                 350

Val Pro Gly Tyr Phe Phe Arg His Asp Glu Phe Gly Met Pro Ser Asn
        355                 360                 365

Gly Thr Gly Val Gly Asn Asp Ile Ala Ser Glu Arg Arg Met Ala Arg
    370                 375                 380

Lys Phe Ile Ala Asp Cys Val Val Tyr Trp Leu Glu Glu Tyr Asn Ala
385                 390                 395                 400
```

```
Asp Gly Phe Arg Phe Asp Leu Leu Gly Ile Leu Asp Ile Asp Thr Val
                405                 410                 415
Leu Tyr Met Lys Glu Lys Ala Thr Lys Ala Lys Pro Gly Ile Leu Leu
            420                 425                 430
Phe Gly Glu Gly Trp Asp Leu Ala Thr Pro Leu Pro His Glu Gln Lys
        435                 440                 445
Ala Thr Leu Ala Asn Ala Pro Arg Met Pro Gly Ile Gly Phe Phe Asn
    450                 455                 460
Asp Val Phe Arg Asp Ala Val Lys Gly Asn Thr Phe His Leu Met Ala
465                 470                 475                 480
Ala Gly Phe Ala Leu Gly Ser Gly Glu Ser Ala Gln Ala Val Met His
                485                 490                 495
Gly Ile Ala Gly Ser Ser Gly Trp Lys Glu Leu Ala Pro Ile Val Ala
            500                 505                 510
Glu Pro Ser Gln Ser Ile Asn Tyr Val Glu Ser His Asp Asn His Thr
        515                 520                 525
Phe Trp Asp Lys Met Ser Phe Ala Leu Pro Gln Glu Asn Asp Ser Arg
    530                 535                 540
Lys Arg Ser Arg Gln Arg Leu Ala Ala Ala Ile Ile Leu Leu Ala Gln
545                 550                 555                 560
Gly Val Pro Phe Ile His Ser Gly Gln Glu Phe Phe Arg Thr Lys Gln
                565                 570                 575
Gly Val Glu Asn Ser Tyr Gln Ser Ser Asp Ser Ile Asn Glu Leu Asp
            580                 585                 590
Trp Asp Arg Arg Glu Thr Phe Lys Glu Asp Val Asp Tyr Ile Arg Arg
        595                 600                 605
Leu Ile Ser Leu Arg Lys Ala His Pro Ala Phe Arg Leu Arg Ser Ala
    610                 615                 620
Ala Asp Ile Arg Arg His Leu Glu Cys Leu Thr Leu Lys Glu His Phe
625                 630                 635                 640
Ile Ala Tyr Arg Leu Tyr Asp Leu Asp Lys Val Asp Glu Trp Lys Asp
                645                 650                 655
Ile Ile Val Ile His His Ala Ser Pro Asp Phe Val Glu Trp Arg Leu
            660                 665                 670
Pro Asn Asp Lys Pro Tyr Arg Leu Leu Cys Asp Pro Ser Gly Phe Gln
        675                 680                 685
Gln Asp Pro Pro Glu Ile Lys Lys Thr Val Ala Val Asn Gly Ile Gly
    690                 695                 700
Thr Val Ile Leu Tyr Leu Ala Ser Asp Leu Lys Ser Phe Ala
705                 710                 715

<210> SEQ ID NO 53
<211> LENGTH: 710
<212> TYPE: PRT
<213> ORGANISM: Bacillus atrophaeus

<400> SEQUENCE: 53

Met Val Cys Leu Asn Arg Lys Phe Glu Ala Tyr Leu Asp Glu Met Asp
1               5                   10                  15
Val Ile Thr Val Leu Ile Pro Ser Gly Lys Lys Glu Lys Tyr Thr Leu
            20                  25                  30
Pro Phe Val Leu Glu Thr Glu Ala Gly Asp Val Ser Leu Ser Val Arg
        35                  40                  45
Ala Glu Cys His Ile Asp Gly Lys Tyr Lys Tyr Ile Leu Val Ser Glu
    50                  55                  60
```

-continued

His Pro Val Ser Leu Gly Lys Thr His Tyr Ile Arg Ala Ser Gly Gly
65                  70                  75                  80

Asp Lys Thr Asp Leu Gln Ile Gly Ala Val Ile Arg Thr Glu Ala Phe
            85                  90                  95

Asp Ser Gln Phe Tyr Phe Asp Gly Ala Leu Gly Ala Asp Tyr Thr Pro
            100                 105                 110

Ser Arg Thr Val Phe Lys Val Trp Ala Pro Thr Ala Thr Ala Ala Ala
            115                 120                 125

Val Lys Leu Thr His Pro Glu Gln Gln Gly Leu Val Leu Gln Met Thr
            130                 135                 140

Arg Gln Asp His Gly Val Phe Ala Ala Leu Val Asp Gly Asp Leu His
145                 150                 155                 160

Gly Tyr Glu Tyr Met Tyr Arg Ile Cys Asn Asn Leu Glu Trp Thr Glu
                165                 170                 175

Thr Val Asp Pro Tyr Ala Lys Ala Val Thr Ile Asn Gly Glu Lys Gly
            180                 185                 190

Val Val Leu Arg Pro Glu Asn Pro Gln Ile Thr Ser Gln Gly Ile Pro
            195                 200                 205

Phe Ser Asn Pro Ala Asp Ala Val Ile Tyr Glu Leu His Ile Arg Asp
210                 215                 220

Phe Ser Ile His Glu Asn Ser Gly Met Lys Lys Gly Gln Tyr Leu
225                 230                 235                 240

Ala Met Thr Glu Thr Asp Ala Lys Thr Arg Glu Gly Val Ser Ala Gly
                245                 250                 255

Leu Ser Tyr Leu Lys Glu Leu Gly Val Thr His Ile Glu Leu Leu Pro
            260                 265                 270

Val Asn Asp Phe Ala Gly Val Asp Glu Lys Asn Pro Leu Ala Ala Tyr
            275                 280                 285

Asn Trp Gly Tyr Asn Pro Leu His Phe Phe Ala Pro Glu Gly Ser Tyr
290                 295                 300

Ser Ser Asp Pro Tyr Asn Pro Gln Val Arg Lys Ser Glu Leu Lys Glu
305                 310                 315                 320

Leu Ile Gln Thr Leu His Gln Asn Gly Leu Gln Val Ile Leu Asp Val
            325                 330                 335

Val Tyr Asn His Val Tyr Lys Arg Glu His Ser Pro Phe Glu Asn Thr
            340                 345                 350

Val Pro Gly Tyr Phe Phe Arg His Asp Ala Asp Gly Met Pro Ser Asn
            355                 360                 365

Gly Thr Gly Val Gly Asn Asp Ile Ala Ser Glu Arg Leu Met Ala Arg
            370                 375                 380

Lys Tyr Ile Ile Asp Cys Val His Trp Leu Lys Glu Tyr Asp Ala
385                 390                 395                 400

Asp Gly Phe Arg Phe Asp Leu Met Gly Ile Leu Asp Ile Glu Thr Val
            405                 410                 415

Arg Gln Ile Arg Glu Arg Ala Leu Ala Val Lys Pro Gly Ile Leu Leu
            420                 425                 430

Phe Gly Glu Gly Trp Asn Leu Asp Thr Pro Ile Ser Asp Asp Lys Lys
            435                 440                 445

Ala Thr Leu Ala Asn Ala Phe Gln Leu Pro Gly Ile Gly Phe Phe Asn
            450                 455                 460

Asp Ser Phe Arg Asp Ala Val Lys Gly Ser Thr Phe Gln Arg Glu Ala
465                 470                 475                 480

```
Ala Gly Phe Ala Leu Gly Asn Gly Asp Gln Ile Asp Ala Val Ile His
                485                 490                 495

Gly Ile Thr Gly Ser Ala Gly Trp Lys Glu Thr Asp Pro Met Val Gln
            500                 505                 510

Glu Pro Ser Gln Ser Val Asn Tyr Val Glu Ser His Asp Asn His Thr
        515                 520                 525

Phe Trp Asp Lys Met Gln Tyr Val Leu Pro His Glu Thr Asp Ser Val
    530                 535                 540

Lys Arg Ser Arg Gln Lys Leu Ala Thr Ala Val Val Leu Leu Ala Gln
545                 550                 555                 560

Gly Ile Pro Phe Ile His Ser Gly Gln Glu Phe Phe Arg Thr Lys Gln
                565                 570                 575

Gly Asp Glu Asn Ser Tyr Gln Ser Gly Asp Ser Val Asn Arg Leu Asp
            580                 585                 590

Trp Thr Arg Arg Ser Glu Phe Arg Glu Asp Val Glu Tyr Val Arg Arg
        595                 600                 605

Leu Ile Glu Ile Arg Lys Ala His Pro Ala Phe Arg Leu Lys Arg Ala
    610                 615                 620

Ala Glu Val Val Arg His Leu Asp Phe Leu Glu Val Arg Gly His Leu
625                 630                 635                 640

Ile Ala Tyr Arg Leu Phe Asp Leu Glu Thr Met Asp Glu Trp Lys Glu
                645                 650                 655

Ile Ile Ile Val His His Ser Ser Pro Asp Lys Ala Glu Met Met Leu
            660                 665                 670

Pro Ala Gly Lys Thr Tyr Arg Leu Leu Cys Asp Pro Ser Gly Phe Arg
        675                 680                 685

Glu Gln Pro Lys Glu Ile Lys Glu Leu Ile Ile Glu Gly Ile Gly
    690                 695                 700

Thr Cys Ile Leu Tyr Ile
705                 710

<210> SEQ ID NO 54
<211> LENGTH: 718
<212> TYPE: PRT
<213> ORGANISM: Unknown
<220> FEATURE:
<223> OTHER INFORMATION: bacterial

<400> SEQUENCE: 54

Met Val Ser Ile Gln Arg Ser Phe Glu Ala Tyr Ala Asp Glu Met Asn
1               5                   10                  15

Ile Ile Thr Val Leu Ile Pro Ala Asp Gln Lys Asp Thr Phe Thr Pro
            20                  25                  30

Pro Phe Gln Leu Glu Thr Asp Thr Ala Glu Ile Pro Leu Thr Val Ser
        35                  40                  45

Gln Glu Trp Gln Ile Glu Gly Lys Cys Lys Tyr Val Cys Val Ala Lys
    50                  55                  60

Gln Pro Val Thr Phe Gly Lys Thr His His Val Lys Ala Ser Gly Gly
65                  70                  75                  80

Gly Lys Thr Asp Leu Gln Ile Gly Ala Val Val Arg Thr Asp Ala Phe
                85                  90                  95

Asp Ala Ala Phe Tyr Tyr Asp Gly Glu Leu Gly Ala Val Tyr Thr Ser
            100                 105                 110

Asp Tyr Thr Glu Phe Lys Val Trp Ala Pro Ala Ala Thr Ser Ala Ala
        115                 120                 125
```

Val Lys Leu Ser His Pro Glu Lys Ser Gly His Thr Leu Gln Met Thr
130                 135                 140

Arg Met Glu Asn Gly Val Tyr Ala Val Thr Val Ala Gly Asp Leu His
145                 150                 155                 160

Gly Tyr Glu Tyr Val Tyr Arg Ile Cys Asn Asn Leu Glu Trp Thr Glu
                165                 170                 175

Thr Val Asp Pro Tyr Ala Lys Ala Val Thr Val Asn Gly Glu Lys Gly
                180                 185                 190

Val Val Leu Arg Pro Asp Gln Ala Asn Ser Ala Pro Ser Leu Ala Pro
            195                 200                 205

Phe Ser Asp Pro Val Asp Ala Ile Ile Tyr Glu Met His Ile Arg Asp
210                 215                 220

Phe Ser Ile His Glu Asn Ser Gly Met Lys Asn Lys Gly Lys Tyr Ala
225                 230                 235                 240

Ala Leu Ala Glu Thr Asp Thr Lys Thr Lys Asn Gly Ser Ser Thr Gly
                245                 250                 255

Leu Ser Tyr Leu Lys Glu Leu Gly Val Thr His Ile Glu Leu Leu Pro
            260                 265                 270

Leu Asn Asp Tyr Ala Gly Val Asp Glu Glu Asn Pro Leu Ala Ala Tyr
            275                 280                 285

Asn Trp Gly Tyr Asn Pro Leu His Phe Phe Ala Pro Glu Gly Ser Tyr
290                 295                 300

Ala Ser Asn Pro His Asp Pro Gln Thr Arg Asn Thr Glu Val Lys Gln
305                 310                 315                 320

Met Ile His Thr Leu His Gln His Gly Leu Arg Val Ile Leu Asp Val
                325                 330                 335

Val Tyr Asn His Val Tyr Gln Arg Glu His Ser Pro Phe Glu Lys Thr
            340                 345                 350

Val Pro Gly Tyr Phe Phe Arg His Asp Gln Phe Gly Met Pro Ser Asn
            355                 360                 365

Gly Thr Gly Val Gly Asn Asp Ile Ala Ser Glu Arg Arg Met Ala Arg
370                 375                 380

Lys Phe Ile Thr Asp Cys Val Met Tyr Trp Leu Lys Glu Tyr Asp Val
385                 390                 395                 400

Asp Gly Phe Arg Phe Asp Leu Leu Gly Ile Leu Asp Ile Glu Thr Val
                405                 410                 415

Leu His Met Lys Glu Lys Ala Ser Glu Val Lys Pro Gly Ile Leu Leu
            420                 425                 430

Phe Gly Glu Gly Trp Asp Leu Ala Thr Pro Leu Leu Pro Glu Gln Lys
            435                 440                 445

Ala Thr Leu Ala Asn Ala Ser Lys Met Pro Gly Val Gly Phe Phe Asn
450                 455                 460

Asp Ser Phe Arg Asp Ala Val Lys Gly Asn Thr Phe His Ile Ala Ala
465                 470                 475                 480

Ala Gly Phe Ala Leu Gly Asn Gly Glu Gln Thr Glu Thr Val Met Arg
                485                 490                 495

Gly Ile Ala Gly Ser Ser Gly Trp Lys Glu Thr Ala Pro Leu Val Ser
            500                 505                 510

Ala Pro Ser Gln Ser Ile Asn Tyr Val Glu Ser His Asp Asn His Thr
            515                 520                 525

Phe Trp Asp Lys Met Ser Leu Ala Leu Pro Gln Glu Ser Glu Ser Arg
530                 535                 540

Lys Arg Ser Arg Gln Lys Leu Ala Ser Ala Ile Ile Leu Leu Ala Gln

```
            545                 550                 555                 560
Gly Val Pro Phe Ile His Ser Gly Gln Glu Phe Phe Arg Thr Lys Gln
                    565                 570                 575

Gly Val Glu Asn Ser Tyr Gln Ser Ser Asp Ser Ile Asn Gln Leu Asp
                580                 585                 590

Trp Ser Arg Arg Glu Thr Phe Lys Gln Asp Val Asn Tyr Val Arg Arg
            595                 600                 605

Leu Ile Ser Leu Arg Lys Ala His Pro Ala Phe Arg Leu Thr Ser Ser
        610                 615                 620

Ala Asp Ile Gln Arg Cys Leu Glu Cys Leu Ala Leu Lys Glu His Leu
625                 630                 635                 640

Ile Val Tyr Arg Leu Phe Asn Leu Gly Ala Ile Asp Glu Trp Glu Glu
                    645                 650                 655

Ile Ile Val Ile His His Ala Ser Thr Asp Ser Phe Thr Trp Gln Leu
                660                 665                 670

Pro Lys Asp Lys Ala Tyr Arg Leu Leu Cys Asp Thr Asp Gly Phe Arg
            675                 680                 685

Ala Glu Ser Gly Glu Ile Lys Lys Ala Val Ala Val Asn Gly Ile Gly
        690                 695                 700

Thr Val Ile Leu Tyr Leu Ala Arg Asp Leu Thr Ser Phe Ala
705                 710                 715
```

```
<210> SEQ ID NO 55
<211> LENGTH: 718
<212> TYPE: PRT
<213> ORGANISM: Unknown
<220> FEATURE:
<223> OTHER INFORMATION: bacterial

<400> SEQUENCE: 55

Met Val Ser Ile Gln Arg Ser Phe Glu Ala Tyr Ala Asp Glu Met Asn
1               5                   10                  15

Ile Ile Thr Val Leu Ile Pro Ala Asp Gln Lys Asp Thr Phe Thr Pro
                20                  25                  30

Pro Phe Gln Leu Glu Thr Asp Thr Ala Glu Ile Pro Leu Thr Val Ser
            35                  40                  45

Gln Glu Trp Gln Ile Glu Gly Lys Cys Lys Tyr Val Cys Val Ala Glu
        50                  55                  60

Gln Pro Val Thr Phe Gly Lys Thr His His Val Lys Ala Ser Gly Gly
65                  70                  75                  80

Gly Lys Thr Asp Leu Gln Ile Gly Ala Val Val Arg Met Asp Ala Phe
                85                  90                  95

Asp Ala Ala Phe Tyr Tyr Asp Gly Glu Leu Gly Ala Val Tyr Thr Ser
                100                 105                 110

Asp Tyr Thr Glu Phe Lys Val Trp Ala Pro Ala Thr Ser Ala Ala
            115                 120                 125

Val Lys Leu Ser His Pro Glu Lys Ser Gly His Thr Leu Gln Met Thr
        130                 135                 140

Arg Met Glu Asn Gly Val Tyr Ala Val Thr Val Ala Gly Asp Leu His
145                 150                 155                 160

Gly Tyr Glu Tyr Val Tyr Arg Ile Cys Asn Asn Leu Glu Trp Thr Glu
                165                 170                 175

Thr Val Asp Pro Tyr Ala Lys Ala Val Thr Val Asn Gly Glu Lys Gly
                180                 185                 190

Val Val Leu Arg Pro Asp Gln Ala Asn Ser Ala Pro Ser Leu Ala Pro
```

```
            195                 200                 205
Phe Ser Asp Pro Val Asp Ala Ile Ile Tyr Glu Met His Ile Arg Asp
210                 215                 220

Phe Ser Ile His Glu Asn Ser Gly Met Lys Asn Lys Gly Lys Tyr Ala
225                 230                 235                 240

Ala Leu Ala Glu Thr Asp Thr Lys Thr Lys Asn Gly Ser Ser Thr Gly
                245                 250                 255

Leu Ser Tyr Leu Lys Glu Leu Gly Val Thr His Ile Glu Leu Leu Pro
            260                 265                 270

Leu Asn Asp Tyr Ala Gly Val Asp Glu Glu Asn Pro Leu Ala Ala Tyr
        275                 280                 285

Asn Trp Gly Tyr Asn Pro Leu His Phe Phe Ala Pro Glu Gly Ser Tyr
    290                 295                 300

Ala Ser Asn Pro His Asp Pro Gln Thr Arg Asn Thr Glu Val Lys Gln
305                 310                 315                 320

Met Ile His Thr Leu His Gln His Gly Leu Arg Val Ile Leu Asp Val
                325                 330                 335

Val Tyr Asn His Val Tyr Gln Arg Glu His Ser Pro Phe Glu Lys Thr
                340                 345                 350

Val Pro Gly Tyr Phe Phe Arg His Asp Gln Phe Gly Met Pro Ser Asn
            355                 360                 365

Gly Thr Gly Val Gly Asn Asp Ile Ala Ser Glu Arg Arg Met Ala Arg
370                 375                 380

Lys Phe Ile Thr Asp Cys Val Met Tyr Trp Leu Lys Glu Tyr Asp Val
385                 390                 395                 400

Asp Gly Phe Arg Phe Asp Leu Leu Gly Ile Leu Asp Ile Glu Thr Val
                405                 410                 415

Leu His Met Lys Glu Lys Ala Ser Glu Val Lys Pro Gly Ile Leu Leu
            420                 425                 430

Phe Gly Glu Gly Trp Asp Leu Ala Thr Pro Leu Pro Pro Glu Gln Lys
        435                 440                 445

Ala Thr Leu Ala Asn Ala Ser Lys Met Pro Gly Val Gly Phe Phe Asn
    450                 455                 460

Asp Ser Phe Arg Asp Ala Val Lys Gly Asn Thr Phe His Ile Ala Ala
465                 470                 475                 480

Ala Gly Phe Ala Leu Gly Asn Gly Glu Gln Thr Glu Thr Val Met Arg
                485                 490                 495

Gly Ile Ala Gly Ser Ser Gly Trp Lys Glu Thr Ala Pro Leu Val Ser
                500                 505                 510

Ala Pro Ser Gln Ser Ile Asn Tyr Val Glu Ser His Asp Asn His Thr
            515                 520                 525

Phe Trp Asp Lys Met Ser Leu Ala Leu Pro Gln Ser Glu Ser Glu Arg
        530                 535                 540

Lys Arg Ser Arg Gln Lys Leu Ala Ser Ala Ile Ile Leu Leu Ala Gln
545                 550                 555                 560

Gly Val Pro Phe Ile His Ser Gly Gln Glu Phe Phe Arg Thr Lys Gln
                565                 570                 575

Gly Val Glu Asn Ser Tyr Gln Ser Ser Asp Ser Ile Asn Gln Leu Asp
                580                 585                 590

Trp Ser Arg Cys Glu Thr Phe Lys Gln Asp Val Asp Tyr Val Arg Arg
            595                 600                 605

Leu Ile Ser Leu Arg Lys Ala His Pro Ala Phe Arg Leu Thr Ser Ser
        610                 615                 620
```

Ala Asp Ile Gln Arg Cys Leu Glu Cys Leu Ala Leu Lys Glu His Leu
625                 630                 635                 640

Ile Val Tyr Arg Leu Phe Asn Leu Gly Ala Ile Asp Glu Trp Glu Glu
            645                 650                 655

Ile Ile Val Ile His His Ala Ser Pro Asp Ser Val Thr Trp Gln Leu
            660                 665                 670

Pro Lys Asp Lys Ala Tyr Arg Leu Leu Cys Asp Thr Asp Gly Phe Arg
        675                 680                 685

Ala Asp Ser Gly Glu Ile Lys Lys Ala Val Ala Asn Gly Ile Gly
        690                 695                 700

Thr Val Ile Leu Tyr Leu Ala Arg Asp Leu Thr Ser Phe Ala
705                 710                 715

<210> SEQ ID NO 56
<211> LENGTH: 718
<212> TYPE: PRT
<213> ORGANISM: Bacillus subtilis

<400> SEQUENCE: 56

Met Val Ser Ile Arg Arg Ser Phe Glu Ala Tyr Val Asp Asp Met Asn
1               5                   10                  15

Val Ile Thr Val Leu Ile Pro Ala Glu Gln Lys Asp Ile Ile Lys Pro
            20                  25                  30

Pro Phe Arg Leu Glu Thr Glu Thr Ala Val Phe Pro Leu Ala Val Arg
        35                  40                  45

Glu Glu Tyr Arg Leu Glu Ala Thr Tyr Lys Tyr Val Cys Val Ser Asp
50                  55                  60

His Pro Val Thr Phe Gly Lys Ile His Ala Val Arg Ala Ser Ser Gly
65                  70                  75                  80

Asp Lys Thr Tyr Leu Gln Ile Gly Ala Val Ile Arg Thr Asp Ala Phe
            85                  90                  95

Asp Asp Ala Phe Tyr Tyr Asp Gly Glu Leu Gly Ala Val Tyr Thr Ala
        100                 105                 110

Asp Tyr Thr Glu Phe Lys Val Trp Ala Pro Ala Ala Val Ser Ala Ala
        115                 120                 125

Val Lys Leu Ser His Pro Asn Lys Ser Gly Leu Thr Phe Gln Met Thr
130                 135                 140

Arg Leu Glu Lys Gly Val Tyr Ala Val Thr Val Ser Gly Asp Leu His
145                 150                 155                 160

Gly Tyr Glu Tyr Val Phe Cys Ile Cys Asn Asn Ser Glu Trp Ala Glu
            165                 170                 175

Thr Val Asp Pro Tyr Ala Lys Ala Val Thr Val Asn Gly Glu Lys Gly
        180                 185                 190

Val Val Leu Arg Pro Asp Gln Met Lys Arg Ala Asp Pro Ile Glu Pro
        195                 200                 205

Phe Ser Asn Pro Ala Asp Ala Val Ile Tyr Glu Met His Ile Arg Asp
210                 215                 220

Phe Ser Ile His Glu Asn Ser Gly Met Lys Asn Lys Gly Lys Tyr Leu
225                 230                 235                 240

Ala Leu Thr Glu Thr Asp Thr Gln Thr Arg Lys Gly Cys Ser Ser Gly
            245                 250                 255

Leu Ala Tyr Val Lys Lys Leu Gly Val Thr His Val Glu Leu Leu Pro
        260                 265                 270

Val Asn Asp Phe Ala Gly Val Asp Glu Glu Lys Pro Leu Asp Ala Tyr

-continued

```
                275                 280                 285
Asn Trp Gly Tyr Asn Pro Leu His Phe Phe Ala Pro Glu Gly Ser Tyr
290                 295                 300
Ala Ser Asn Pro His Asp Pro Gln Thr Arg Lys Thr Glu Leu Lys Gln
305                 310                 315                 320
Met Ile Lys Ile Leu His Gln His Gly Leu Arg Val Ile Leu Asp Val
                325                 330                 335
Val Phe Asn His Val Tyr Glu Arg Glu Asn Ser Pro Phe Glu Lys Thr
            340                 345                 350
Val Pro Gly Tyr Tyr Phe Arg His Asp Glu Phe Gly Met Pro Ser Asn
            355                 360                 365
Gly Thr Gly Val Gly Asn Asp Ile Ala Ser Glu Arg Arg Met Ala Arg
370                 375                 380
Lys Phe Ile Ala Asp Cys Val Ile Tyr Trp Leu Glu Glu Tyr Asp Ala
385                 390                 395                 400
Asp Gly Phe Arg Phe Asp Leu Leu Gly Ile Leu Asp Ile Asp Thr Val
                405                 410                 415
Leu Tyr Ile Lys Glu Lys Ala Thr Ala Val Lys Pro Gly Ile Leu Leu
            420                 425                 430
Phe Gly Glu Gly Trp Asp Leu Ala Thr Pro Leu Pro His Glu Gln Lys
            435                 440                 445
Ala Ala Leu Ala Asn Ala Ser Lys Met Ala Gly Ile Gly Phe Phe Asn
450                 455                 460
Asp Met Phe Arg Asp Ala Val Lys Gly Asn Thr Phe His Leu Thr Ala
465                 470                 475                 480
Ala Gly Phe Ala Leu Gly Gly Gly Glu Ala Ala Lys Thr Val Met His
                485                 490                 495
Gly Ile Ala Gly Ser Ser Gly Trp Lys Ala Leu Ala Pro Val Val Pro
            500                 505                 510
Glu Pro Ser Gln Ser Ile Asn Tyr Val Glu Ser His Asp Asn His Thr
            515                 520                 525
Phe Trp Asp Lys Met Ser Leu Ala Leu Pro His Glu Thr Asp Ser Arg
            530                 535                 540
Lys Arg Ser Arg Gln Arg Leu Ala Ser Ala Ile Ile Leu Leu Ala Gln
545                 550                 555                 560
Gly Val Pro Phe Ile His Asn Gly Gln Glu Phe Phe Arg Thr Lys Gln
                565                 570                 575
Gly Val Glu Asn Ser Tyr Gln Ser Ser Asp Ser Ile Asn Gln Leu Asp
            580                 585                 590
Trp Asp Arg Arg Glu Thr Phe Lys Glu Asp Val Asp Tyr Ile Arg Arg
            595                 600                 605
Leu Ile Ser Leu Arg Lys Ala His Pro Ala Phe Arg Leu Asn Ser Ala
            610                 615                 620
Ala Asp Ile Gln Arg His Leu Glu Cys Leu Thr Leu Asn Glu His Leu
625                 630                 635                 640
Ile Ala Tyr Arg Leu His Asp Leu Gly Ala Phe Asp Lys Trp Glu Asp
                645                 650                 655
Ile Ile Val Ile His His Ala Ser Pro Glu Ser Val Glu Trp Lys Leu
            660                 665                 670
Pro Asn Asp Lys Thr Tyr Arg Leu Leu Cys Asp Thr Ser Gly Phe Gln
            675                 680                 685
```

```
His Ala Pro Lys Glu Ile Lys Lys Ala Val Ala Val Asn Gly Ile Gly
    690             695             700
Thr Val Ile Leu Tyr Leu Ala Ser Asp Leu Lys Ser Phe Ala
705             710             715
```